US007608453B2

(12) United States Patent
Cattaneo et al.

(10) Patent No.: US 7,608,453 B2
(45) Date of Patent: *Oct. 27, 2009

(54) INTRACELLULAR ANTIBODIES

(75) Inventors: Antonino Cattaneo, Trieste (IT); Amos Maritan, Trieste (IT); Michela Visintin, Trieste (IT); Terrence Rabbitts, Cambridge (GB); Giovanni Settanni, Orbassano (IT)

(73) Assignee: MRC Sissa-Scuola Internazionale Superiore de Studi Avanzati

( * ) Notice: Subject to any disclaimer, the term of this patent is extended or adjusted under 35 U.S.C. 154(b) by 143 days.

This patent is subject to a terminal disclaimer.

(21) Appl. No.: 10/771,257

(22) Filed: Feb. 3, 2004

(65) Prior Publication Data

US 2005/0288864 A1 Dec. 29, 2005

Related U.S. Application Data

(63) Continuation-in-part of application No. PCT/GB02/03512, filed on Aug. 1, 2002.

(51) Int. Cl.
*A61K 51/00* (2006.01)
*A61M 36/14* (2006.01)
*C12N 5/06* (2006.01)
*C12N 5/16* (2006.01)

(52) U.S. Cl. ............... 435/327; 435/331; 424/1.49

(58) Field of Classification Search ............... None
See application file for complete search history.

(56) References Cited

U.S. PATENT DOCUMENTS

| 5,171,838 | A | * | 12/1992 | Chiba ............... 530/326 |
| 5,681,722 | A | | 10/1997 | Newman ............ 435/69.7 |
| 6,949,245 | B1 | * | 9/2005 | Sliwkowski ......... 424/143.1 |
| 2003/0228663 | A1 | * | 12/2003 | Lowman et al. ...... 435/69.1 |

FOREIGN PATENT DOCUMENTS

| GB | 2344886 A | 6/2000 |
| WO | WO97/08320 | 3/1997 |
| WO | WO99/15897 | 4/1999 |
| WO | WO02/02641 A1 | 1/2002 |

OTHER PUBLICATIONS

Boehncke et al. The Importance of Dominant Negative Effects of Amino Acid Side Chain Substitution in Peptide-MHC molecule Interactions and T Cell Recognition, 1992, Journal of Immunology, vol. 150, pp. 331-341.*

Wu, et al., "Myosin-reactive Autoantibodies in Rheumatic Carditis and Normal Fetus", Clinical Immunology and Immunopathology (1998), V. 87, No. 2, pp. 184-192.
Goni, et al., "Amino acid sequence of the Fv region of a human monoclonal IgM (protein WEA) with antibody activity against 3, 4-pyruvylated galactose in Klebsiella polysaccharides K30 and K33", Proceedings of the National Academy of Sciences USA (1983), V. 80, No. 15, pp. 4837-4841.
Ohage, et al., "Intrabody Construction and Expression. I. The Critical Role of $V_L$ Domain Stability", Journal of Molecular Biology (1999), V. 291, No. 5, pp. 1119-1128.
The International Search Report (PCT/GB02/03512).
Database EMBL Online- Jan. 22, 1998, Database accession No. AAW27546.
Database EMBL Online Apr. 3, 1998, Database accession No. 171718.
Database EMBL Online Jan. 10, 2002, Database accession No. ABP45690.
Database EMBL Online May 1, 2000, Database accession No. Q9UL90.
Database EMBL Online Jul. 21, 1986, Database accession No. P01763.
Ohage, et al., "Intrabody Construction and Expression. II. A Synthetic Catalytic Fv Fragment", *J. Mol. Biol* (1999) V. 291, 1129-1134.
Proba, et al., "Antibody scFv Fragments Without Disulfide Bonds Made by Molecular Evolution", *J. Mol. Biol.* (1998), V. 275, pp. 245-253.
Wirtz, et al., "Intrabody Construction and Expression III: Engineering Hyperstable $V_H$ Domains", *Protein Science* (1999), V. 8, pp. 2245-2250.
Visintin, et al., "The Intracellular Antibody Capture Technology (IACT): Towards a Consensus Sequence for Intracellular Antibodies", *J. Mol. Biol.* (2002) V. 317, pp. 73-83.
Communication Relating to the Results of the Partial International Search Report (PCT/GB02/03512).

* cited by examiner

*Primary Examiner*—Michael Borin
*Assistant Examiner*—Jason M Sims
(74) *Attorney, Agent, or Firm*—Edwards Angell Palmer & Dodge LLP; Kathleen Williams; Amy DeCloux

(57) ABSTRACT

A method of identifying at least one consensus sequence for an intracellular antibody (ICS) comprising the steps of: creating a database comprising sequences of validated intracellular antibodies (VIDA database) and aligning the sequences of validated intracellular antibodies according to Kabat; determining the frequency with which a particular amino acid occurs in each of the positions of the aligned antibodies; selecting a frequency threshold value (LP or consensus threshold) in the range from 70% to 100%; identifying the positions of the alignment at which the frequency of a particular amino acid is greater than or equal to the LP value; and identifying the most frequent amino acid, in the position of said alignment.

2 Claims, 21 Drawing Sheets

FIG. 5B

```
              FR1              CDR1          FR2        CDR2                    FR3                              CDR3
         1         2         3         4         5            6         7         8         9         0         1         2         3
   12345678901234567890123456789 01ab234567890 1234567890 12345678901 2abc3456789012345678901234567890 12345678901 2abc34567890abcdefghijk1234567890123
Chothia
#A- QVQLQESGGGLVQPGRSLRLSCAASGFTFDDYAMH---WVRQAPGKGLEWVAVISY--DGSNKYYADSVKGRFTISRDNSKNTLYLQMNSLRAEDTAVYYCARDFAGAIAY-------------------WGQGTLVTVSS
#B- QVQLQESGGGLVQPGGSLRLSCAASGFTFSSYGMH---WVRQAPGKGLEWVAVISY--DGSNKYYADSVKGRFTISRDNSKNTLYLQMNSLRAEDTAVYYCAKDFAGAIAY-------------------WGQGTLVTVSS
#C- QVQLQESGGGLVQPGGSLRLSCAASGFTFDDYAMH---WVRQAPGKGLEWVAVISY--DGSNKYYADSVKGRFTISRDNSKNTLYLQMNSLRAEDTAVYYCARDFAGAIAY-------------------WGQGTLVTVSS
#D- QVQLVESGGGLVQPGGSLRLSCAASGFTFSSYAMS---WVRQAPGKGLEWVAAISG--SGDNTYYADSVKGRFTISRDNSENTVHLQMAGLRAEDTALYFCAKDGPAVGNPQ-----GYFDFWGRGTLVTVSS
#E- QVQLVESGGGLVQPGGSLRLSCAASGFTFSSYGMH---WVRQAPGKGLEWVASMSY--DGNKYYADSVKGRFTISRDNSKNTLYLQMNSLRAEDTAVYYCARDGIAARS-------GYYGMDVWGQGTLVTVSS
#F- QVQLVESGGGLVKPGGSLRLSCAASGFTFSDYYMS---WIRQAPGKGLEWVSSIS S-----SSSYIYYADSVKGRFTISRDNAKNSLYLQMNSLRAEDTAVYYCARDGIAARS----------------WGQGTLVTVSS
#G- QVQLVESGGGLVKPGGSLRLSCAASGFTFSDYYMS---WVRQAPGKGLEWVAVISY--DGSNKYYADSVKGRFTISRDNSKNTLYLQMNSLRAEDTAVYYCARDFAGAIAY-------------------WGQGTLVTVSS
#K- QVQLVQSGGGLVQPGGSLRLSCAASGFTFDDYAMH---WVRQAPGKGLEWVAVISY--DGSNKYYADSVKGRFTISRDNSENTVHLQMAGLRAEDTALYFCAKDLPDSNGY-----------------------WGQGTLVTVSS
#M- QVQLVQSGGGVVQPGRSLRLSCAASGFTFSSYAMS---WVRQAPGKGLEWVAVISY--DGSNKYYADSVKGRFTISRDNSKNTLYLQMNSLRAEDTAVYYCAKDLPDSNGY-----------------------WGQGTLVTVSS
#N- QVQLVESGGGVVQPGGSLRLSCAASGFTFSSYAMS---WVRQAPGKGLEWVAAISG--SGDNTYYADSVKGRFTISRDNSENTVHLQMAGLRAEDTALYFCAKDGPAVGNEQ-----GYFDFWGRGTLVTVSS
#O- QVQLVQSGGGVVQPGGSLRLSCAASGFTFDDYAMH---WVRQAPGKGLEWVAVISY--DGNKYYADSVKGRFTTPRDNSKNTLYLQMNSLRAEDTAVYYCARDFAGAIAY-------------------WGQGTLVTVSS
#Q- QVQLVQSGGGVVQPGGSLRLSCAASGFTFSSYGMH---WVRQAPGKGLEWVAVISY--DGSNKYYADSVKGRFTISRDNSKNTLYLQMNSLRAEDTAVYYCAKDLVGAKGN----------------------WAQGTLVTVSS
#T- QVQLVQSGGGVVQPGGSLRLSCAASGFTFSSYGMH---WARQAPGKGLEWVAVISY--DGSNKYYADSVKGRFTISRDNSKNTLYLQMNSLRAEDTAVYYCAKDLVGAKGN----------------------WGQGTLVTVSS
#V- QVQLVESGGGLVKPGGSLRLSCAASGFTFSSIAMS---WVRQAPGKGLEWVAAISG--SGDNTYYADSVKGRFTISRDNSENTVHLQMAGLRAEDTALYFCAKDGPEVGNPQ-----GYFDFWGRGTLVTVSS
#X- QVQLQQSGEGVVQPGGSLRLSCAASGFTFSSYGKH---WVRQAPGKGLEWVAVISY--DGSNKYYADSVKGRFTISRDNSKNTLYLQMNSLRAEDTAVYYCAKDLVGAKGN----------------------WGQGTLVTVSS
Y- QVQLVQSGGGVVQPGGSLRLSCAASGFTFSSYGMH---WVRQAPGKGLEWVASMSI--DGDNKYYADSVKGRFTISRDNSKNTLYLQMNSLRAEDTAVYYCARDLRGALDY----------------------WGQGTLVTVSS Human VH back primers                                                                                         Human JH for primers
        1         2         3                                                                                       9         0         1
chothia 123456789012345678901ab23456789012345678901 2abc34567890123456789012abc3456789012345678901 2abc34567890abcdefghijk1234567890123    VH
ICS
VHα-τ   QVQL SG G V PG SLRLSCAASGFTE    Y M  W RQAPGKGLEWV      S         YADSVKGRFT RDN   N     LQM     LRAEDTA Y CA D                 W   GTLVTVSS ← SEQ 4'

FIG. 11a
```

```
              FR1                    CDR1              FR2              CDR2                    FR3                                CDR3
        1         2         3             4         5         6                 7         8         9                    0
123456789012345678901234567890123456789 01abcdef234567890123456789012345678901234567890123456789012345678901234567890123456789012345abcdef67890123
Chothia
#A-EIVLTQSPSFLSASVGDRVTITCRASH-----GINNYLAWYQQKPGKAPKLLIYAASSLQSGVPSRFSGSGSGTDFTLTISSLQPEDFATYYCQQANSFP------LTFGGGTK
#B-EIVLTQSPSTLSASVGERVTITCRASQ-----SISSWLAWYQQKPGKAPKLLIYKASSLESGVPSRFSGSGSGTDFTLTISSLQPDDFATYYCQQYSTYL------WTFGQGTK
#C-EIVLTQSPSPSILSASVGDRVTITCRASH-----GINNYLAWYQQKPGKAPKLLIYAASSLQSGVPSRFSGSGSGTDFTLTISSLQPEDFATYYCQQANSFP------WTFGQGTK
#D-DIVMTQSPDSLAVSLGERATINCKSSQSLLYSSNNKDYLAWYQQKPGQSPRLLISWASTRESGVPDRFSGSGSGTDFTLTINRLQAEDVAVYYCQHYYSYP------LTFGGGTK
#E-EIVLTQSPSTLSASIGDRVTITCRASQ-----GISNYLAWYQQKPGKAPKLLIYAASTLQSGVPSRFSGSGSGTEFTLTISGLLPEDFASYFCQQASVFP------VTFGGGTK
#F-EIVLTQSPSFLSASVGDRVTITCRASH-----SISSWLAWYQQKPGKAPKLLIYAASILQSGVPSRFSGSGSGTDFTLTISSLQPEDFATYYCQQYSTYL------LTFGGGTK
#G-EIVLTQSPSFLSASVGDRVTITCRASH-----GINNYLAWYQQKPGKAPKLLIYAASSLQSGVPSRFSGSGSGTDFTLTISSLQPEDFATYYCQLQDSNPYPL----LTFGGGTK
#K-DIVMTQSPDSLAVSLGERATINCKSSQSLLYSSNNKDYLAWYQQKPGQSPRLLISWASTRESGVPDRFSGSGSGTDFTLTINRLQAEDVAVYYCQHYYSYP------LTFARTK
#M-DVVMTQSPDSLAVSLGERATINCKSSQSLLYSSNNKDYLAWYQQKPGQSPRLLISWASTRESGVPSRCSGSGSGSTDFTLTISSLQPDDFATYYCQHYYSYP-----WTFGQGTK
#N-DIVMTQSPDSLAVSLGERATINCKSSQSLLYSSRASE-----NINRWLAWYQQKPGQSPRLLIPWASTRESGVPSRFSGSGSGTDFTLTINRLQAEDVAVYYCQHYYSYP----LTFGQGTK
#O-EICVTQSPSTLSASVGERVTITCRASQ-----GISNYLAWYQQKPGKAPKLLIYAASSLQSGVPSRFSGSGSGTDFTLTISSLQPDDFATYYCQQANSFP------VTFARTK
#Q-EIVLTQSPSTLSASVGERVTITCRASQ-----GINNYLAWYQQKPGKAPKLLIYAASLQSGVPSRFSGSGSGTDFTLTISSLQPDDFATYYCQQANSFP------WTFGQGTK
#S-EIVLTQSPSTLSASVGERVTITCRASQ-----SISSWLAWYQQKPGKAPKVLIYKASSLESGVPSRFSGSGSGTDFTLTISSLQPDDFATYYCQQYSTYL------WTFGQGTK
#T-EIVLTQSPSTLSASVGERVTITCRASQ-----GINNYLAWYQQKPGKAPKVLIYKASSLESGVPSRFSGSGSGTDFTLTISSLQPDDFATYYCQQYSTYL------LTFGGGTK
#V-DIVMTKSPDSLAVSLGERATINCKSSQSLLYSSKNKDYLAWYQKRPGQSPRLLISWASTRESGVPDRFSGSGSGTDFTLTJNRLQAEDVAVYYCQHYYSIP-----WTFGQGTK
#X-EIVLTQSPSTLSASVGERVTITCRASQ-----SISSWLAWYQQKPGKAPKLLIYKASSLESGVPSRFSGSGSGTEFTLTISSLQPDDFATYYCQQYSTYL------LTFGGGTK
Y-EIVLTQSPSTLSASIGDRVTITCRASQ-----GISNYLAWYQQKPGKAPKLLIYAASTLQSGVPSRFSGSGSGTEFTLTISGLLPEDFASYFCLQASVFP------VTFGGGTK Human VK and λ back primers                                                                            Human Jk and Jλ for primers
                                                                                                                                            VL
Chothia 123456789012345678901abcdef234567890123456789012345678901234567890123456789012345678901234567890123456789012345abcdef67890123
ICS
VLα-r -  T SP  L  SGR TI C   S        LAWYQ KPG  P  LI  AS   SGVP  R  SGSGSGT FTLTI   L   D A Y C         TK ← SEQ 42
```

INTRACELLULAR ANTIBODIES

This application is a continuation-in-part of International Application No. PCT/GB02/03512, filed Aug. 1, 2002, which claims the priority of Great Britain Application No. GB 0119004.0, filed Aug. 3, 2001, Great Britain Application No. GB 0121577.1, filed Sep. 6, 2001, Italian Application No. IT RM2001A000633, filed Oct. 25, 2001, Great Britain Application No. GB 0200928.0, filed Jan. 16, 2002, and Great Britain Application No. GB 0203569.9, filed Feb. 14, 2002. Each of these applications is incorporated herein in its entirety by reference, including figures, tables and sequence listings.

The present invention relates to molecules which can function in an intracellular environment. In particular, the invention relates to the characteristics of immunoglobulin molecules which can bind selectively to a ligand within an intracellular environment. Uses of these molecules are also described.

BACKGROUND TO THE INVENTION

Intracellular antibodies or intrabodies have been demonstrated to function in antigen recognition in the cells of higher organisms (reviewed in Cattaneo, A. & Biocca, S. (1997) *Intracellular Antibodies: Development and Applications*. Landes and Springer-Verlag). This interaction can influence the function of cellular proteins which have been successfully inhibited in the cytoplasm, the nucleus or in the secretory pathway. This efficacy has been demonstrated for viral resistance in plant biotechnology (Tavladoraki, P., et al. (1993) *Nature* 366: 469-472) and several applications have been reported of intracellular antibodies binding to HIV viral proteins (Mhashilkar, A. M., et al. (1995) *EMBO J*. 14: 1542-51; Duan, L. & Pomerantz, R. J. (1994) *Nucleic Acids Res* 22: 5433-8; Maciejewski, J. P., et al. (1995) *Nat Med* 1: 667-73; Levy-Mintz, P., et al. (1996) *J. Virol*. 70: 8821-8832) and to oncogene products (Biocca, S., Pierandrei-Amaldi, P. & Cattaneo, A. (1993) *Biochem Biophys Res Commun* 197: 422-7; Biocca, S., Pierandrei-Amaldi, P., Campioni, N. & Cattaneo, A. (1994) *Biotechnology (N Y)* 12: 396-9; Cochet, O., et al. (1998) *Cancer Res* 58: 1170-6). The latter is an important area because enforced expression of oncogenes often occurs in tumour cells after chromosomal translocations (Rabbitts, T. H. (1994) *Nature* 372: 143-149). These proteins are therefore important intracellular therapeutic targets (Rabbitts, T. H. (1998) *New Eng. J. Med* 338: 192-194) which could be inactivated by binding with intracellular antibodies. Finally, the international efforts at whole genome sequencing will produce massive numbers of potential gene sequences which encode proteins about which nothing is known.

Functional genomics is an approach to ascertain the function of this plethora of proteins and the use of intracellular antibodies promises to be an important tool in this endeavour as a conceptually simple approach to knocking-out protein function directly by binding an antibody inside the cell.

Simple approaches to derivation of antibodies which function in cells are therefore necessary if their use is to have any impact on the large number of protein targets. In normal circumstances, the biosynthesis of immunoglobulin occurs into the endoplasmic reticulum for secretion as antibody. However, when antibodies are expressed in the cell cytoplasm (where the redox conditions are unlike those found in the ER) folding and stability problems occur resulting in low expression levels and the limited half-life of antibody domains. These problems are most likely due to the reducing environment of the cell cytoplasm (Hwang, C., Sinskey, A. J. & Lodish, H. F. (1992) *Science* 257: 1496-502), which hinders the formation of the intrachain disulphide bond of the VH and VL domains (Biocca, S., Ruberti, F., Tafani, M., Pierandrei-Amaldi, P. & Cattaneo, A. (1995) *Biotechnology (N Y)* 13: 1110-5; Martineau, P., Jones, P. & Winter, G. (1998) *J Mol Biol* 280: 117-127) important for the stability of the folded protein. However, some scFv have been shown to tolerate the absence of this bond (Proba, K., Honegger, A. & Pluckthun, A. (1997) *J Mol Biol* 265: 161-72; Proba, K., Worn, A., Honegger, A. & Pluckthun, A. (1998) *J Mol Biol* 275: 245-53) which presumably depends on the particular primary sequence of the antibody variable regions. No rules or consistent predictions until the present invention, been made about those antibodies which will tolerate the cell cytoplasm conditions. A further problem is the design of expression formats for intracellular antibodies and much effort has be expended on using scFv in which the VH and VL segments (i.e. the antibody combining site) are linked by a polypeptide linker at the C-terminus of VH and the N-terminus of $V_L$ (Bird, R. E., et al. (1988) *Science* 242: 423-6). While this is the most successful form for intracellular expression, it has a drawback in the lowering of affinity when converting from complete antibody (e.g. from a monoclonal antibody) to a scFv. Thus not all monoclonal antibodies can be made as scFv and maintain function in cells. Finally, different scFv fragments have distinct properties of solubility or propensity to aggregate when expressed in this cellular environment.

The antigen binding domain of an antibody comprises two separate regions: a heavy chain variable domain ($V_H$) and a light chain variable domain ($V_L$: which can be either $V_{kappa}$ or $V_{lambda}$). The antigen binding site itself is formed by six polypeptide loops: three from $V_H$ domain (H1, H2 and H3) and three from $V_L$ domain (L1, L2 and L3). A diverse primary repertoire of V genes that encode the $V_H$ and $V_L$ domains is produced by the combinatorial rearrangement of gene segments. The $V_H$ gene is produced by the recombination of three gene segments, $V_H$, D and $J_H$. In humans, there are approximately 51 functional $V_H$ segments (Cook and Tomlinson (1995) *Immunol Today*, 16: 237), 25 functional D segments (Corbett et al. (1997) *J. Mol. Biol.*, 268: 69) and 6 functional $J_H$ segments (Ravetch et al. (1981) *Cell*, 27: 583), depending on the haplotype. The $V_H$ segment encodes the region of the polypeptide chain which forms the first and second antigen binding loops of the $V_H$ domain (H1 and H2), whilst the $V_H$, D and $J_H$ segments combine to form the third antigen binding loop of the $V_H$ domain (H3). The $V_L$ gene is produced by the recombination of only two gene segments, $V_L$ and $J_L$. In humans, there are approximately 40 functional $V_H$ segments (Schäble and Zachau (1993) *Biol. Chem. Hoppe-Seyler*, 374: 1001), 31 functional $V_L$ segments (Williams et al. (1996) *J. Mol. Biol.*, 264: 220; Kawasaki et al. (1997) *Genome Res.*, 7:250), 5 functional $J_{kappa}$ segments (Hieter et al. (1982) *J. Biol. Chem.*, 257: 1516) and 4 functional $J_{lambda}$ segments (Vasicek and Leder (1990) *J. Exp. Med.*, 172: 609), depending on the haplotype. The $V_L$ segment encodes the region of the polypeptide chain which forms the first and second antigen binding loops of the $V_L$ domain (L1 and L2), whilst the $V_L$ and $J_L$ segments combine to form the third antigen binding loop of the $V_L$ domain (L3). Antibodies selected from this primary repertoire are believed to be sufficiently diverse to bind almost all antigens with at least moderate affinity. High affinity antibodies are produced by "affinity maturation" of the rearranged genes, in which point mutations are generated and selected by the immune system on the basis of improved binding.

Analysis of the structures and sequences of antibodies has shown that five of the six antigen binding loops (H1, H2, L1, L2, L3) possess a limited number of main-chain conformations or canonical structures (Chothia and Lesk (1987) *J. Mol. Biol.*, 196: 901; Chothia et al. (1989) *Nature*, 342: 877). The main-chain conformations are determined by (i) the length of the antigen binding loop, and (ii) particular residues, or types of residue, at certain key position in the antigen binding loop and the antibody framework. Analysis of the loop lengths and key residues has enabled us to the predict the main-chain conformations of H1, H2, L1, L2 and L3 encoded by the majority of human antibody sequences (Chothia et al. (1992) *J. Mol. Biol.*, 227: 799; Tomlinson et al. (1995) *EMBO J,* 14: 4628; Williams et al. (1996) *J. Mol. Biol.*, 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.*, 263: 800; Shirai et al. (1996) *FEBS Letters*, 399: 1.

Recently, the present inventors have devised a technique for the selection of immunoglobulins which are stable in an intracellular environment, are correctly folded and are functional with respect to the selective binding of their ligand within that environment. This is described in WO00/54057. In this approach, the antibody-antigen interaction method uses antigen linked to a DNA-binding domain as a bait and the scFv linked to a transcriptional activation domain as a prey. Specific interaction of the two facilitates transcriptional activation of a selectable reporter gene. An initial in-vitro binding step is performed in which an antigen is assayed for binding to a repertoire of immunoglobulin molecules. Those immunoglobulins which are found to bind to their ligand in vitro assays are then assayed for their ability to bind to a selected antigen in an intracellular environment, generally in a cytoplasmic environment.

The present inventors found that often, a significant number of those immunoglobulins which bind in vitro fail to bind specifically to their ligand in vivo. Therefore, there remains a need in the art for methods and procedures for predicting whether a given antibody will function within an intracellular environment.

SUMMARY OF THE INVENTION

The invention relates to a method for a priori identification of stable antibodies, capable of functioning as intracellular antibodies in reducing intracellular environments and for the design of libraries enriched with intracellular antibodies. In particular, the invention describes consensus sequences for intracellular antibodies (intrabody consensus sequences, ICS) that characterise the intracellular antibodies and the use of these ICS consensus sequences for the design and construction of libraries that are enriched with intracellular antibodies.

The presence of ICS sequences in an antibody is diagnostic of its property of being a functional intracellular antibody, without having to undertake experimental selection with IACT or intracellular expression in other systems, with a considerable saving of experimental work. The ICS sequence can be used for the optimisation of antibodies of interest, as well as for the design and construction of libraries that are enriched with intracellular antibodies.

Thus in a first aspect the present invention provides a method of identifying at least one consensus sequence for an intracellular antibody (ICS) comprising the steps of:

a) creating a database comprising sequences of at least a proportion of a variable heavy chain domain and/or variable light chain domain of validated intracellular antibodies (VIDA database) and aligning the sequences of the variable heavy chain domains or variable light chain domains of validated intracellular antibodies;

b) determining the frequency with which a particular amino acid occurs in each of the positions of the aligned antibodies;

c) selecting a frequency threshold value (LP or consensus threshold) in the range from 70% to 100%;

d) identifying the positions of the alignment at which the frequency of a particular amino acid is greater than or equal to the LP value;

e) identifying the most frequent amino acid, in the positions of the alignment defined in d).

According to the above aspect of the invention, advantageously the sequences of the variable heavy chain domains or variable light chain domains of validated intracellular antibodies present in the VIDA database are aligned according to Kabat.

As used herein, the term 'database' means any collection of data. Those skilled in the art will appreciate that there are many ways in which such data may be stored. Suitable methods include but are not limited to storage in electronic form and in paper form. Those skilled in the art will be aware of other suitable methods of data storage.

According to the present invention, the term 'creating' means generating or producing.

As used herein, the term "a proportion of a variable domain" means at least 20 contiguous amino acids of a heavy chain or light chain variable domain.

As herein defined, The VIDA database contains all the sequences of antibodies selected with IACT, in particular the sequences of the anti-TAU antibodies described herein. In addition, it comprises those antibodies reported in the literature to bind specifically to one or more antigen/ligand/s within an intracellular environment.

By 'aligning the (amino acid) sequences', it is meant that the (amino acid) sequences are arranged or lined up such that those amino acid residues which are the same or similar between the sequences are apparent. Thus 'aligning the sequences' as herein defined permits the simple and efficient comparison of the residue similarities and differences between two or more amino acid sequences. Sequences are advantageously aligned as set forth in Kabat, "Sequences of Proteins of Immunological Interest", US Department of Health and Human Services, using the Kabat numbering system which is known to those skilled in the art.

It should be appreciated that although reference is made throughout to the Kabat database, other databases of antibody sequences could be used as an alternative, or in addition to this database.

As used herein the term 'frequency' denotes the frequency (that is the number of times) with which a specific amino acid occurs in each of the residue positions of the aligned sequences. The % frequency means the percentage of identical amino acid residues at any given residue position in the sequence and is calculated as a percentage of the total number of amino acids at that position to be compared (that is the total number of sequences to be compared). Thus, for example, if 10 amino acid sequences are to be compared and at amino acid residue number 1, 7 out of 10 of the residues are arginines, then the percentage frequency of arginine at that position is 70%.

As used herein the term 'frequency threshold value' or 'LP' value refers to a selected minimum % frequency as herein defined for each amino acid position within the aligned sequences. Advantageously, the frequency threshold value or (LP) value selected is the same for each and every residue within the aligned sequences. The selection of a 'frequency threshold value' creates a cut-off point at each residue position for the allocation of a consensus residue at that position. That is, the % frequency of one or more identical amino acids at any given position is compared with the 'frequency threshold value' or (LP) value at that position, and if the % frequency of one or more identical or similar amino acids at any given residue position is at least the same as the selected frequency threshold value, then that residue will be assigned the 'consensus residue' for that residue position.

Those skilled in the art will appreciate that the higher the 'frequency threshold value' or 'LP value' selected, then the greater the '% frequency' (as herein defined) is required to be for a given residue at any given residue position, for it to be assigned a 'consensus residue' and hence part of the consensus sequence.

Analysis of the antibody sequences contained in VIDA makes it possible to identify a subset of the amino acid residues that are conserved in human and murine intracellular antibodies. This subset of residues is designated ICS (intrabody consensus sequence), and enables us to define an ICS for the VL chain and one for the VH chain for each species (human ICS-VH, human ICS-VL, mouse ICS-VH, mouse ICS-VL). Comparative analysis of the ICSs of different species for the same chain made it possible to identify the amino acids in common and therefore an ICS-VH hxm (man mouse) and an ICS-VL hxm, i.e. (minimum) general ICSs. Obviously the ICSs will be different depending on the threshold of homology between all the antibodies present in the VIDA database (absolute consensus, 90% consensus, etc.).

The present invention also provides a procedure for finding the optimum ICS for each reference group. The optimum ICS is obtained with an algorithm, described below, which changes the threshold of homology between the antibodies of the VIDA dataset iteratively and defines an optimum homology threshold.

Thus, in a further aspect the present invention provides a method of identifying at least one optimum consensus sequence for an intracellular antibody (optimum ICS) comprising the steps of:

a) identifying different ICSs for different LP values;

b) for each of said ICSs: constructing a frequency distribution of the number of identical amino acids between that particular ICS and each of the antibodies making up the VIDA database (VIDA distribution);

c) for each of the ICSS, constructing a frequency distribution of the number of identical amino acids between that particular ICS and each of the antibodies that make up the Kabat database (Kabat distribution);

d) defining a "distance" D between the VIDA distributions and the Kabat distribution corresponding to a value of LP;

e) for each LP value, determining the value of the "distance" D between the VIDA distributions and the Kabat distribution corresponding to that value of LP;

f) identifying the optimum ICS as the ICS corresponding to the value of LP for which the calculated value of the distance D defined in d) is maximum.

According to the above aspect of the invention, advantageously, the ICSs are generated according to one or more methods described herein.

Analysis of the antibody sequences contained in VIDA makes it possible to identify a subset of the amino acid residues that are conserved in human and murine intracellular antibodies. This subset of residues is designated ICS (intrabody consensus sequence), and enables us to define an ICS for the VL chain and one for the VH chain for each species (human ICS-VH, human ICS-VL, mouse ICS-VH, mouse ICS-VL). Comparative analysis of the ICSs of different species for the same chain made it possible to identify the amino acids in common and therefore an ICS-VH hxm (man mouse) and an ICS-VL hxm, i.e. (minimum) general ICSs. Obviously the ICSs will be different depending on the threshold of homology between all the antibodies present in the VIDA database (absolute consensus, 90% consensus, etc.).

A procedure is described for finding the optimum ICS for each reference group. The optimum ICS is obtained with an algorithm, described below, which changes the threshold of homology between the antibodies of the VIDA dataset iteratively and defines an optimum homology threshold.

Accordingly, an intracellular antibody is identified as an antibody that has an optimum ICS, defined as above, on the positions of the chain where the said ICS is defined, whereas hypotheses are not made regarding other positions, nor are constraints placed.

Comparison between the ICS and the Kabat consensus sequence (for the same group) shows that the ICS is highly homologous (but not completely identical) to the Kabat consensus, in those positions of the chain where the ICS itself is defined.

The ICS is used for predicting the property of any given antibody of being a functional intracellular antibody. In particular, the analysis described predicts that a percentage of about 10% of the antibodies present in the Kabat database are intracellular antibodies.

The ICS can be employed for constructing antibody libraries that are greatly enriched in functional intracellular antibodies. The libraries will preferably express scFv fragments based on ICS.

According to the above aspect of the invention, the term ICS denotes 'intracellular consensus sequence' and is a consensus sequence for an immunoglobulin molecule capable of binding to its ligand within an intracellular environment. ICS's as herein described are generated using the methods of the present invention. One skilled in the art will appreciate that the amino acid residues and their sequence comprising each ICS will depend upon the number of sequences compared in order to generate the ICS, the nature of the sequences compared and the frequency threshold value selected.

As herein described a 'VIDA' denotes a 'validated intracellularly binding antibody'. That is, it denotes an antibody which has been shown by functional studies to bind specifically to one or more ligands within an intracellular environment. VIDAs as herein defined include those antibodies which have been shown by the present inventors to function within an intracellular environment as well as those antibody molecules which are reported in the literature as binding to one or more ligands specifically within an intracellular environment.

Accordingly, a 'VIDA database' includes the sequences of those antibodies which have been shown by the present inventors to function within an intracellular environment as well as those antibody molecules which are reported in the literature as binding to one or more ligands specifically within an intracellular environment.

As used herein the term 'frequency distribution' refers to a representation of the relationship between two or more characteristics. Advantageously, the representation is a graphical representation. Specifically, the term 'VIDA distribution' of a particular ICS refers to a representation of the relationship between the number of identical amino acids between that particular ICS and each of the antibodies making up the VIDA database as herein defined.

Likewise the term 'Kabat' distribution of a particular ICS refers to a representation, preferably a graphical representation of the number of identical amino acids between that particular ICS and each of the antibodies which make up the Kabat database.

As defined herein, the 'D distance' is that graphically defined distance between a given VIDA (validated intracellular antibody) distribution value and a given Kabat distribution value for a given LP value (threshold value), as herein defined.

According to the present invention, the term 'optimum ICS' refers to the ICS (intracellularly binding antibody consensus sequence) corresponding to the LP (threshold value) for which the calculated distance D as herein defined is a maximum.

Advantageously, the consensus sequence is one of the consensus sequences for VH and/or $V_L$ comprising:

a) for a VH consensus sequence, at least the following amino acids in the positions indicated according to Chothia numbering (Chothia and Lesk, (1987) J. Mol. Biol. 196:910-917):

S-21, C-22, S-25, G-26, M-32, W-36, P-41, L-45, E-46, D-72, Q81, L-82c, E-85, D-86, A-88, Y-90, C-92, W-103, G-104, G-106, T-107, 1-110, V-111, S-112;

b) for a VL consensus sequence, at least the following amino acids in the positions indicated according to Chothia numbering:

G-16, C-23, W-35, G-57, G-64, S-65, S-67, 1-75, D-82, Y-86, C-88, T-102, K-103.

In a preferred embodiment of this aspect of the invention, the consensus sequence is for human VH and essentially comprises the following amino acids in the positions indicated according to Chothia numbering:

Q-1, V-2, Q-3, L-4, S-7,0-8, G-9, G10, V-12, P-14, G-15, S-17, L-18, R-19, L-20, S-21, C-22, A-24, S-25, G-26, F-27, T-28, F-29, Y-31a, M-32, W-36, R-38, Q-39, A-40, P-41, G-42, K-43, G-44, L-45, E-46, W-47, V-48, S-52, G-54, Y-58, Y-59, A-60, D-61, S-62, V-63, K-64, G-65, R-66, F-67, T-68, I-69, S-70, R-71, D-72, N-73, S-74, N-76, 1-77, L-80, Q81, M-82, L-82c, R-83, A-84, E-85, D-86, T-87, A-88, Y-90, C-92, A-93, W-103, G-104, G-106, T-107, L-108, V-109, 1-110, V-111, S-112, S-113;

In a further preferred embodiment, the consensus sequence represents human VL, and essentially comprises the following amino acids in the positions indicated according to Chothia numbering:

T-5, P-8, G-16, 1-21, C-23, W-35, Y-36, Q-37, P-40, G-41, P-44, I-48, S-56, G-57, S-63, G-64, S-65, S-67, G-68, L-73, T-74, 1-75, D-82, A-84, Y-86, C-88, T-102, K-103.

In an especially preferred embodiment of this aspect of the invention an immunoglobulin of the present invention comprises a consensus sequence which comprises the following amino acids in the positions indicated according to Chothia numbering:

Q-1, V-2, Q-3, L-4, S-7, G-8, G-9, G10, V-12, P-14, G-15, S-17, L-18, R-19, L-20, S-21, C-22, A-24, S-25, G-26, F-27, T-28, F-29, Y-31a, M-32, W-36, R-38, Q-39, A-40, P-41, G-42, K-43, G-44, L-45, E-46, W-47, V-48, S-52, G-54, Y-58, Y-59, A-60, D-61, S-62, V-63, K-64, G-65, R-66, F-67, T-68, 1-69, S-70, R-71, D-72, N-73, S-74, N-76, T-77, L-80, Q81, M-82, L-82c, R-83, A-84, E-85, D-86, 1-87, A-88, Y-90, C-92, A-93, W-103,

G-104, G-106, T-107, L-108, V-109, T-110, V-111, S-112, S-113 and a variable light chain which comprises the following amino acids in the positions indicated according to Chothia numbering:

T-5, P-8, G-16, I-21, C-23, W-35, Y-36, Q-37, P-40, G-41, P-44, I-48, S-56, G-57, S-63, G-64, S-65, S-67, G-68, L-73, T-74, 1-75, D-82, A-84, Y-86, C-88, T-102, K-103.

As used herein, the term “enriched” means that the concentration or proportion of molecules having a particular desired characteristic, e.g., intracellular binding capacity, is higher in a selected population than in a population not selected for that characteristic. The concentration or proportion of molecules with a desired characteristic is at least 10% higher in an “enriched” population than in one that is not enriched, preferably 20% higher, 30% higher, 40% higher, 50% higher, 75% higher, 100% higher (2-fold), 5-fold higher, 10-fold higher or more.

In a further aspect the present invention provides an intracellularly binding immunoglobulin molecule comprising at least one variable chain which is described by at least one of the consensus sequences described in FIGS. 11*a* and 11*b* and depicted SEQ ID no 41 and 42 respectively.

Advantageously, an immunoglobulin molecule of the present invention comprises, (a) for the heavy chain, at least the following amino acids in the positions indicated according to Chothia numbering (Chothia and Lesk, (1987) J. Mol. Biol. 196:910-917): S-21, C-22, S-25, G-26, M-32, W-36, P-41, L-45, E-46, D-72, Q81, L-82c, E-85, D-86, A-88, Y-90, C-92, W-103, G-104, G-106, T-107, T-110, V-111, S-112; and (b) for the light chain at least the following amino acids in the positions indicated according to Chothia numbering:

G-16, C-23, W-35, G-57, G-64, S-65, S-67, 1-75, D-82, Y-86, C-88, T-102, K-103.

In a further aspect still, the present invention provides the use of an immunoglobulin molecule comprising at least one consensus sequence described in FIG. 11*a* and/or 11*b* and depicted SEQ 41 and SEQ 42 respectively in the selective binding of a ligand within an intracellular environment.

As herein defined, the term ‘selective binding’ (of a ligand within an intracellular environment) means that the interaction between the immunoglobulin and the ligand are specific, that is, in the event that a number of molecules are presented to the immunoglobulin, the latter will only bind to one or a few of those molecules presented. Advantageously, the immunoglobulin ligand interaction will be of high affinity. The interaction between immunoglobulin and ligand will be mediated by non-covalent interactions such as hydrogen bonding and Van der Waals interactions. Generally, the interaction will occur in the cleft between the heavy and the light chains of the immunoglobulin.

In a further aspect still, the present invention provides a method for predicting whether an antibody is a functioning intracellular antibody comprising the steps of:

a) aligning the sequence of the antibody with the sequences of the antibodies of the reference VIDA database;

b) aligning the sequence of the antibody with the optimum ICS sequence of the reference VIDA database;

c) constructing VIDA and KABAT distributions corresponding to the optimum value of LP (frequency threshold value);

d) determining the corresponding distance D;

e) determining the identity number N between the sequence of the antibody and the ICS reference sequence;

f) calculating the difference between the mean value of the VIDA distribution and the product between D and the standard deviation of the VIDA distribution, obtaining the parameter $S_{intra}$;

g) if the identity number N is greater than or equal to $S_{intra}$, identifying the antibody as intracellular antibody.

In a further aspect the present invention provides a method for conferring upon an immunoglobulin molecule the ability to function within an intracellular environment, comprising the steps of:

a) identifying the optimum ICS reference sequence b) optionally, modifying, by site-specific mutagenesis, the amino acid residues that are located in the positions defined by the optimum ICS, or a subset of these residues, in such a way that they are those identified by the optimum ICS.

According to this aspect of the invention, advantageously the aligning step is performed as described herein. Advantageously, the ICS generation is performed using the methods herein described.

The present inventors have found that by performing a functional binding assay (that is by performing a yeast two-hybrid based IACT assay) to all of the antibodies proposed to be included in a database, and only using those antibodies which are found using to IACT to bind specifically to antigen within such an environment when generating consensus sequences, then more complete consensus sequence/s for the antibody variable domains may be obtained.

Thus, in a further aspect, the present invention provides a method for identifying at least one consensus sequence for an intracellular antibody (ICS) comprising the steps of:

(a) selecting and aligning the sequences of antibody light or heavy chain variable regions which are shown using IACT to bind specifically to antigen/ligand within an intracellular environment, and (b) identifying the most frequent amino acid, in each position of the alignment.

Advantageously, the consensus sequence/s identified using the method of this aspect of the invention are those described in FIG. 5a and depicted SEQ 3 and 4. The consensus sequence/s identified using the above listed approach share all of the amino acids present within the less complete consensus sequence shown in FIGS. 11a and 11b and identified as SEQ no 41 and 42, which use the VIDA database (which includes those antibodies reported in the literature to bind to their ligand/antigen within an intracellular environment, and which have not necessarily been shown by IACT to do so). Details of this approach are given in strategy A, Example 10.

In a further aspect still, the present invention provides a method for selecting one or more antibodies capable of binding specifically to its one or more antigens/ligands within an intracellular environment comprising the steps of:

(a) comparing at least a proportion of the variable heavy chain of one or more antibodies with at least the consensus sequence shown in FIG. 5a and depicted SEQ 3, and (b) selecting those one or more antibodies whose variable heavy chain is at least 85% identical with the consensus sequence of step (a).

In yet a further aspect, the present invention provides a method for selecting one or more antibodies capable of binding specifically to its one or more antigens/ligands within an intracellular environment comprising the steps of:

(a) comparing at least a proportion of the variable light chain of one or more antibodies with at least the consensus sequence shown in FIG. 5a and depicted SEQ 4, and (b) selecting those one or more antibodies whose variable light chain is at least 85% identical with the consensus sequence of step (a).

According to the above aspects of the invention, advantageously, the intracellular environment is a mammalian intracellular environment. More advantageously, the mammal is a human being.

Advantageously, a further in vivo binding step (c) is performed in order to test whether the selected one or more antibodies binds specifically to their one or more antigens. Advantageously, this in vivo binding step is performed using IAC technology described herein and detailed in WO 000/54057.

According to the above aspects of the invention, advantageously, the immunoglobulin has a $V_H$ amino acid sequence which shows at least 86% identity with the VH consensus sequence identified by SEQ ID no 3 and shown in FIG. 5. In an especially preferred embodiment, the immunoglobulin molecule shows at least 87% identity. Advantageously the immunoglobulin has a VH amino acid sequence which shows at least 88% identity, 89% identity, 90% identity or 91, 92, 93, 94, 95, 96, 97, 98% identity with the VH consensus sequence identified by SEQ ID no 3. Most advantageously, the immunoglobulin has a VH amino acid sequence which shows at least 99% identity with the VH consensus identified by SEQ ID No 3 and shown in FIG. 5. In a most preferred embodiment it shows at least 100% identity with the VH consensus sequence depicted by SEQ ID no 3 and shown in FIG. 5.

In a preferred embodiment of the above aspects of the invention, both the variable light chain and the variable heavy chains of the antibodies for selection are be compared with the consensus sequences as detailed above.

One skilled in the art will appreciate that, the greater the degree of identity the variable light and/or variable heavy chain of the antibody whose intracellular binding ability is to be determined is to the one or more consensus sequences shown in FIG. 5a, then the greater the probability that the antibody in question will be capable of binding specifically to its ligand within an intracellular environment. In addition, the IACT based binding step provides further guidance on whether the antibody in question will be capable of binding selectively to its ligand within a mammalian intracellular environment.

In a further aspect still, the present invention provides an intracellularly binding immunoglobulin molecule comprising a variable heavy chain which exhibits 85% homology to the consensus sequence shown in FIG. 5a and depicted as SEQ ID No 3 and at least one variable light chain.

According to the above aspect of the invention, advantageously, the immunoglobulin molecule comprises a heavy chain variable domain (VH) which is a member of the VHIII subgroup of immunoglobulin heavy chains.

In yet a further aspect, the present invention provides an intracellularly binding immunoglobulin molecule comprising a variable light chain which exhibits 85% homology to the consensus sequence shown in FIG. 5a and depicted as SEQ ID No 4 and at least one variable heavy chain.

In a further aspect still, the present invention provides the use of an immunoglobulin molecule comprising at least one variable heavy chain domain (VH) exhibiting at least 85% identity with the consensus sequence shown in FIG. 5a and depicted SEQ 3, and at least one light chain domain (VL), in the selective binding of a ligand within an intracellular environment.

In a preferred embodiment of the above aspect of the invention, the use is of an immunoglobulin molecule comprising at least one heavy chain variable domain ($V_H$) which is a member of the VHIII subgroup of immunoglobulin heavy chains, in the selective binding of a ligand within an intracellular environment.

In a further preferred embodiment of the above aspect of the invention the use is of an immunoglobulin molecule comprising at least one light chain variable domain ($V_L$) which is a member of the $V_K$I subgroup of immunoglobulin light chains, in the selective binding of a ligand within an intracellular environment.

The present inventors realised that using the knowledge of the consensus sequences for intracellular antibodies, then libraries may be generated which are enriched in antibody molecules or fragments thereof which are capable of functioning within an intracellular environment.

Thus in a further aspect, the present invention provides a library, wherein the library is generated using any one or more of the variable heavy domain amino acid sequences (VH) selected from the group consisting of: a VH amino acid sequence showing at least 85% identity with the consensus sequence depicted as SEQ 3 and shown in FIG. 5a, a VH sequence which is described by the consensus sequence depicted in SEQ 41 and shown in FIG. 11a, According to the above aspect of the invention, advantageously, the immunoglobulin has a $V_H$ amino acid sequence which shows at least 86% identity with the VH consensus sequence identified by SEQ ID no 3 and shown in FIG. 5. In an especially preferred embodiment, the immunoglobulin molecule shows at least 87% identity. Advantageously the immunoglobulin has a VH amino acid sequence which shows at least 88% identity, 89% identity, 90% identity or 91, 92, 93, 94, 95, 96, 97, 98% identity with the VH consensus sequence identified by SEQ ID no 3. Most advantageously, the immunoglobulin has a VH amino acid sequence which shows at least 99% identity with the VH consensus identified by SEQ ID No 3 and shown in FIG. 5. In a most preferred embodiment it shows at least 100% identity with the VH consensus sequence depicted by SEQ ID no 3 and shown in FIG. 5.

Thus, in a further aspect the present invention provides a method for the construction of an antibody library enriched with antibodies capable of functioning within an intracellular environment comprising the steps of:

a) selecting an antibody framework from those that are intracellularly functionally stable, from the Kabat database;

b) on each framework, mutagenizing the amino acids present in the positions of the sequence defined by the optimum ICS according to the invention, changing them into the amino acid residue that is located in that position in the ICS sequence; and c) on each of the frameworks, randomising the CDR regions of the antibody sequence.

According to the above aspect of the invention, the term 'intracellularly functionally stable' (antibodies) refers to those antibodies which are capable of functioning within an intracellular environment, that is, those antibodies which are stable with respect to specific antigen binding and advantageously eliciting an immune response.

As herein described the term 'mutagenizing' (one or more amino acid residues) refers to a change of one or more amino acid residues. Such change may involve a substitution, deletion, inversion or an insertion. Advantageously, the 'mutagenizing' as herein described involves a substitution. Methods for 'mutagenizing' amino acid sequences will be familiar to those skilled in the art and are described herein.

Furthermore, according to the present invention, the term 'randomising' (one or more CDR regions) means to 'shuffle', rearrange or otherwise change by amino acid insertion, deletion or substitution some or all the amino acid residues comprising those one or more CDR regions so as to create a repertoire of immunoglobulin molecules sharing a common framework region and comprising CDR regions which comprise the same amino acid constituents as the other immunoglobulin molecules within the library but wherein the identity of at least some of those residues differs between the individual immunoglobulin molecules. Those skilled in the art will appreciate that the randomisation of CDR residues enables the generation of libraries comprising immunoglobulin molecules having a number of different antigen binding specificities.

According to the above aspects of the invention, preferably the ICSs are generated according to the methods described herein.

In yet a further aspect, the present invention provides a method for the construction of an antibody library enriched with functional intracellular antibodies capable of functioning within an intracellular environment, comprising the steps of:

a) selecting an antibody framework, on the basis of the homology with an optimum ICS sequence;

b) mutagenizing all the remaining residues of the antibody framework, limited, for each position, to the amino acids that are located, in that position, in antibodies of the Kabat database; and c) on each of the frameworks, randomising the CDR regions of the antibody sequence, In the above aspect of the invention, advantageously an antibody framework is selected on the basis of maximal homology with an optimum ICS sequence according to the invention. That is, a framework region is selected which shows maximum homology with an ICS generated according to the present invention.

In a final aspect, the present invention provides the use of a library as herein described for producing immunoglobulin molecules, wherein a substantial proportion of those molecules expressed are capable of selectively binding to a ligand within an intracellular environment.

Definitions

Immunoglobulin molecules, according to the present invention, refer to any moieties which are capable of binding to a target. In particular, they include members of the immunoglobulin superfamily, a family of polypeptides which comprise the immunoglobulin fold characteristic of antibody molecules, which contains two beta sheets and, usually, a conserved disulphide bond.

Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The present invention is applicable to all immunoglobulin superfamily molecules which are capable of binding to target molecules. Preferably, the present invention relates to antibodies or scFv molecules.

Antibodies as used herein, refers to complete antibodies or antibody fragments capable of binding to a selected target, and including Fv, scFv, Fab' and F(ab')$_2$, monoclonal and polyclonal antibodies, engineered antibodies including chimeric, CDR-grafted and humanised antibodies, and artificially selected antibodies produced using phage display or alternative techniques.

Small fragments, such as Fv and scFv, possess advantageous properties for diagnostic and therapeutic applications on account of their small size and consequent superior tissue distribution. Preferably, the antibody is a single chain antibody or scFv.

Heavy chain variable domain refers to that part of the heavy chain of an immunoglobulin molecule which forms part of the antigen binding site of that molecule. The VHIII subgroup describes a particular sub-group of heavy chain variable regions (the VHIII). Generally immunoglobulin molecules having a variable chain amino acid sequence falling within this group possess a VH amino acid sequence which can be described by the VHIII consensus sequence in the Kabat database.

Light-chain variable domain refers to that part of the light chain of an immunoglobulin molecule which forms part of the antigen binding site of that molecule. The VkI subgroup of immunoglobulin molecules describes a particular sub-group of variable light chains. Generally immunoglobulin molecules having a variable chain amino acid sequence falling within this group possess a VL amino acid sequence which can be described by the $V_K I$ consensus sequence in the Kabat database.

Framework region of an immunoglobulin heavy and light chain variable domain. The variable domain of an immunoglobulin molecule has a particular three-dimensional conformation characterised by the presence of an immunoglobulin fold. Certain amino acid residues present in the variable domain are responsible for maintaining this characteristic immunoglobulin domain core structure. These residues are known as framework residues and tend to be highly conserved.

CDR (complementarity determining region) of an immunoglobulin molecule heavy and light chain variable domain describes those amino acid residues which are responsible for the specificity antigen binding, and are as defined by Kabat (op. Cit.). The CDR residues are mainly, but not exclusively, contained within the hypervariable loops of the variable regions as defined by Chothia and Lesk (op. cit). The CDRs and the hypervariable loops are directly involved with the interaction of the immunoglobulin with the ligand. Residues within these loops tend to show a lower degree of conservation than those in the framework region.

Intracellular means inside a cell, and the present invention is directed to those immunoglobulins which will bind to ligands/targets selectively within a cell. The cell may be any cell, prokaryotic or eukaryotic, and is preferably selected from the group consisting of a bacterial cell, a yeast cell and a higher eukaryote cell. Most preferred are yeast cells and mammalian cells. As used herein, therefore, "intracellular" immunoglobulins and targets or ligands are immunoglobulins and targets/ligands which are present within a cell. In addition the term 'Intracellular' refers to environments which resemble or mimic an intracellular environment. Thus, "intracellular" may refer to an environment which is not within the cell, but is in vitro. For example, the method of the invention may be performed in an in vitro transcription and/or translation system, which may be obtained commercially, or derived from natural systems.

The KABAT database is an exhaustive collection of antibody sequences on which a sequence of interest can be tested for discovering its characteristics (subgroup to which it belongs, position of each amino acid residue, variability (http://immuno.bme.nwu.edu) (Johnson, G. et al. 2000). This database also contains citations from scientific journals and links to the PubMed archive of scientific information. Using the Kabat database, it is possible to obtain a diagram of the distribution of the amino acids in the subgroups to which they belong. It is also possible to obtain a distribution of the residues in each position of the sequence tested and hence obtain its variability.

Consensus sequence of $V_H$ and $Y_L$ chains in the context of the present invention refers to the consensus sequences of those $V_H$ and $V_L$ chains from immunoglobulin molecules which can bind selectively to a ligand in an intracellular environment. The residue which is most common in any one given position, when the sequences of those immunoglobulins which can bind intracellularly are compared is chosen as the consensus residue for that position. The consensus sequence is generated by comparing the residues for all the intracellularly binding immunoglobulins, at each position in turn, and then collating the data. In this case the sequences of 11 immunoglobulins was compared. In the context of the present invention, a consensus residue is only conferred if a residue occurred greater than 5 times at any one position. For the avoidance of doubt, the terms VH and VL consensus sequences does not include the sequences of the J regions. In addition, the first two residues (methionine and alanine) are not part of the consensus. They are derived from an NCII restriction site.

As herein defined, The VIDA database contains all the sequences of antibodies selected with IACT, in particular the sequences of the anti-TAU antibodies described. In addition, it comprises those antibodies reported in the literature to bind specifically to one or more antigen/ligand/s within an intracellular environment. A 'validated intracellular antibody' as herein described refers to those antibodies which are found using IACT or reported in the literature to be functional within an intracellular environment. By the term 'functional' it is meant that those validated antibodies are capable of binding selectively to their specific antigen within such an environment.

The term 'frequency threshold value' or 'LP' value refers to a selected minimum % frequency as herein defined for each amino acid position within the aligned sequences. Advantageously, the frequency threshold value or (LP) value selected is the same for each and every residue within the aligned sequences. The selection of a 'frequency threshold value' creates a cut-off point at each residue position for the allocation of a consensus residue at that position. That is, the % frequency of one or more identical amino acids at any given position is compared with the 'frequency threshold value' or (LP) value at that position, and if the % frequency of one or more identical or similar amino acids at any given residue position is at least the same as the selected frequency threshold value, then that residue will be assigned the 'consensus residue' for that residue position.

$$P_s \; P_s = \sqrt[n]{\prod_{i=1}^{n} P_i(A_{s,i})}$$

Selective binding in the context of the present invention, means that the interaction between the immunoglobulin and the ligand are specific, that is, in the event that a number of molecules are presented to the immunoglobulin, the latter will only bind to one or a few of those molecules presented. Advantageously, the immunoglobulin ligand interaction will be of high affinity. The interaction between immunoglobulin and ligand will be mediated by non-covalent interactions such as hydrogen bonding and Van der Waals. Generally, the interaction will occur in the cleft between the heavy and the light chains of the immunoglobulin.

A repertoire in the context of the present invention refers to a set of molecules generated by random, semi-random or directed variation of one or more template molecules, at the nucleic acid level, in order to provide a multiplicity of binding specificities. In this case the template molecule is one or more of the VH and/or VL domain sequences herein described. Methods for generating repertoires are well characterised in the art.

A library according to the present invention refers to a mixture of polypeptides or nucleic acids. The library is composed of members. Sequence differences between library members are responsible for the diversity present in the library. The library may take the form of a simple mixture of polypeptides or nucleic acids, or may be in the form organisms or cells, for example bacteria, viruses, animal or plant cells and the like, transformed with a library of nucleic acids. Typically, each individual organism or cell contains only one member of the library. In certain applications, each individual organism or cell may contain two or more members of the library. Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member.

(B) The specificity of interaction of the isolated scFv was verified by using a-gal bait (pM-β-gal) instead of BCR-ABL antigen bait in the same CHO assay system, as indicated. The normalised Firefly luciferase level for scFvF8 was taken as 1 and the (C) relative luciferase level for each BCR-specific scFv was shown in the histogram.

FIG. 5 shows the Alignment of derived protein sequences of intracellular scFv. The nucleotide sequences of the scFv were obtained and the derived protein translations (shown in the single letter code) were aligned. The complementarity determining regions (CDR) are shaded. Framework residues for SEQ no 1 to 40 are those which are underlined. The consensus sequence at a specific position was calculated for the most frequently occurring residue but only conferred if a residue occurred greater than 5 times at that position.

A. Sequences of VH and VL from anti-BCR (designated as B3-B89) and anti-ABL (designated as A5-A32). The combined consensus (Con) of the anti-BCR and ABL ICAbs is indicated compared with the subgroup consensuses for VH3 and $V_K$I from the Kabat database.

Represents sequence identity with the intracellular antibody binding $V_H$ or $V_L$ consensus (SEQ 3 and SEQ 4)

represents gaps introduced to optimise alignment

B. A sequence comparison of randomly obtained scFv obtained from the unselected phage display library. The consensuses obtained from the randomly isolated scFv (rcH and rcL) are indicated.

represents gaps introduced to optimise alignment

X represents positions at which no consensus could be assigned.

Figure 6:
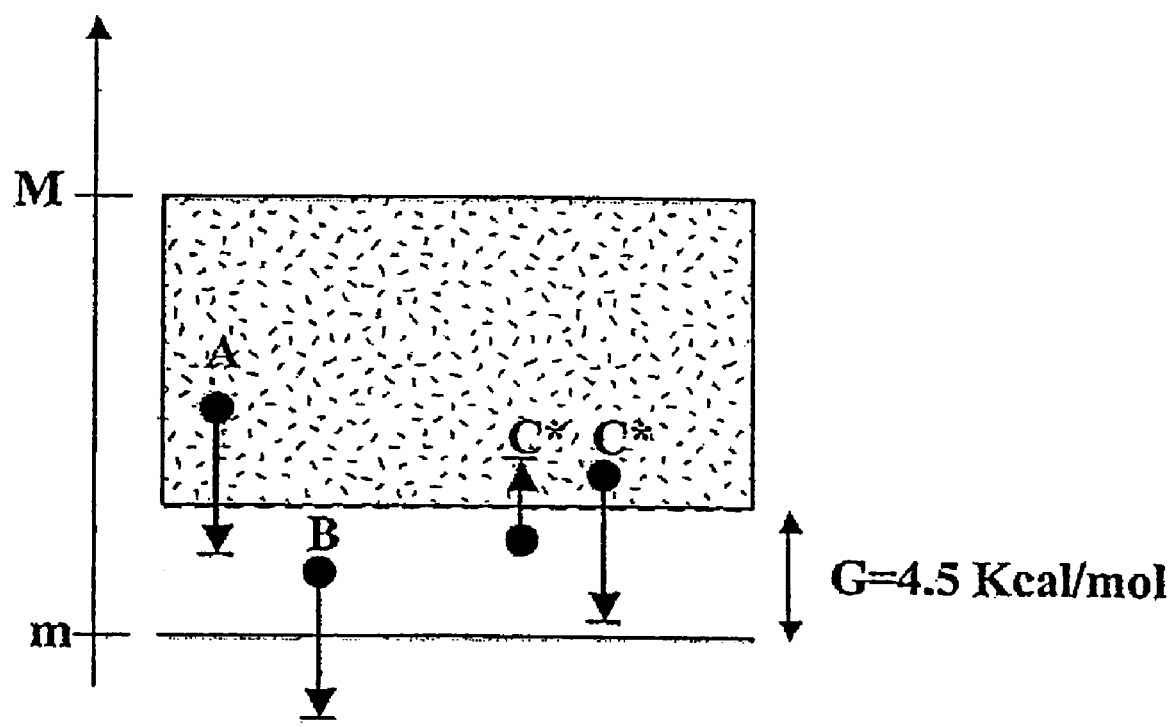

FIG. 6. Schematic diagram of folding, stability and tolerance to removal of the disulphide bridges of the scFvs.

Figure 7:
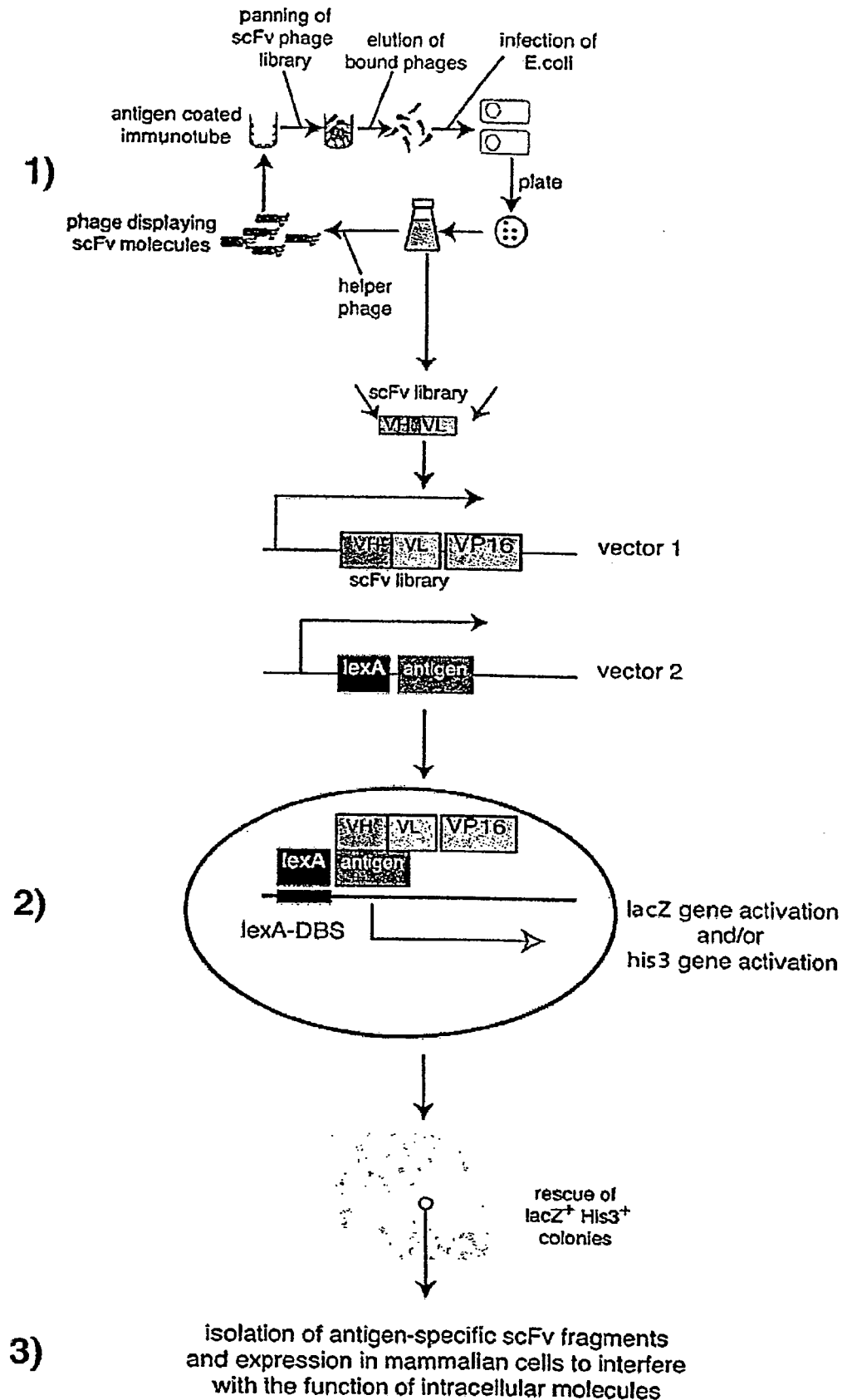

FIG. 7. Schematic diagram of IACT technology. IACT is a combination of the double hybrid system and phage display technology. Initially, phage display technology is used for increasing the percentage of antibody fragments that are specific to the protein used as "bait".

The double hybrid system is adapted so as to be able to isolate pairs of antigens and associated specific antibody fragments in conditions of intracellular expression. After selection in vivo, the clones that proved to be positive are isolated and the scFvs can be used for applications in vitro and in vivo.

Figure 8:
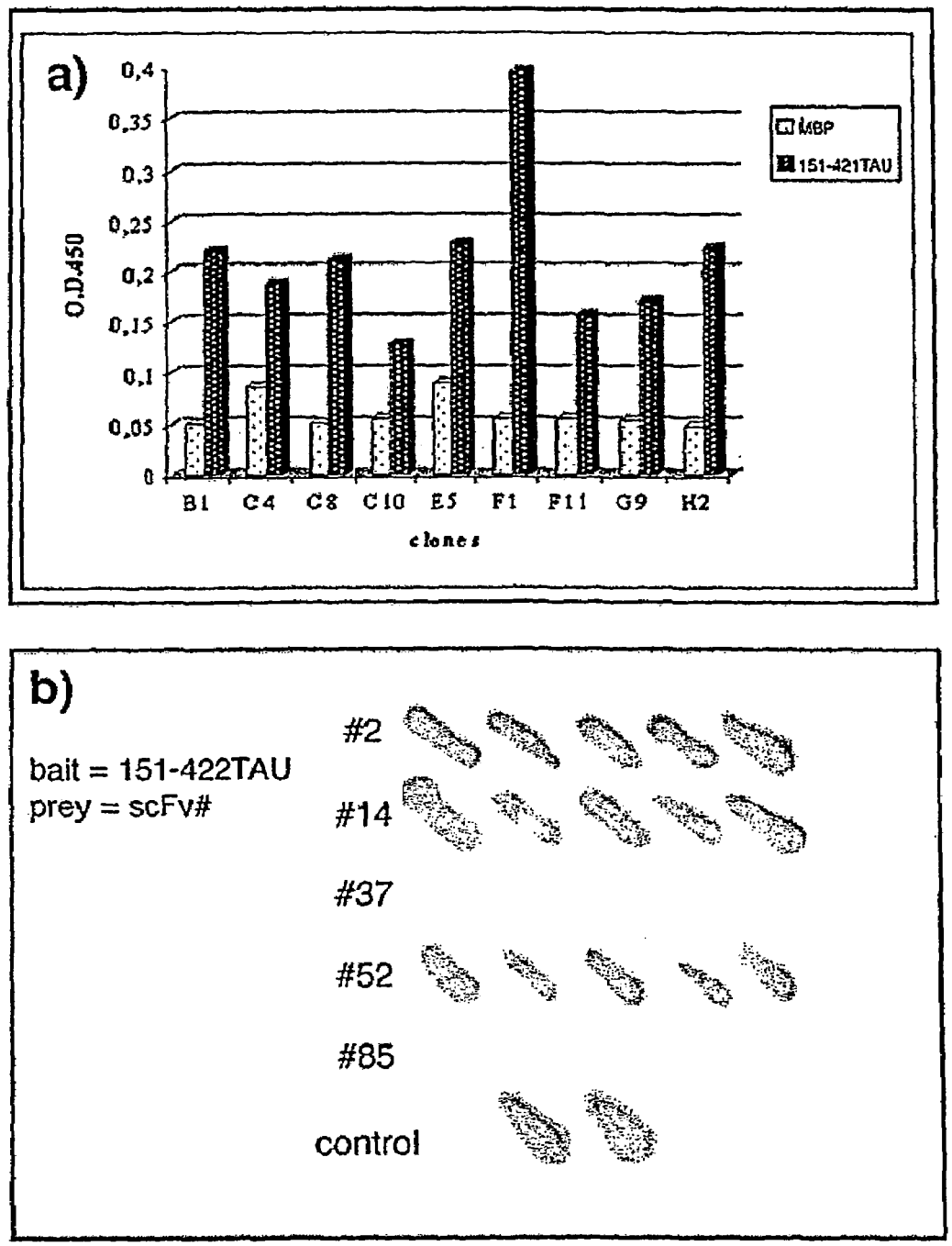
Figure 8:
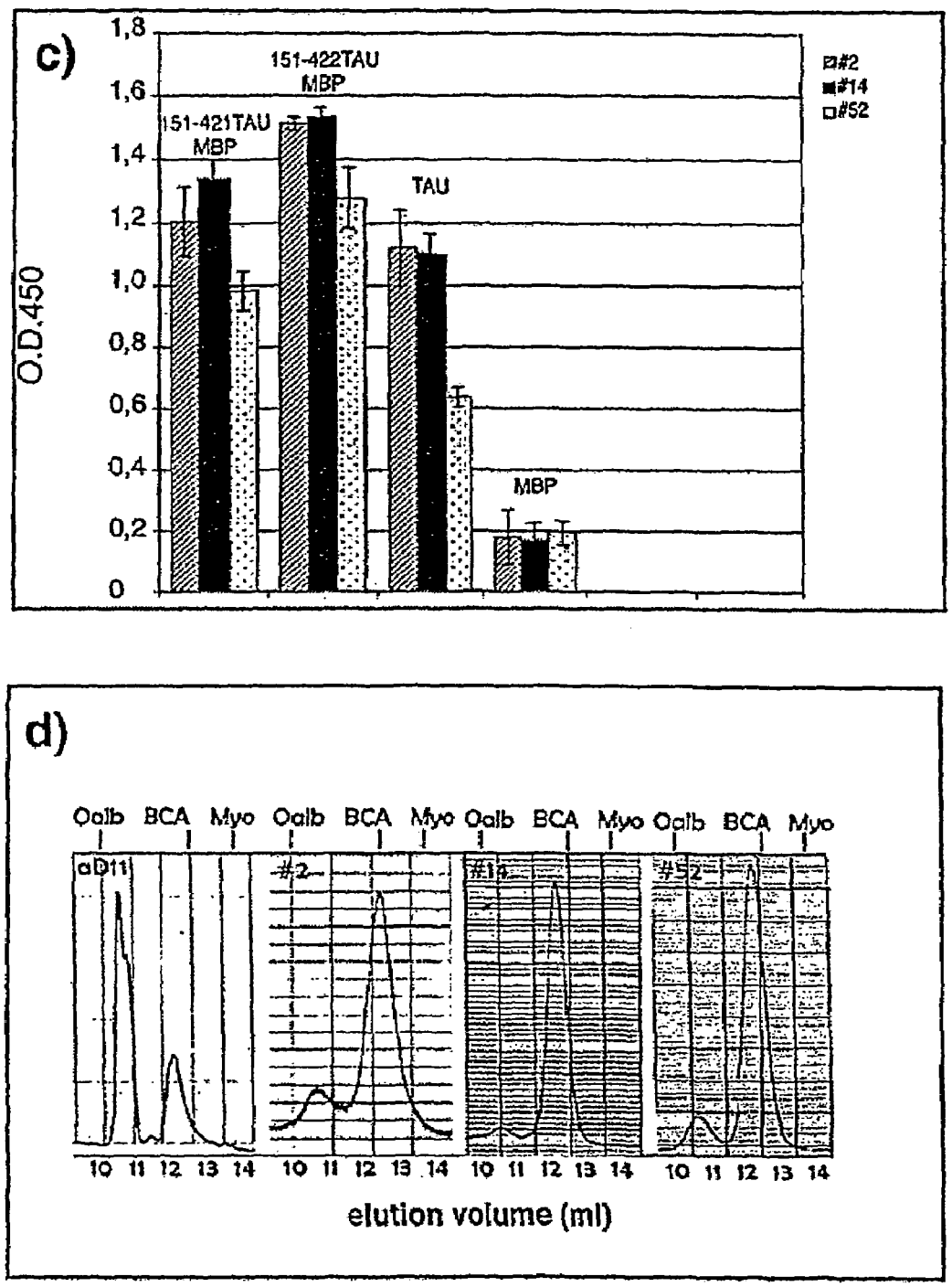

FIG. 8. a) Results obtained in ELISA from phages isolated after the second cycle of preselection in vitro. The antigens were preadsorbed on the plate at a concentration of 10 µg/ml. Only 9 scFvs out of 96 tested turned out to be specific for the TAU protein 151-421. The specificity of the bond was compared with the signal obtained in ELISA from the same scFvs tested against other antigens, in particular against MBP protein, used for purification of the TAU fragment used for preselection in vitro. b) Interaction in vivo between the bait used (lexA-TAU-151-422) and a panel of scFvs isolated using IACT. Only scFv #2, #14 and #52 were capable of transactivating the reporter genes HIS3 and lacZ (first, second and fourth line) in contrast to the scFvs #37 and #85 (third and fourth line). The interaction pair scFvF8+AMCVp41 was used as positive control (Visintin, M. et al. 1999) (sixth line). c) Soluble fractions of scFv #2, #14 and #52 extracted from the periplasmic space of E. coli were assayed in ELISA. The antigens were preadsorbed on the plate at a concentration of 10 µg/ml. The ELISA signals were measured at OD 450. d) Gel filtration chromatogram with Superdex-75 analytical column, of scFv #2, #14, #52 and scFvαD11. The elution volumes and the masses of the proteins used as markers are shown in the diagram: Ovalbumin (Oalb) (45 kDa), Bovine Carbonic Anhydrase (BCA) (29 kDa), Myosin (Myo) (17 kDa). The scFv in monometric form flowed at about 12 ml. As a representative example, the chromatogram of a gel filtration analysis of scFvαD11 shows that the elution peaks of dimeric or polymeric species (aggregates) are eluted after about 10.5 ml.

Figure 9:
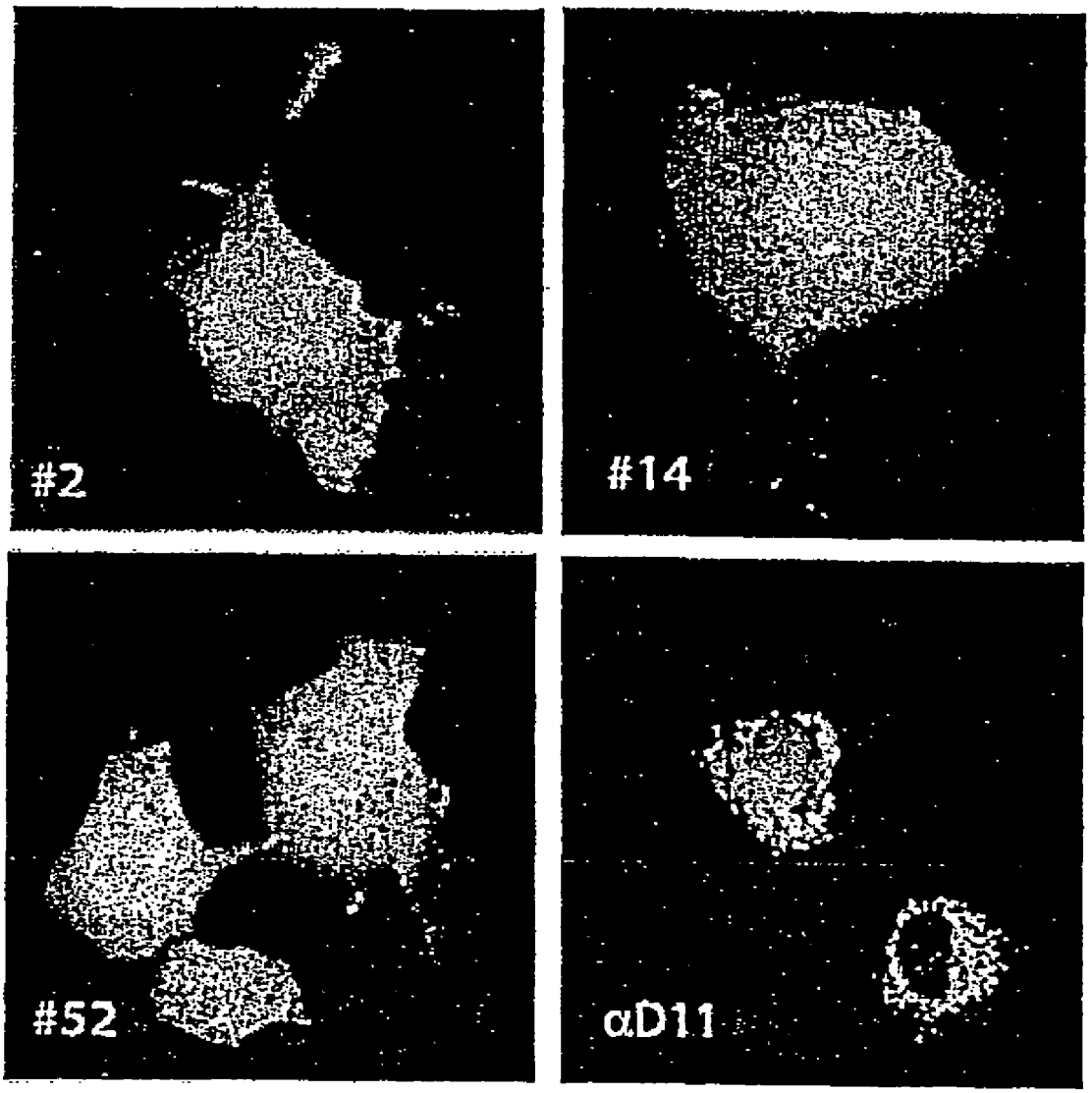

FIG. 9. Immunofluorescence microscopy of the anti-TAU isolated with IACT (scFv #2, #14 and #52) and of the control scFvαD11. The scFvs are expressed in the cytoplasm of the COS fibroblasts. The cells were treated with an anti-myc tag antibody (Evan, G. I. et al. 1985), followed by incubation with a fluoresceinated anti-mouse monoclonal antibody (vector).

Figure 10:
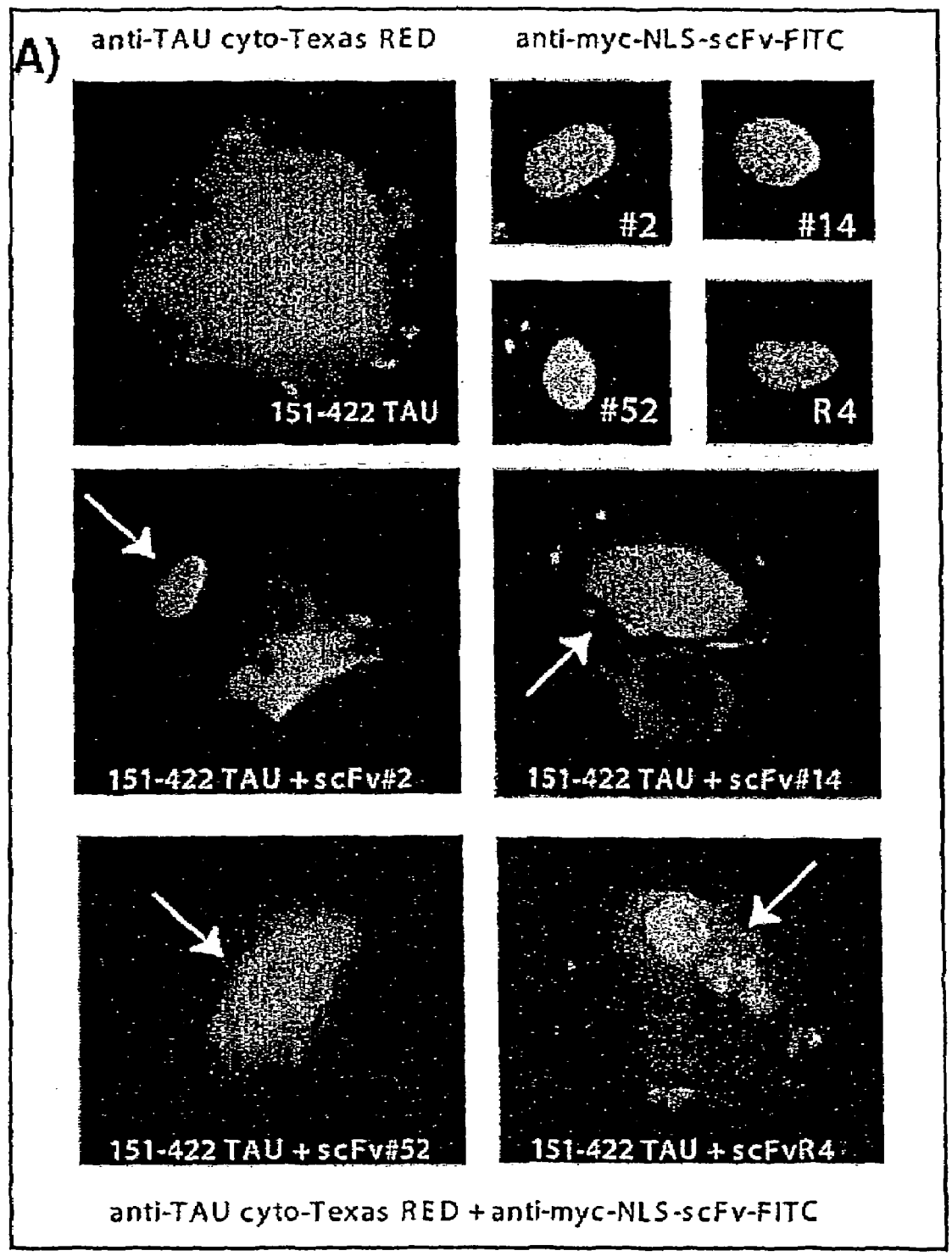
Figure 10:
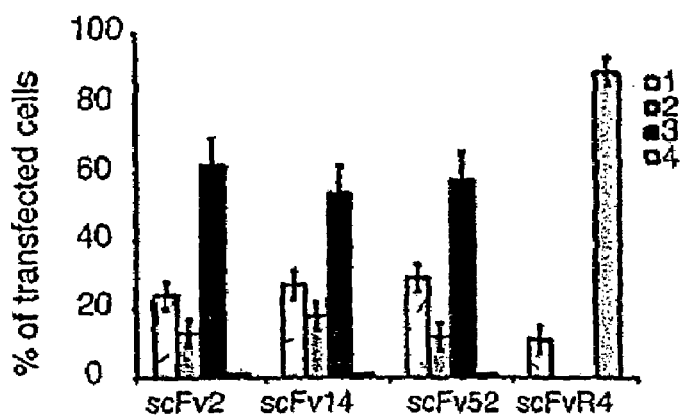
Figure 10:
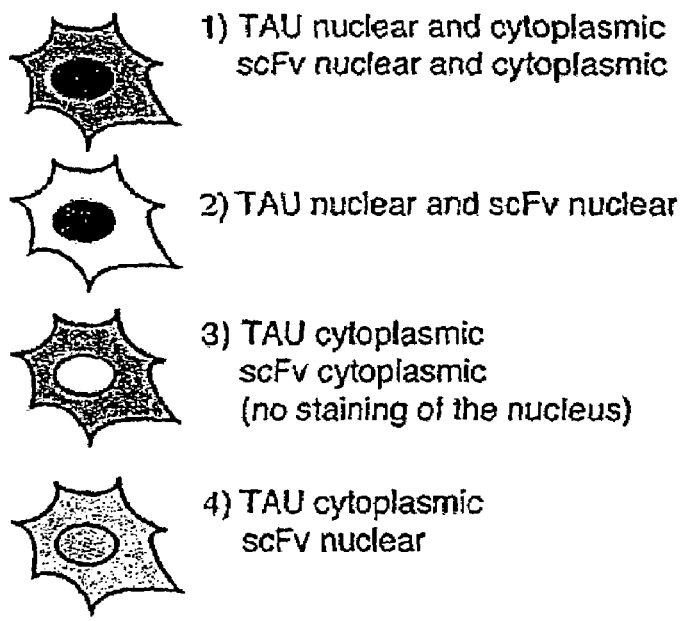

FIG. 10. A) Double immunofluorescence. The mislocalizations of TAU in the presence of the scFv-anti-TAU in the CHO cells were analysed. Marking of TAU (expressed in the cytoplasm) was effected using a (monoclonal) anti-TAU 7.51 antibody and using, as secondary antibody, an anti-mouse antibody conjugated with Texas-RED (stains red). Transfection of the scFvs (scFv #2, #14 and #52) and scFvR4 (Martineau, P. et al. 1998) cloned in a nuclear expression vector, was detected with the anti-myc tag 9E10 (Evan, G. I. et al. 1985) followed by the fluoresceinated anti-mouse secondary antibody (vector). The co-expression of the scFvs together with TAU was analysed using an anti-TAU antibody (7.51) followed by an anti-mouse secondary antibody marked with Texas-RED (for localising TAU) and using a polyclonal antibody anti-myc tag, recognised in its turn by a fluoresceinated anti-rabbit. The cotransfected cells were visualised in the microscope using a variable wavelength filter (Zeiss Filter Set 25). The arrows indicate colocalization of the scFv-anti-TAU and of TAU in the nucleus. B) and C) Effect of retargeting of TAU in the CHO cells by scFv #2, #14, #52 and the control R4. The pattern of staining of TAU and of the scFvs in the cotransfected cells was subdivided into four classes, in accordance with analysis of the frequency observed for each group. Patterns 1), 2) and 3) are indicative of interaction between TAU and a scFv.

Figure 11C:
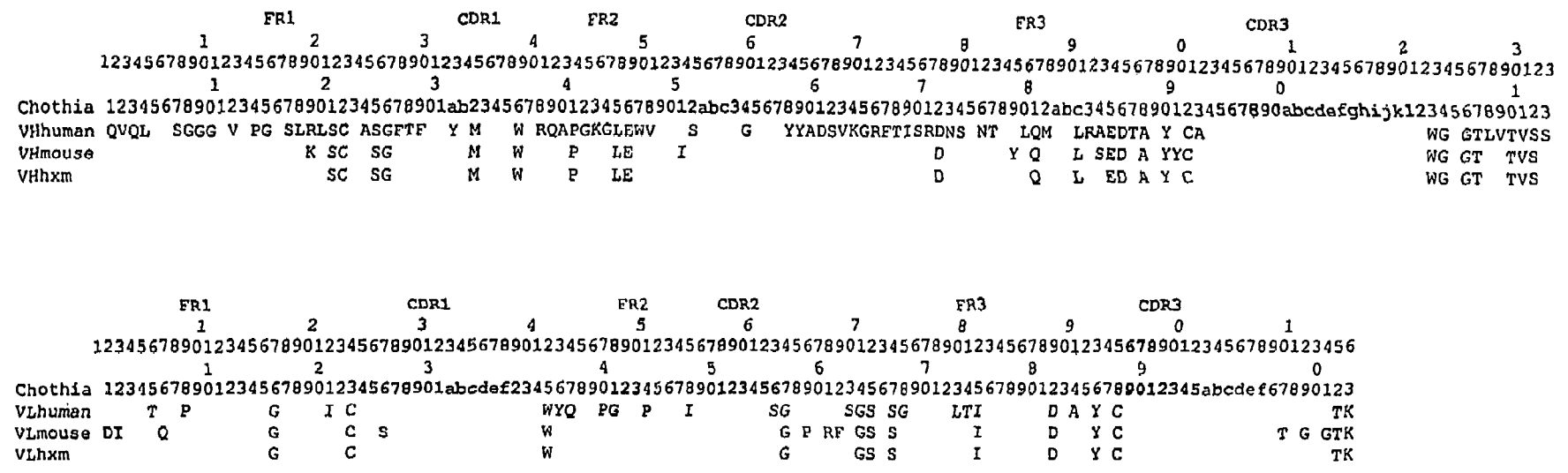

FIG. 11. Alignments of the VH (A) and VL (B) domains of the various anti-TAU. selected with IACT. The CDRs are in bold type. At the base of panels (A) and (B), the ICSs at 100% of this particular set of intrabodies are shown. Panel (C) shows the optimum ICSs for the human and mouse variable chains and those extrapolated between man and mouse (hxm). The numbering is according to Chothia.

Figure 12:
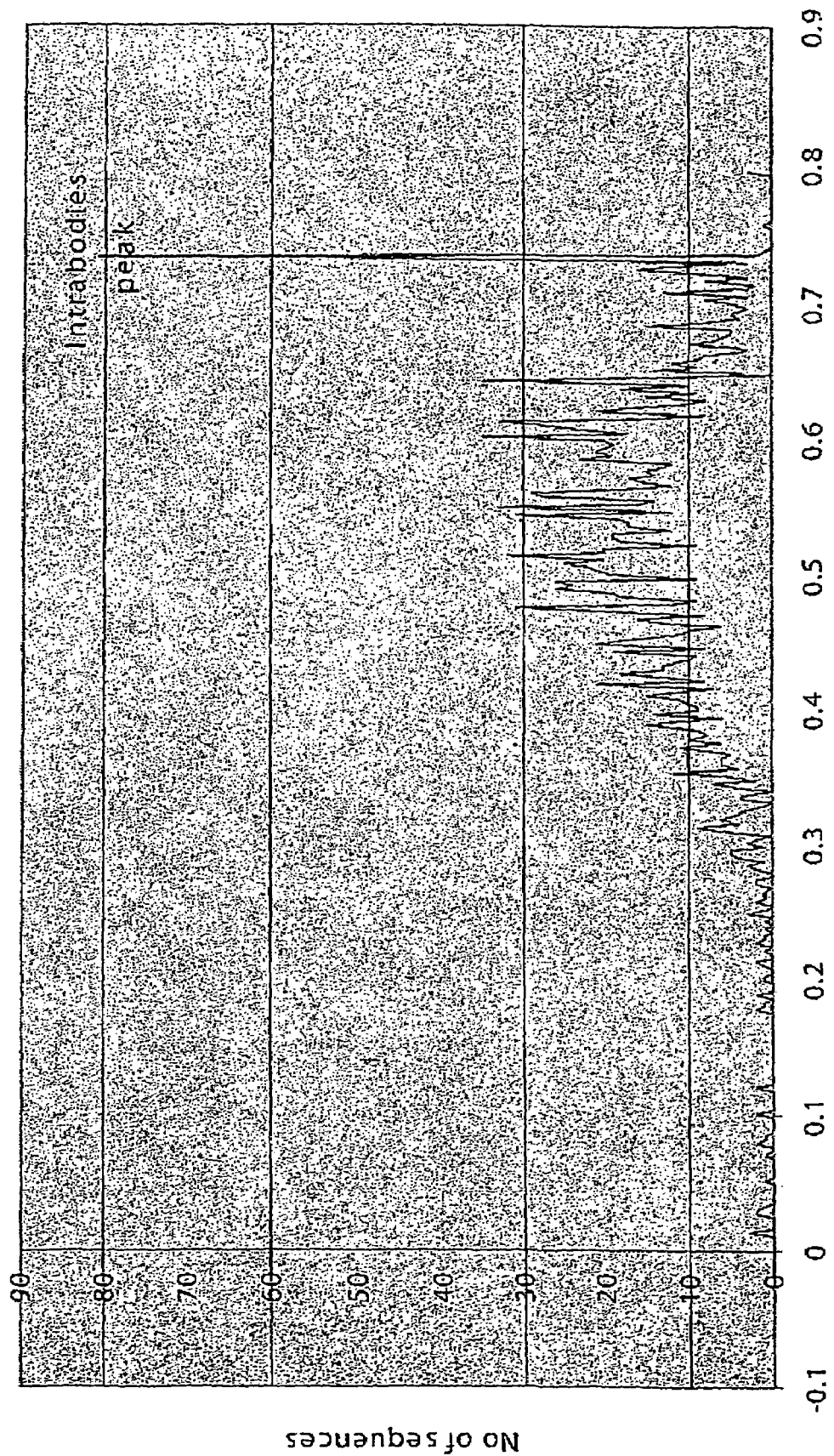

FIG. 12. Distribution of Ps for the human sequences. The infinite product in the calculation of Ps was extended just to the positions defined in the ICS.

Figure 13:
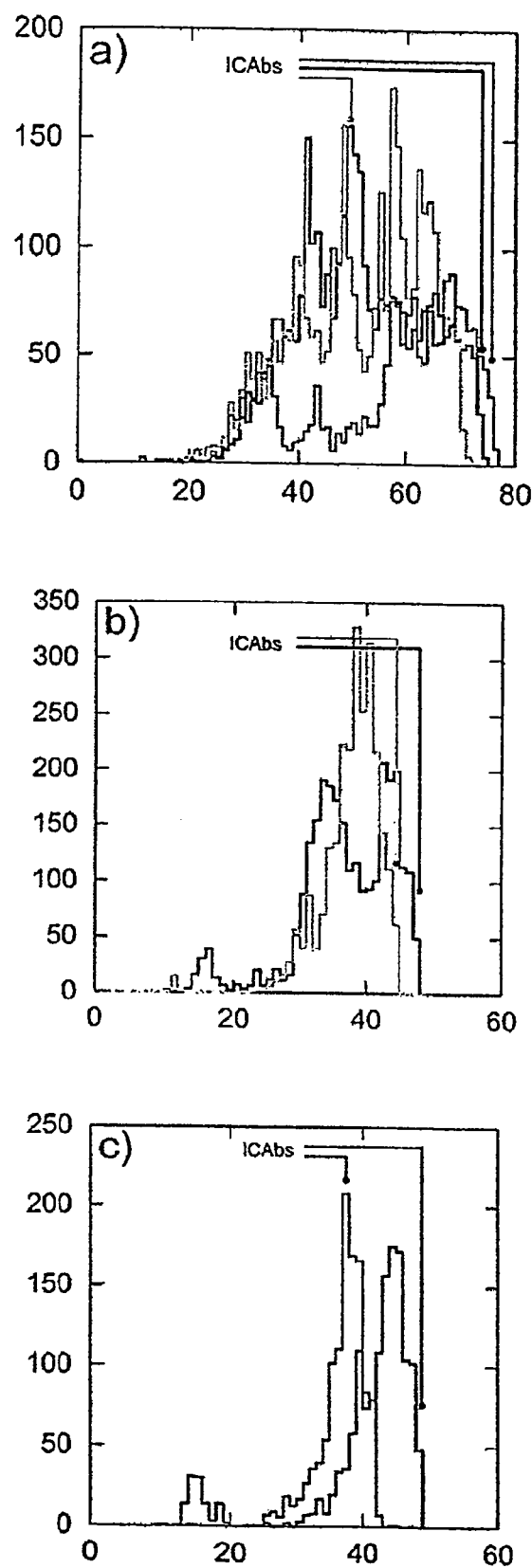

FIG. 13. Distribution of the level of homology of the sequences in the various subgroups of the Kabat database, in relation to the corresponding consensus sequence. Analysis was restricted to the positions corresponding to the conserved residues 76 (part a) and 48 (part b) and c) for the heavy and light chain respectively for the IACT set. The number of amino acid residues homologous with the consensus sequence of the corresponding Kabat database is shown on the abscissa: a) in black, human VH (set 1, 3319 sequences), in light grey, mouse VH (set 2, 3353 sequences), in dark grey human VH 3 (set 3); b) in black, human VL (set 4, 2731 sequences), in light grey, mouse VL (set 5. 2518 sequences); c) in black, human VK (set 6, 1330 sequences), in dark grey, human Vλ. (set 7, 1265 sequences). The lines that end in dots indicate the degree of homology of the IACT consensus sequence, for each subset of the database.

Figure 14:
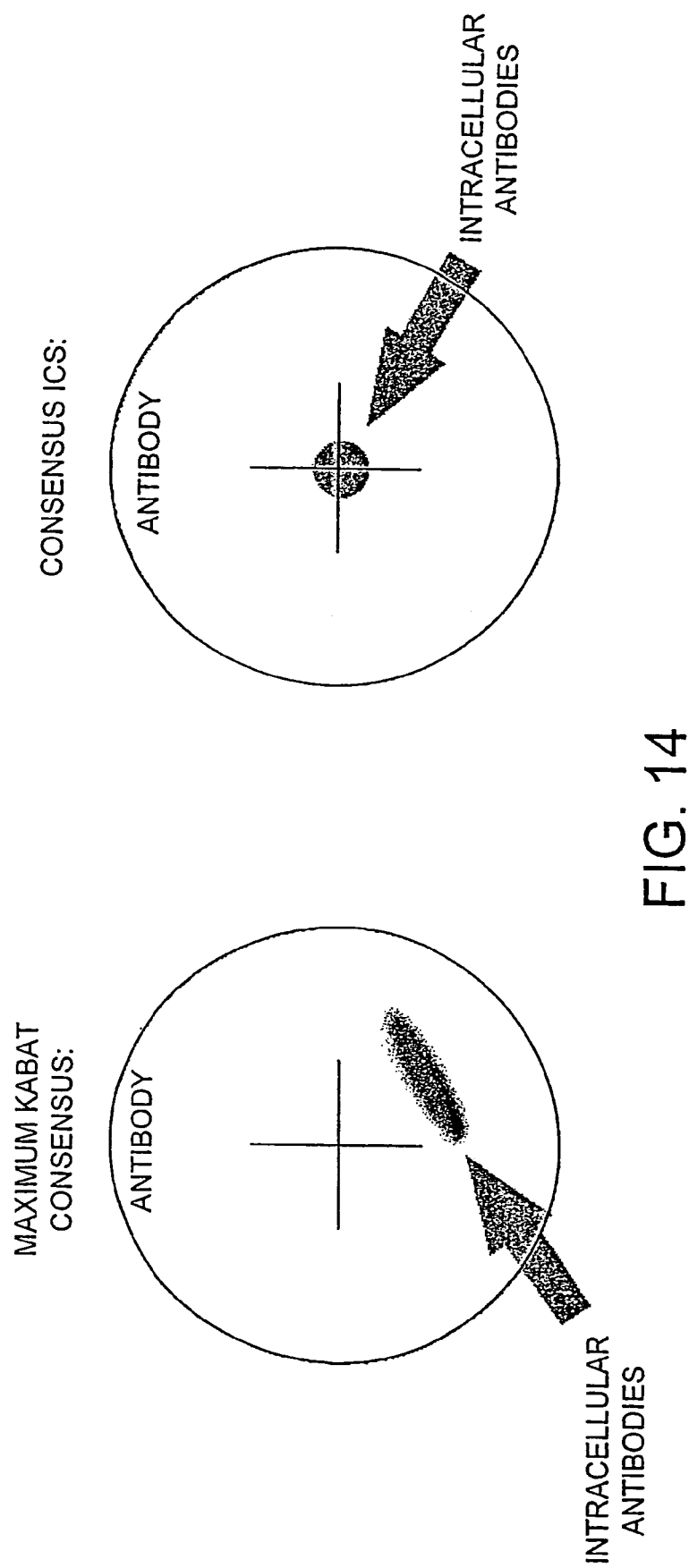

FIG. 14. Diagram showing how the TACT technology acts as a filter that brings a fraction of amino acids of the input sequences closer to the sequence of greatest consensus of the set.

Figure 15:
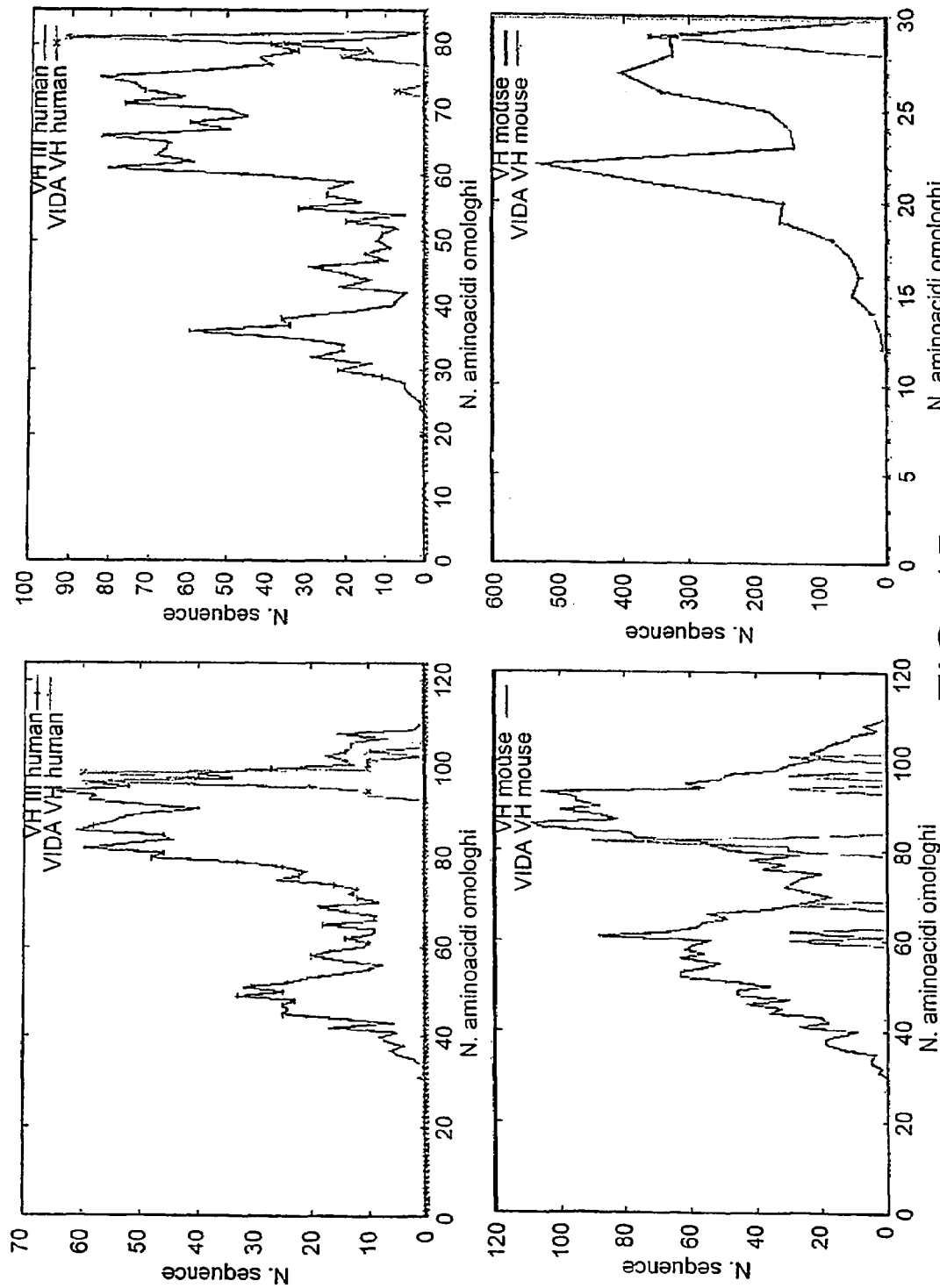
Figure 15:
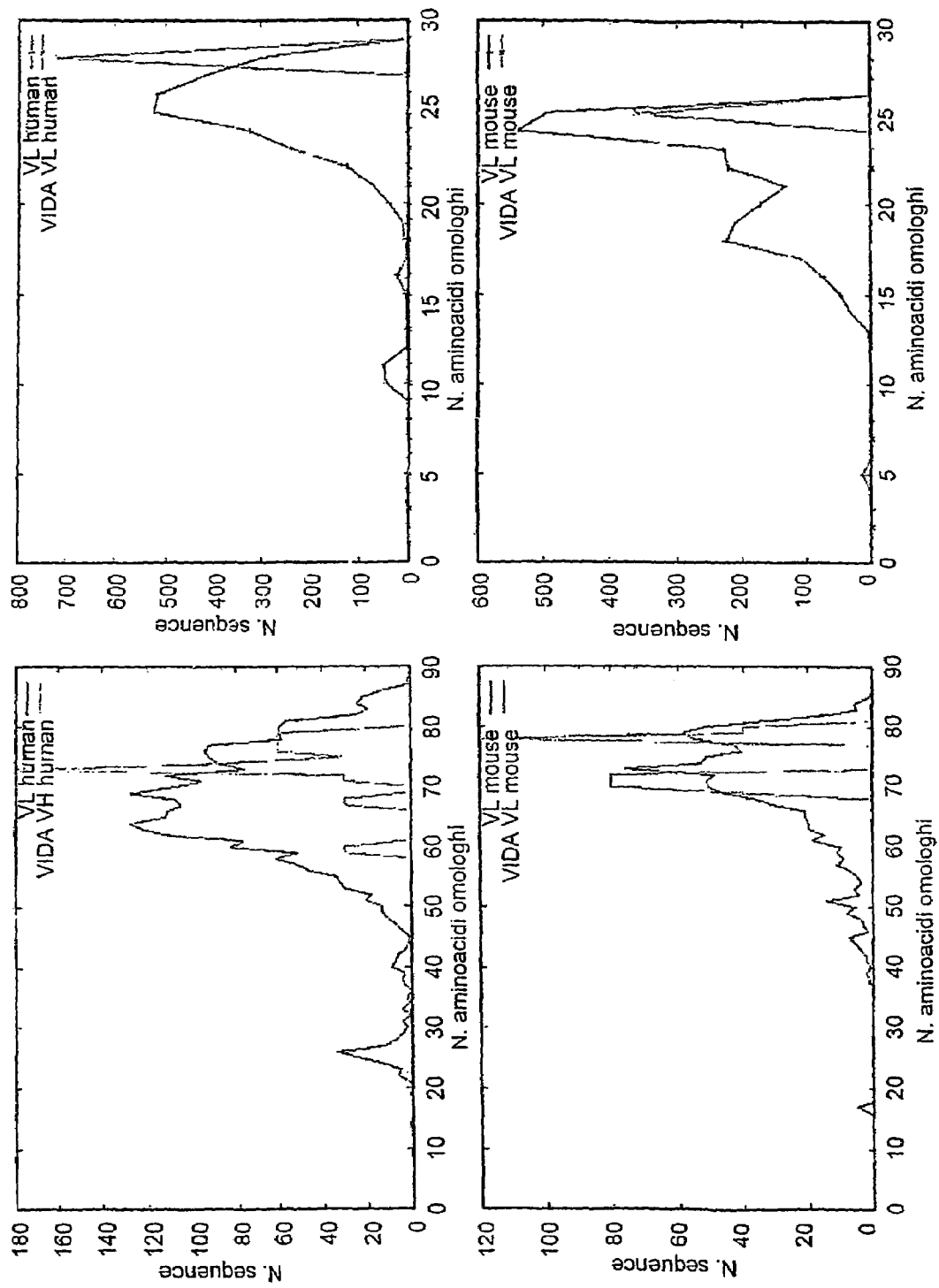

FIG. 15. (b) Distribution of the degree of homology with ICS sequences, in the VIDA subsets and in the respective Kabat subsets. (a) Distribution of the degree of homology with sequences of maximum consensus of the Kabat, in the VIDA subsets and in the respective Kabat subsets. The abscissa shows the number of amino acids identical to the ICSs.

DETAILED DESCRIPTION OF THE INVENTION

General Techniques

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference) and chemical methods. In addition Harlow & Lane, A Laboratory Manual Cold Spring Harbor, N.Y, is referred to for standard Immunological Techniques.

Method of Selecting Immunoglobulins Which Bind to their Ligand within an Intracellular Environment.

The Intracellular Antibody Capture Technology

A suitable method for the selection of immunoglobulins which bind to their ligand within an intracellular environment is described by the present inventors and detailed in WO00/54057 which is herein incorporated by reference.

Generally, it is difficult to obtain antibody fragments which bind to antigen in vivo because antibodies are not equipped to function in a reducing environment such as the cell cytoplasm (Martineau, P., Jones, P. & Winter, G. (1998), J. Mol. Biol. 280, 117-127; Proba, K., Ge, L. & Pluckthun, A. (1995), Functional antibody single-chain fragments from the cytoplasm of *Escherichia coli* in the presence of thioredoxin reductase (TrxB). Gene, 159, 203±207.). The intracellular antibody capture approach described WO00/54057 constitutes a generic strategy for selection and intracellular characterisation of antigen-specific scFv antibody fragments. By employing this strategy, the present inventors have identified immunoglobulin molecules which bind specifically to a liganci within an intracellular environment.

The IAC technology described in WO00/54057, includes one round of scFv phage display library screening in vitro with a recombinant bacterial protein, followed by selection in a yeast in vivo antibody-antigen interaction screening of the in vitro enriched scFv repertoire (Visintin, M., Tse, E., Axelson, H., Rabbitts, T. H. and Cattaneo, A. (1999) Proc. Natl. Acad. Sci. USA 96 11723-11728)

Those skilled in the art will appreciate that there are other suitable methods for the selection of immunoglobulin molecules which bind selectively to their ligand within the cell.

Intracellularly Binding Immunoglobulins

Immunoglobulin molecules, used according to the present invention include members of the immunoglobulin superfamily, which are a family of polypeptides which comprise the immunoglobulin fold characteristic of antibody molecules. The fold contains two beta sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The present invention is applicable to all immunoglobulin superfamily molecules which are capable of binding to target molecules. Preferably, the present invention relates to antibodies, and scFv fragments.

The immunoglobulins molecules used according to the present invention all possess the requisite activity of being capable of selectively binding to a ligand within an intracellular environment.

Advantageously, immunoglobulin molecules according to the invention all share a $V_H$ amino acid sequence which is a member of the VHIII subgroup of heavy chains. This suggests that immunoglobulins having a heavy chain which falls within the VHIII subgroup have particularly high efficacy in an in vivo environment. In addition, more advantageously, the immunoglobulin molecules according to the present invention have a VHIII subgroup joined to JH5 or $J_k1$ region.

The present inventors have surprisingly found however that it is not sufficient for an immunoglobulin molecule to have a heavy chain variable region which is a member of the VHII subgroup of heavy chains in order for it to be a good intracellular antibody. In fact, it has been found in some cases that anti-TAU antibodies of the VHIII subgroup, isolated at random from the library, and with good properties of binding with TAU in vitro, are incapable of binding TAU in vivo.

Most of the variability between the sequences of the present invention is concentrated within the CDRs, consistent with the view that the framework regions of the molecules confer structural stability on the immunoglobulin molecules, whilst the CDRs are involved in ligand binding. However, a high degree of conservation is present in these regions, consistent with the view that residues within these regions also contribute to the efficacy of binding within an vivo environment.

The immunoglobulins according to the invention are especially useful for diagnostic and therapeutic applications. Accordingly, they may be altered immunoglobulins comprising an effector protein such as a toxin or a label. Especially preferred are labels which allow the imaging of the distribution of the immunoglobulins in vivo. Such labels may be radioactive labels or radioopaque labels, such as metal particles, which are readily visualisable within the body of a patient. Moreover, they may be fluorescent labels or other labels which are visualisable on tissue samples removed from patients.

Recombinant DNA technology may be used to produce the immunoglobulins for use according to the present invention using an established procedure, in bacterial or preferably mammalian cell culture. The selected cell culture system preferably secretes the immunoglobulin product.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM. NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure immunoglobulin preparations and allows scale-up to give large amounts of the desired immunoglobulins. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired immunoglobulins can also be obtained by multiplying mammalian cells in vivo. For this purpose, hybridoma cells producing the desired immunoglobulins are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the immunoglobulins are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired immunoglobulins, preferentially by immunofluorescent staining of cells expressing the desired target by immunoblotting, by an enzyme immunoassay, e.g. a sandwich assay or a dot-assay, or a radioimmunoassay.

For isolation of the immunoglobulins, those present in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-)affinity chromatography, e.g. affinity chromatography with the target molecule or with Protein-A.

The invention employs recombinant nucleic acids comprising an insert coding for a heavy chain variable domain and/or for a light chain variable domain of antibodies. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or for a light chain variable domain of antibodies can be enzymatically or chemically synthesised from nucleic acids having the authentic sequence coding for a naturally-occurring heavy chain variable domain and/or for the light chain variable domain, or a variant or derivative thereof as herein described. Preferably said modification(s) are outside the CDRs of the heavy chain variable domain and/or of the light chain variable domain of the antibody.

Identity/Homology

It will be understood that polypeptide sequences of the invention are not limited to the particular sequences set forth in SEQ. ID. No. 1 to 40 or fragments thereof, but also include homologous sequences obtained from any source, for example related cellular homologues, homologues from other species and variants or derivatives thereof.

Thus, the present invention encompasses variants, homologues or derivatives of the amino acid sequences set forth in SEQ. ID. No. 1 to SEQ 40 as long as when said variants, homologues or derivatives of the amino acid sequences set forth in SEQ. ID. No. 1 to SEQ 40 are one or more components of a immunoglobulin molecule, they possess the requisite activity of binding selectively to a ligand within an intracellular environment.

In the context of the present invention, a homologous sequence is taken to include an amino acid sequence which is at least 94, 95, 96, 97, 98, 99% identical at the amino acid level over at least 30, preferably 50, 70, 90 or 100 amino acids. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (e.g., BLAST version 2.2.7; see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Method for Conferring upon an Immunoglobulin Molecule the Ability to Selectively Bind to a Ligand within an Intracellular Environment.

In a further aspect, the present invention provides a method for conferring upon an immunoglobulin molecule the ability to function within an intracellular environment comprising the steps of:

a) identifying the optimum ICS reference sequence;

b) optionally, modifying, by site-specific mutagenesis, the amino acid residues that are located in the positions defined by the optimum ICS, or a subset of these residues, in such a way that they are those identified by the optimum ICS.

Ligands

Potential ligands include polypeptides and proteins, particularly nascent polypeptides and proteins or intracellular polypeptide or protein precursors, which are present in the cell. Advantageously, the ligand is a mutant polypeptide or protein, such as a polypeptide or protein generated through genetic mutation, including point mutations, deletions and chromosomal translocations. Such polypeptides are frequently involved in tumourigenesis. Examples include the gene product produced by the spliced BCR-ABL genes. The invention is moreover applicable to all mutated oncogene products, all chromosomal translocated oncogene products (especially fusion proteins), aberrant proteins in expressed in disease, and viral or bacterial specific proteins expressed as a result of infection.

The ligand may alternatively be an RNA molecule, for example a precursor RNA or a mutant RNA species generated by genetic mutation or otherwise.

The ligand may be inserted into the cell, for example as described below, or may be endogenous to the cell.

Delivery of Immunoglobulins and Ligands to Cells

Generally the immunoglobulin will be delivered to the cell. The ligand as herein defined may be a native component of the cell as described above, or may also be delivered to the cell.

In order to introduce immunoglobulins and ligands/target molecules into an intracellular environment, cells are advantageously transfected with nucleic acids which encode the immunoglobulins and/or their ligands.

Nucleic acids encoding immunoglobulins and/or ligands can be incorporated into vectors for expression. As used herein, vector (or plasmid) refers to discrete elements that are used to introduce heterologous DNA into cells for expression thereof. Selection and use of such vehicles are well within the skill of the artisan. Many vectors are available, and selection of appropriate vector will depend on the intended use of the vector, the size of the nucleic acid to be inserted into the vector, and the host cell to be transformed with the vector. Each vector contains various components depending on its function and the host cell for which it is compatible. The vector components generally include, but are not limited to, one or more of the following: an origin of replication, one or more marker genes, an enhancer element, a promoter, a transcription termination sequence and a signal sequence.

Moreover, nucleic acids encoding the immunoglobulins and/or targets according to the invention may be incorporated into cloning vectors, for general manipulation and nucleic acid amplification purposes.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses.

The origin of replication from the plasmid pBR322 is suitable for most Gram-negative bacteria, the 2m plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast or mammalian cells even though it is not capable of replicating independently of the host cell chromosome. DNA may also be replicated by insertion into the host genome. However, the recovery of genomic DNA is more complex than that of exogenously replicated vector because restriction enzyme digestion is required to excise the nucleic acid. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRIP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript© vector or a pUC plasmid, e.g. pUC 18 or pUC 19, which contain both an *E. coli* replication origin and an *E. coli* genetic marker conferring resistance to antibiotics, such as ampicillin.

Suitable selectable markers for mammalian cells are those that enable the identification of cells expressing the desired nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked nucleic acid. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to the desired nucleic acid. Such a promoter may be inducible or constitutive. The promoters are operably linked to the nucleic acid by removing the promoter from the source DNA and inserting the isolated promoter sequence into the vector. Both the native promoter sequence and many heterologous promoters may be used to direct amplification and/or expression of nucleic acid encoding the immunoglobulin or target molecule. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the beta-lactamase and lactose promoter systems, alkaline phosphatase, the tryptophan (trp) promoter system and hybrid promoters such as the tac promoter. Their nucleotide sequences have been published, thereby enabling the skilled worker operably to ligate them a desired nucleic acid, using linkers or adaptors to supply any required restriction sites. Promoters for use in bacterial systems will also generally contain a Shine-Delgarno sequence operably linked to the nucleic acid.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60-89, 1990). In the *E. coli* BL21(DE3) host strain, used in conjunction with pET vectors, the T7 RNA polymerase is produced from the lysogen DE3 in the host bacterium, and its expression is under the control of the IPTG inducible lac UV5 promoter. This system has been employed successfully for over-production of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcHisXpress™ (Invitrogen) or pTrc99 (Pharmacia Biotech, SE), or vectors containing the tac promoter such as pKK223-3 (Pharmacia Biotech) or PMAL (new England Biolabs, MA, USA).

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or alpha-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the *S. cerevisiae* GAL 4 gene, the *S. pombe* nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such as the P1105 (−173) promoter element starting at nucleotide −173 and ending at nucleotide −9 of the PH05 gene.

Gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from promoters normally associated with immunoglobulin sequences.

Transcription of a nucleic acid by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to the desired nucleic acid, but is preferably located at a site 5' from the promoter.

Advantageously, a eukaryotic expression vector may comprise a locus control region (LCR). LCRs are capable of directing high-level integration site independent expression of transgenes integrated into host cell chromatin, which is of importance especially where the gene is to be expressed in the context of a permanently-transfected eukaryotic cell line in which chromosomal integration of the vector has occurred.

Eukaryotic expression vectors will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding the immunoglobulin or the target.

Particularly useful for practising the present invention are expression vectors that provide for the transient expression of nucleic acids in mammalian cells. Transient expression usually involves the use of an expression vector that is able to replicate efficiently in a host cell, such that the host cell accumulates many copies of the expression vector, and, in turn, synthesises high levels of the desired gene product.

Construction of vectors according to the invention may employ conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing gene product expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

Immunoglobulins and/or ligands may be directly introduced to the cell by microinjection, or delivery using vesicles such as liposomes which are capable of fusing with the cell membrane. Viral fusogenic peptides are advantageously used to promote membrane fusion and delivery to the cytoplasm of the cell.

Figure 5A:
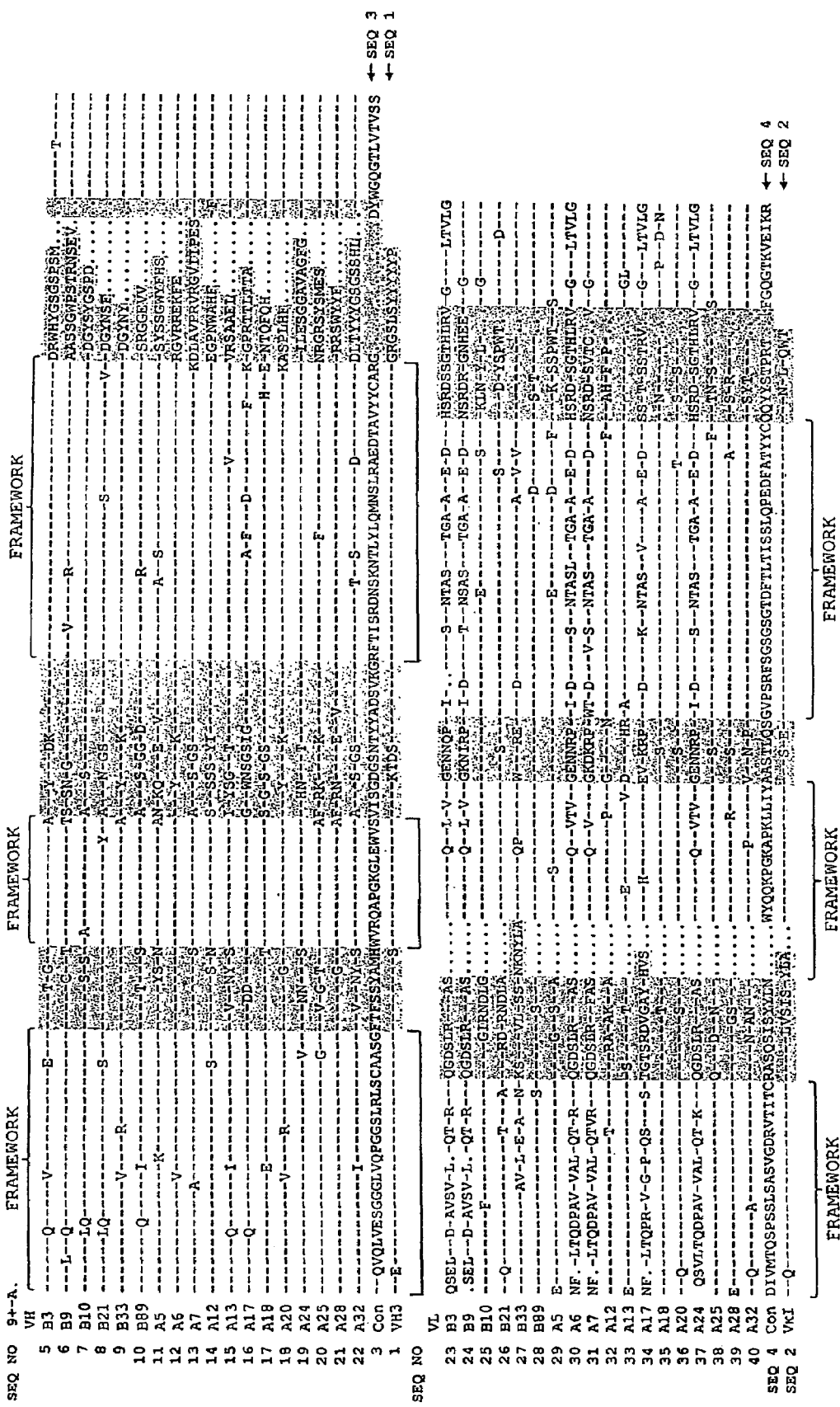

Preparation of a Library Using $V_H$ and $V_L$ Sequences of the Present Invention In yet a further aspect, the present invention provides a library, wherein the library is generated using any one or more of the variable heavy domain amino acid sequences (VH) selected from the group consisting of: a VH amino acid sequence showing at least 85% identity with the consensus sequence depicted as SEQ 3 and shown in FIG. 5a, a VH sequence which is described by the consensus sequence depicted in SEQ 41 and shown in FIG. 11a, These libraries may encode, express, and/or present immunoglobulin molecules or fragments thereof which may be tested for their ability to interact with a ligand within an intracellular environment. Advantageously, the library of the present aspect of the invention may be tested for the binding of immunoglobulin molecules expressed using the intracellular antibody capture method described in WO00/54057. Advantageously, libraries of the present invention will encode or express $V_H$ and $V_L$ chains which when incorporated within an immunoglobulin molecule will bind selectively to a ligand within an intracellular environment. Preferably the immunoglobulin is scFv.

Systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et a!. (1990) supra; Kang et al. (1991) Proc. Natl. Acad. Sci. U.S.A. 88: 4363; Clackson et al. (1991) Nature, 352: 624; Lowman et al. (1991) Biochemistry, 30: 10832; Burton et al. (1991) Proc. Natl. Acad. Sci U.S.A., 88: 10134; Hoogenboom et al. (1991) Nucleic Acids Res., 19: 4133; Chang et al. (1991) J. Immunol., 147: 3610; Breitling et al. (1991) Gene, 104: 147; Marks et al. (1991) supra; Barbas et al. (1992) supra; Hawkins and Winter (1992) J. Immunol., 22: 867; Marks et al., 1992, J. Biol. Chem., 267: 16007; Lerner et al. (1992) Science, 258: 1313, incorporated herein by reference).

Alternative library selection technologies include bacteriophage lambda expression systems, which may be screened directly as bacteriophage plaques or as colonies of lysogens, both as previously described (Huse et al. (1989) Science, 246: 1275; Caton and Koprowski (1990) Proc. Natl. Acad. Sci. U.S.A., 87; Mullinax et al. (1990) Proc. Natl. Acad. Sci. U.S.A. 87: 8095; Persson et al. (1991) Proc. Natl. Acad. Sci. U.S.A., 88: 2432) and are of use in the invention. Whilst such expression systems can be used to screening up to $10^6$ different members of a library, they are not really suited to screening of larger numbers (greater than $10^6$ members). Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) Science, 251: 767; Dower and Fodor (1991) Ann. Rep. Med. Chem., 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) Science, 249: 505; Ellington and Szostak (1990) *Nature,* 346: 818). A similar technique may be used to identify DNA sequences which bind a predetermined human transcription factor (Thiesen and Bach (1990) *Nucleic Acids Res.,* 18: 3203; Beaudry and Joyce (1992) *Science,* 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

Practically the major advantage in the generation of libraries from the consensus sequences as herein described is that their production will obviate the use of phage scFv libraries and will reduce the necessary library size required for use in intracellular antibody capture technology, Uses of Immunoglobulins of the Present Invention Immunoglobulin molecules according to the present invention, preferably scFv molecules may be employed in in vivo therapeutic and prophylactic applications, in vitro and in vivo diagnostic applications, in vitro assay and reagent applications, in functional genomics applications and the like.

Therapeutic and prophylactic uses of immunoglobulins and compositions according to the invention involve the administration of the above to a recipient mammal, such as a human. Preferably they involve the administration to the intracellular environment of a manunal.

Substantially pure immunoglobulins of at least 90 to 95% homogeneity are preferred for administration to a mammal, and 98 to 99% or more homogeneity is most preferred for pharmaceutical uses, especially when the mammal is a human. Once purified, partially or to homogeneity as desired, the immunoglobulin molecules may be used diagnostically or therapeutically (including extracorporeally) or in developing and performing assay procedures using methods known to those skilled in the art.

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

The selected immunoglobulin molecules of the present invention can perturb protein function in vivo and thus will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis), and in preventing transplant rejection. For instance, one application of the intracellular immunoglobulins of the present invention is in perturbing the function of oncogenic proteins, in particular fusion molecules which result chromosomal translocations. These molecules are of particular interest as they are tumour-specific proteins only occurring in the progeny of cell which acquired the chromosomal translocation. A notable example is the BCR-ABL hybrid fusion protein found in CML (Chronic myelogenous leukaemia) and a proportion of ALL (Acute lymphoblastic leukaemia) carrying translocation t(9; 22)(q34;q11) (de Klein, A. et al. (1982) A cellular oncogene is translocated to the Philadelphia chromosome in chronic myelocytic leukaemia. Nature, 300, 765-767. Bartram, C. R. et al. (1983) Translocation of c-abl oncogene correlates with the presence of a Philadelphia chromosome in chronic myelocytic leukaemia. Nature, 306, 277-280.)

The present inventors have selected scFv directed to the SH2 domain of ABL or the SH2 binding domain of the BCR protein, which are found in both p190 and p210 BCR-ABL fusion proteins. A panel of different scFv which bind BCR-ABL in vivo have been found by the present inventors.

The antigen-specific scFv according to the present invention may be used as therapeutic agents in Philadelphia chromosome positive leukaemias. It has been shown that the SH2 binding domain of the BCR protein is essential for the transforming properties of the BCR-ABL oncogenic protein BCRsh2bd. Therefore blocking the function of this domain may neutralise the oncogenicity of BCR-ABL. In addition, the scFv have the potential to be employed, in combination with anti-ABL scFv, in an intracellular antibody mediated cell killing approach (Eric Tse and Terence H. Rabbitts Intracellular antibody-caspase. mediated cell killing: An approach for application in cancer therapy Proc. Natl. Acad. Sci. USA 97: 12266-12271. Using this approach, cells carrying the BCR-ABL proteins could be specifically killed, sparing the normal ones.

Animal model systems which can be used to screen the effectiveness of the selected immunoglobulins of the present invention in protecting against or treating disease are available.

Methods for the testing of systemic lupus erythematosus (SLE) in susceptible mice are known in the art (Knight et al. (1978) J. Exp. Med., 147: 1653; Reinersten et al. (1978) New Eng. J. Med., 299: 515). Myasthenia Gravis (MG) is tested in SJL/J female mice by inducing the disease with soluble AchR protein from another species (Lindstrom et al,. (1988) Adv. Immunol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-2 13; McFarlin et al. (1973) Science, 179: 478: and Satoh et al. (1987) J. Immunol., 138: 179).

Generally, the selected immunoglobulins of the present invention will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The selected immunoglobulins of the present invention may be used as separately administered compositions or in conjunction with other agents. These can include various immunotherapeutic drugs, such as cylcosporine, methotrexate, adriamycin or cisplatinuin, and immunotoxins. Pharmaceutical compositions can include "cocktails" of various cytotoxic or other agents in conjunction with the chemokines, or binding proteins thereof, or T-cells of the present invention or even combinations of selected chemokines, or binding proteins thereof, according to the present invention.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The selected immunoglobulins of the present invention can be lyophilised for storage and reconstituted in a suitable carrier prior to use. Known lyophilisation and reconstitution techniques can be employed. It will be appreciated by those skilled in the art that lyophilisation and reconstitution can lead to varying degrees of functional activity loss and that use levels may have to be adjusted upward to compensate.

The compositions containing the present selected immunoglobulins of the present invention or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected immunoglobulin per kilogram of body weight, with doses of 0.05 to 2.0 mg/kg/dose being more commonly used. For prophylactic applications, compositions containing the present selected immunoglobulin molecules or cocktails thereof may also be administered in similar or slightly lower dosages.

A composition containing one or more selected immunoglobulin molecules according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the selected antibodies, cell-surface receptors or binding proteins thereof whereby the undesired cells are killed or otherwise removed from the blood for return to the mammal in accordance with standard techniques.

The invention is further described, for the purposes of illustration only, in the following examples.

EXAMPLES

Strategy (A)

Example 1

Bacterial Protein Expression and Purification of Antigens

BCR antigen: A plasmid for expression of histidine tagged SH2 binding domain of BCR in bacteria, pRSET-BCRSH2BD, was made by amplifying the sequences encoding amino acids 185-417 of BCR and cloning the PCR product into mini pRSET vector (a gift from O. Perisic) as BamHI-EcoRI fragment.

ABL antigen: A plasmid for bacterial expression of histidine tagged ABL protein SH2 domain (amino acid 26-348) (pRSET-ABL) was constructed by PCR of the corresponding sequences and subcloning the PCR product as BamHI-EcoRI fragment into mini pRSET vector. PCR conditions were 30 cycles of 1 minute each at 95° C., 50° C. and 72° C. using specific primers (5'cagggatccgagcgcggcctggtgaag3'/5' caggaattcatcgttgggccagatctg3' for pRSET-BCRSH2BD and 5'cagggatccgaagcccttcagcggcca3'/5'caggaattccgagatctgagtggccat3' for pRSET-ABL) and pE1A2 (BCR-ABL p190, a gift from Dr. G. Grosveld) as template.

The plasmids were transformed into $E.\ coli$ C41 bacteria (Tse, E., & Rabbitts, T. H (2000) Proc. Nat. Acad. Sci. USA 97, 12266-12271) and induction of protein was performed by adding 1 mM IPTG to the exponentially growing bacterial culture (O.D.$_{600}$ 0.6) and by growth at 30° C. for 4 hours. The histidine tagged proteins were purified using Ni-NTA agarose according to manufacturer's instructions (Qiagen). Concentration of the purified proteins was determined by using Bio-Rad Protein Assay Kit (BIO-RAD).

Example 2

In Vitro scFv Phage Display Library Screening and Preparation of SpecificscFv-VPl6 Yeast Library A detailed protocol for the IAC methodology is described elsewhere (Tse, E., Chung., G & Rabbitts, T., H K, Turksen, Editor, 2000, Humana Press: Totawa). Purified His-tagged SH2 binding domain of BCR protein or the SH2 domain of ABL protein were coated onto immunotubes (Nunc) at a concentration of 50 μ/ml in PBS for overnight at 4° C. $2 \times 10^{13}$ phage displaying scFv (Sheets, M. D., et al (1998) Proc. Nat. Acad Sci, USA 95, 6157-6162) were incubated with the antigen-coated tubes and the bound phage were eluted with 100 mM triethylamine, neutralised by 1M Tris, pH 7.4 and were used to infect $E.\ coli$ TG1 bacteria. The transduced bacteria were amplified by plating onto ampicillin supplemented agar plate from which phagemid DNA was extracted. The collected phagemid DNA was digested with SfiI and NotI restriction enzyme and the 700-800 bp scFv DNA fragment was gel purified. The purified scFv (SfiI/NotI) DNA fragment was ligated to pVPl6 vector and transformed into $E.\ coli$ DH5α bacteria. 40 ligations were performed to obtain around $10^5$ bacteria colonies after transformation. This generated the primary BCR-SH2BD and ABL-SH2 specific yeast scFv-VP16 libraries which were amplified by plating onto ampicillin supplemented agar plate. DNA was extracted from the bacteria and used for yeast screening.

Example 3

In Vivo Antibody—Antigen Interaction Screening in Yeast

L40 Yeast (Statagene) was grown at 30° C. for 3-4 days, in YAPD medium (1% yeast extract, 2% Bacto-Peptone, 2% glucose, and 0.1% mg/ml adenine buffered at pH5.8) or in synthetic minimal YC medium (0.12% yeast nitrogen base, without amino acids and 0.5% ammonium sulphate, 0.1% succinic acid, 0.6% NaOH, 2% glucose and, as required, 2% agar) containing 0.075% amino acid supplements (lacking Trp, Leu, Ura, Lys, and His; 0.1% each of adenine sulphate, Arg, Cys, Thr; 0.05% each of Asp, Ile, Met, Phe, Pro, Ser, and Tyr) buffered at pH5.8. When necessary, 0.01% each of Trp, Ura, Lys, Leu and 0.005% His were supplemented to the media.

The bait antigen expressing plasmid comprised LexA linked to BCR-ABL (pBTM/E1A2) was made by subcloning the 4 kb blunted EagI fragment of pE1A2 into BamHI blunted pBTM/116 vector. For yeast in vivo scFv library screening, 1 mg of pBTM/E1A2 and 500 μg of the yeast scFv-VP16AD (where AD is activation domain) library DNA were co.-transformed into *Saccharomyces cerevisiae* L40 by lithium acetate transformation protocol (Gietz, D., St. Jean, A., Woods, R. A. & Schiestl, R. H. (1992). Nucleic Acids Res. 20, 1425; Tse, E., Chung, G, & Rabbitts, T, H, K, Turksen, Editor, 2000, Humana Press: Totawa). Positive clones were selected by using auxotrophic markers for both plasmids and for histidine prototropy. Histidine independent colonies were picked, restreaked onto YC agar plates lacking Trp and Leu and assayed for β-gal activity by filter assay (Breeden, L. & Nasmyth, K. (1985) Cold Spring Harb. Symp. Quant. Biol. 50, 643-650. For re-testing the isolated scFv, individual scFv-VP16AD plamids (200 ng) were cotransformed with pBTM/E1A2 (500 ng) into L40 yeast, and histidine prototropy and β-gal activity were assayed. pBTM/AMCV (comprising the LexA DNA binding domain fused to the AMCV viral coat protein) used as a negative "bait" control was described previously (Tavladoraki, P., Benvenuto, E., Trinca, S., De Martinis, D., Cattaneo, A. & Galeffi, P. (1993) Nature (London) 366, 469-72; Viscintin, M., Tse, E., Axelson, H., Rabbitts, T. H & Cattaneo, A., (1999) Proc. Nat. Acad. Sci, USA 96, 11723-11728).

Example 4

In Vitro Characterisation of ICAbs scFv was expressed as soluble bacterial periplasmic protein and used as primary antibodies for Western immunodetection. scFv DNA fragments were isolated from the scFv-VP16AD plasmid by SfiI-NotI restriction enzyme digestion and subcloned into pHEN2 vector (see www.Mrc-cpe.cam.ac.uk) to make pHEN2-scFv for bacterial periplasmic expression. pHEN2-scFv plasmids were transformed into *E. coli* HB2151 and induction of protein was performed by adding 1 mM IPTG to 50 ml exponentially growing bacterial culture (O.D.$_{600}$ 0.6) and by further growing at 30° C. for 4 hours. The cells were pelleted and resuspended in 400 μl of ice-cold 1×TES buffer (0.2M Tris-HCl; 0.5 mM EDTA; 0.5M sucrose). 600 μl of 1:5 TES buffer (ice-cold) was added, mixed gently by inversion and placed on ice for 30 minutes. The supernatant containing the periplasmic soluble scFv was collected after centrifugation. The periplasmic protein was used fresh for immunodetection at a dilution of 1:50. 9E10 anti-myc tag mouse monoclonal antibody and HRP-conjugated anti-mouse antibody were used as the secondary antibodies at 1:1000 and 1:2500 dilution respectively.

Example 5

Mammalian In Vivo Antibody—Antigen Interaction Assay

The expression vector pEF-BOS-VPHS3 allows cloning of scFv in-frame with the VP16 transcriptional activation domain for mammalian expression. Individual anti-BCR scFv DNA fragments were cloned into the SfiINotI site of pEF-BOS-VPHS3. Expression plasmids for scFvF8 (anti-AMCV virus coat protein) and scFvR4 (anti-beta-galactosidase (Martineau, P., Jones, P., & Winter, G, (1998, J. Mol. Biol. 280, 117-127)) was constructed by inserting the appropriate PCR products into the Sfi-NotI site of pEF-BOS-VPHS3 (Tavladoraki, P., Benvenuto, E., Trinca, S., De Martinis, D., Cattaneo, A. & Galeffi, P. (1993) Nature (London) 366, 469-472. The mammalian BCR-ABL expression plasmid, expressing Gal4DBD linked to BCR-ABL (pM3-E1A2) was made by subcloning the 4 kb EagI fragment of pE1A2 REF into the SmaI site of pM3 (Sadowski, I., Bell, B., Broad, P & Hollis, M,. (1992), Gene 118, 137-141). The control bait pM1-βgal has been described previously (Visintin, M., Tse, E., Axelson, H., Rabbitts, T. H., & Cattaneo, A., (1999), Proc. Nat. Acad. Sci, USA 96 11723-11728).

Chinese hamster ovary (CHO) cells were maintained in a minimal essential medium (GIBCO/BRL) with 10% foetal calf serum, penicillin and streptomycin. One day prior to transfection, 2×10$^5$ CHO cells were seeded onto a single well of 6 well-plate. CHO cells were transiently transfected with 0.5% g of bait plasmid and pEF-BOS-scFv-VP16, together with 0.5 μg of G5-Luciferase reporter plasmid (de Wet, J. R, Wood, K. V., DeLuca, M., Helinski, D. R., & Subramani, S., (1987) Mol Cell Biol 7, 725-37). and 50 ng of pRL-CMV internal control plasmid (Promega), using Lipofectamine (GIBCO/BRL, according to manufacturer's instructions). 60 hours after transfection, luciferase assays were performed on the CHO cell extracts using the Dual-Luciferase Reporter Assay System (Promega) and a luminometer. Transfection efficiency was normalised with the Ranilla luciferase activity measured. Each transfection was performed twice.

Example 6

Figure 1:
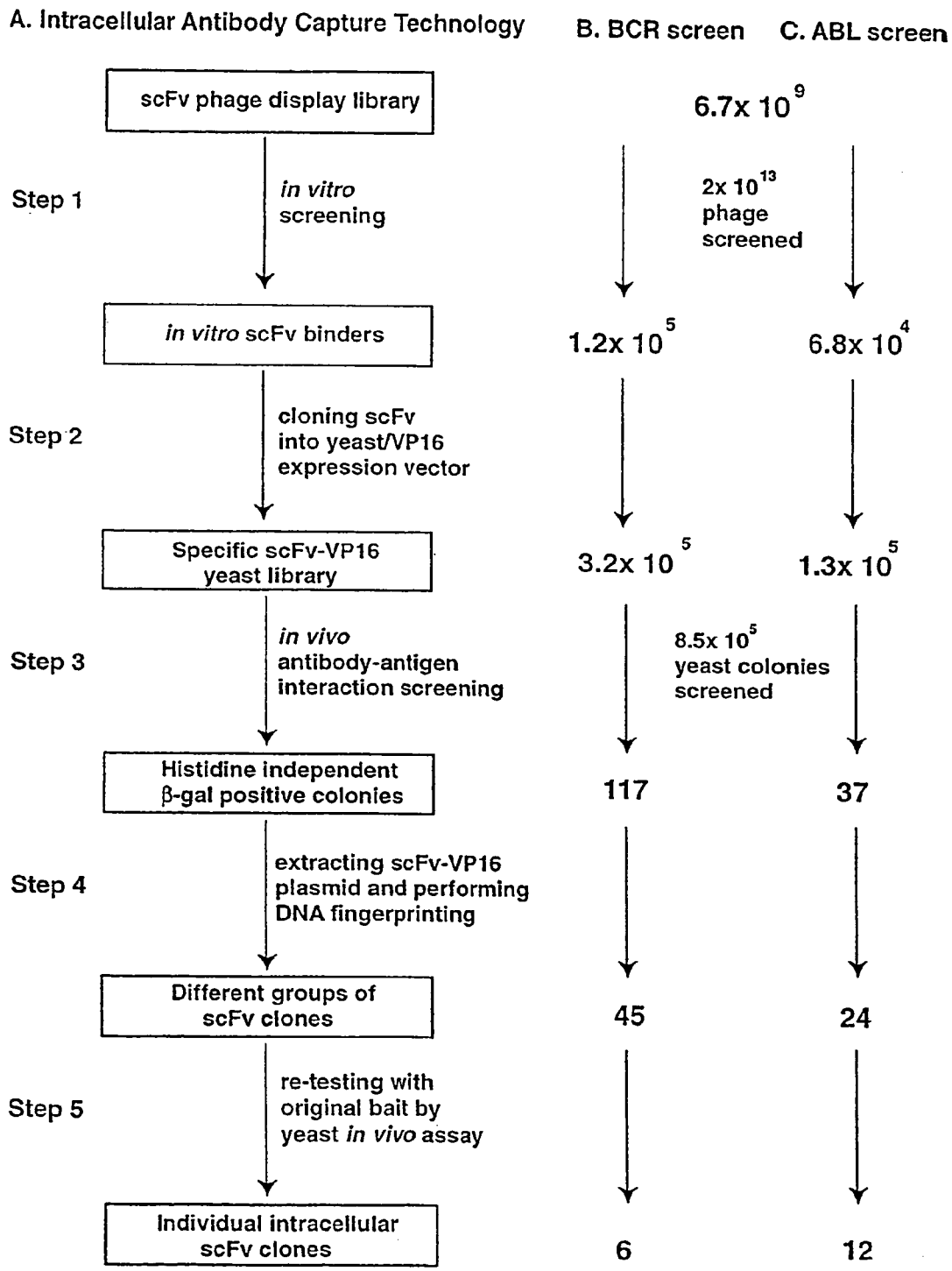
FIG. 1 describes the isolation of intracellular antibodies directed against BCR or ABL using the IAC technology.
A. The flow chart (left) shows the steps involved in the IAC technology (Visintin, M., Tse, B., Axelson, H., Rabbitts, T. H. and Cattaneo, A. (1999) Proc. Natl. Acad. Sci. USA 96 11723-11728)
Step 1: An scFv phage display library was used to screen antigen in vitro; the antigen in these experiments was made using bacterial expression systems. Step 2: All phage binding to antigen were recovered, plasmid DNA prepared and scFv fragments cloned into the yeast prey vector pVP16 to generate a sub-library of scFv enriched for antigen binding. Step 3: The yeast scFv sub-library was screened in yeast expressing antigen fused to a DNA binding domain as a bait and colonies growing on histidine selection plates were recovered and assayed for beta-gal activation. Step 4: Clones which grow in the absence of histidine and activate beta-gal were used to prepare plasmid DNA and the various selected clones fingerprinted with BstNI digestion to identify groups of scFv. Step 5: Members of each group are subsequently re-tested in yeast with the original bait clone to identify those scFv which genuinely bind to antigen. These scFv are further characterised in mammalian cells.
B IAC of anti-BCR scFv
C. IAC of anti-ABL scFv
In B and C, $2 \times 10^{13}$ clones from a phage library were screened with antigen using in vitro methods (Sheets, M. D., Amersdorfer, P., Finnem, R., Sargent, P., Lindqvist, E., Schier, R., Hemingsen, G., Wong, C., Gerhart, J. C. and Marks, J. D. (1998) Proc. Natl. Acad. Sci. USA 95 6157-6162) and (Vaughan, T. J., Williams, A. J., Pritchard, K., Osbourn, J. K., Pope, A. R., Eamshaw, J. C., McCafferty, J., Hodits, R. A., Wilton, J. & Johnson, K. S. (1996). Human antibodies with sub-nanomolar affinities isolated from a large non-immunized phage display library. Nature Biotechnol. 14, 309-314.). Around $10^5$ phage were recovered, cloned into the yeast vector pVP16 to make sub-libraries of 3.2 and $1.3 \times 10^5$ for anti-BCR and anti-ABL respectively. Approximately $8.5 \times 10^5$ yeast were screened (Visintin, M., Tse, E., Axelson, H., Rabbitts, T. H. and Cattaneo, A. (1999) Proc. Natl. Acad. Sci. USA 96 11723-11728) with BCR-ABL bait yielding 117 and 37 clones. These were sub-divided further by sequence analysis into 6 and 12 anti-BCR and anti-ABL respectively.

Isolating Specific Intracellular scFv Against BCR and ABL Proteins by In Vivo Antibody-antigen Interaction Screening The genetic screening approach to the isolation of intracellular antibodies comprised of yeast expression of a "bait" antigen fused to the LexA DNA binding domain (DBD) and a library of scFv fused to the VP16 transcription activation domain (AD) (Visintin, M., Tse, E., Axelson, H., Rabbitts, T. H. and Cattaneo, A. (1999) Proc. Natl. Acad. Sci. USA. 96 11723-11728. Interaction between the antigen bait and a specific scFv in the yeast intracellular environment results in the formation of a complex which can activate yeast chromosomal reporter genes, such as HIS3 and LacZ. This facilitates the identification and thus isolation of the yeast carrying the DNA vectors encoding the scFv. The main limitation of this approach is the number of scFv-VP 16 fusion clones that can be screened in yeast antibody-antigen interaction system (conveniently up to 2-5×10$^6$). This figure is well below the size of scFv repertoires displayed on phage (Sheets, M. D., Amersdorfer, P., Finnern, R., Sargent, P., Lindqvist, E., Schier, R., Hemingsen, G., Wong, C., Gerhart, J. C. and Marks, J. D. (1998) Proc. Natl. Acad. Sci. USA 95 6157-6 162; McCafferty et al (1990), Nature 348, 552-554). Thus to limit the numbers of scFv to be screened in vivo in yeast, we have used one round of in vitro phage scFv library screening using recombinant protein as antigen, prior to the in vivo yeast antibody-antigen interaction screening. A flow chart of our overall strategy to obtain antigen specific intracellular antibodies to BCR and ABL is shown in FIG. 1.

The protein antigens for the in vitro screening were made by expressing either the SH2 binding domain of the BCR protein (BCR) or the SH2 domain of ABL (ABL) as recombinant protein. The purified antigens were used for screening an scFv phage display library (Sheets, M. D., Amersdorfer, P., Finnem, R., Sargent, P., Lindqvist, E., Schier, R., Hemingsen, G., Wong, C., Gerhart, J. C. and Marks, J. D. (1998) Proc. Natl. Acad. Sci. USA 95 6157-6162,) (a gift from Dr. James Marks) in vitro. The library was derived from spleen cells and peripheral blood lymphocytes of human origin and had an initial diversity of $6.7 \times 10^9$. A total of $2 \times 10^{13}$ phage from the amplified library were screened with the purified protein fragments. After one round of in vitro phage screening, about $10^5$ antigen-bound phage were recovered (FIG. 1). These sub-libraries had a reduced complexity because of the enrichment of antigen-specific scFv. Phagemid DNA encoding the scFv was extracted, DNA fragments encoding scFv were sub-cloned into the yeast prey expression vector to create yeast scFv-VP16AD libraries of $3.2 \times 10^5$ and $1.3 \times 10^5$ for BCR and ABL respectively (i.e. about 3 times the original size of the enriched phage sub-library size). In vivo yeast antibody-antigen interaction screening was performed (Visintin, M et al (1999) Proc. Nat. Acad. Sci, USA 96, 11723-11728; Tse, E et al, K. Turksen, Editior, 2000, Humana Press: Totawa) by co-transforming *Saccharoinyces cerevisiae* L40 with a bait plasmid expressing BCR-ABL p190 (pBTM/E1A2) and the BCR or ABL scFv-VP16AD library. A total of approximately $8.5 \times 10^5$ yeast colonies were screened and 117 (anti-BCR) or anti ABL yeast colonies were selected, and confirmed using beta-galactosidase (beta-gal) filter assays (FIG. 1), indicating an interaction between the scFv and the BCR-ABL protein in the yeast cytoplasm.

The scFv-VP16AD plasmids were isolated from the yeast clones and into sorted into different groups according to BstNI DNA fingerprinting patterns, yielding 45 (anti-BCR) and 24 (anti-ABL) clones. Verification of the intracellular binding of scFv with antigen was determined using representatives of the groups in re-transfections with the original antigen bait and assay by histidine-independent growth and beta-gal activation. In this way, ten anti-BCR and 12 anti-ABL scFv were verified by activation of beta-gal. Examples of this are displayed in FIG. 2 in which interaction of anti-BCR scFv with BCR-ABL in yeast is shown. The specificity of the scFv binding to BCR-ABL was further verified by the lack of interaction between them and non-relevant antigen (a plant virus coat protein antigen AMCV) in the yeast in vivo assay (FIG. 2B) and by the lack of binding of the non-relevant scFv F8 to the BCR-ABL bait (FIG. 2A) (Taviadoraki, P., Benvenuto, B., Trinca, S., Dc Martinis, D., Cattaneo, A. & Galeffi, P. (1993) Nature (London) 366, 469-472).

Example 7

Expression of Antigen-specific scFv in Bacteria

Figure 3:
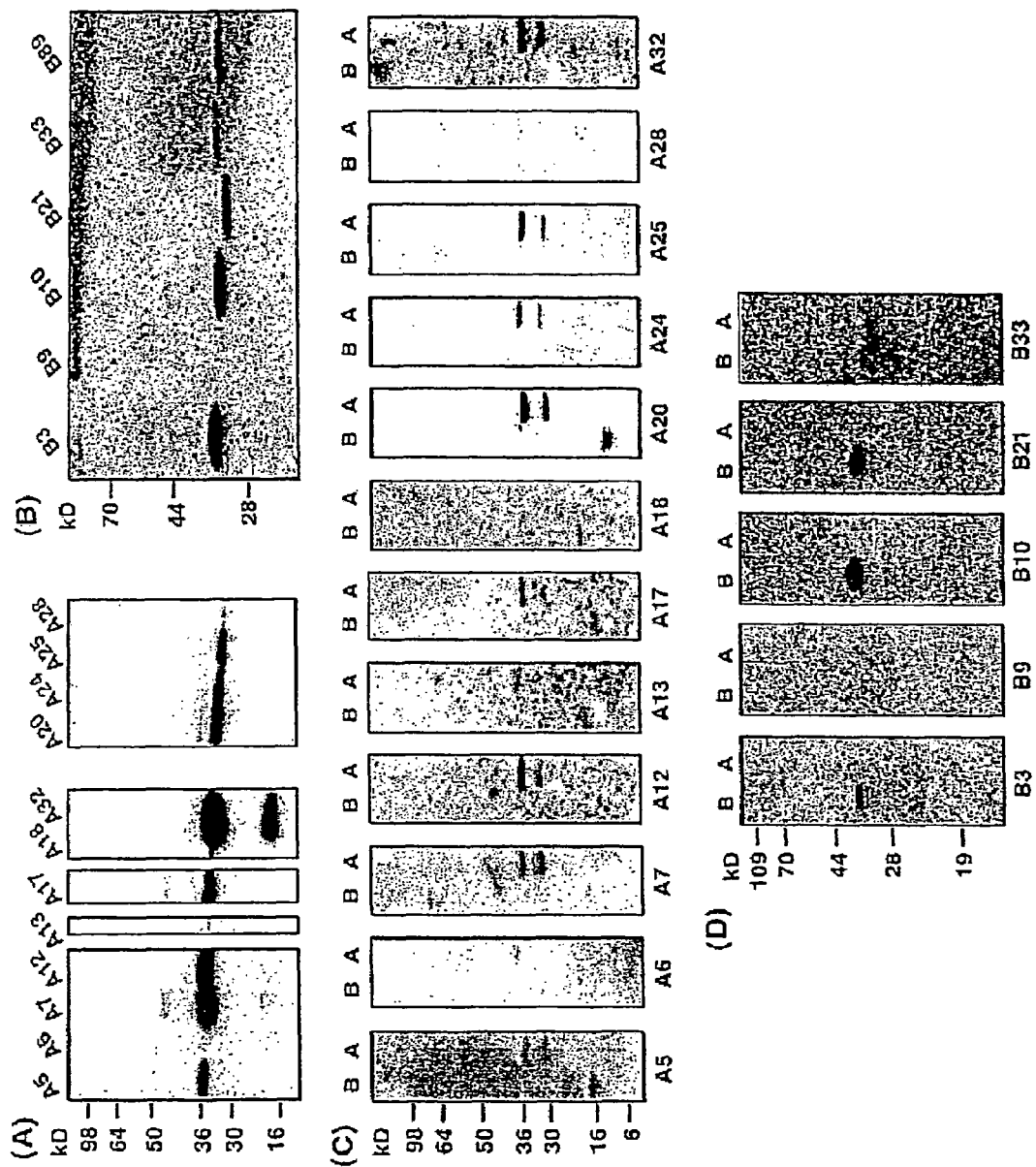
FIG. 3 shows the characterisation of the ICAbs by filter binding to antigen. scFv were cloned into the bacterial expression vector, pHEN2 and used to transform HB2151 *E. coli*. Periplasmic expression of scFv was obtained for anti-ABL (A) and anti-BCR (B) ICAbs. scFv were subjected to SDS-PAGE followed by Western blotting. The scFv were tagged with c-myc epitope and visualised using 9E10 monoclonal anti-myc tag antibody and secondary HRP-conjugated anti-mouse antibody. (C, D) The specificity of the scFv was evaluated in vitro by testing their ability to recognise filter-bound antigen (SH2 domain of ABL (C) and SH2-binding domain of BCR (D)). The antigens were separated by SDS-PAGE and transferred to filters which were incubated with scFv (bacterial periplasmic extracts) followed by 9E10 and HRP-conjugated anti-mouse antibodies for detection. Each scFv was tested against both ABL (designated A) and BCR (designated B) antigens.
Size marker positions are shown on the LHS of each panel.

The levels of expression of individual scFv were initially examined by bacterial periplasmic expression. The captured scFv were sub-cloned into the expression vector, pHEN2, which has the PelB leader sequence 5' to the scFv allowing periplasmic expression of soluble scFv protein and in-frame with histidine and myc epitope-tags. Periplasmic scFv extracts were Western blotted using anti-myc tag antibody, 9E10 for immuno-detection (FIG. 3A, B). Variable levels of protein are expressed. The best anti-ABL scFv (FIG. 3A) levels were found for A32 whereas much lower levels of protein could be detected for A6, for instance. Similarly anti-BCR scFv exhibited variability in expression, B 10 was the highest expressed antibody fragment whereas B9 and B33 were present at lower levels (FIG. 3B). These variations may reflect differences in folding characteristics and may additionally be due to codon preferences for the human scFv in bacteria.

Example 8

In Vitro Interaction of ICAbs with Antigen

Antibody specificity was investigated by comparing the ability of the scFv to discriminate between BCR and ABL antigens when these were immobilised on membranes. Various periplasmic scFv were tested for binding to bacterially synthesised BCR and ABL antigens of comparable size and levels (FIG. 3C, D). The binding of scFv to the relevant antigens paralleled the level of periplasmic expression. In the anti-ABL panel, scFv A32 had quantitatively the best interaction with ABL protein in keeping with its efficient expression, whereas A6 weakly detected antigen presumably due to the low level of scFv. In most cases, we observed discrimination by the scFv between the two antigens except for A20 which appears to cross-react with both ABL and BCR antigens, although the BCR antigen may be a degraded form given the size is around 16 Kda rather than around 30 Kda for inIACT antigen.

Like the anti-ABL scFv, there was a clear relationship between degree of binding of anti-BCR scFv to BCR SH2 binding domain protein and the level of periplasmic expression (FIG. 3D). The specificity was demonstrated by the lack of binding of the scFv to the SH2 domain of the ABL protein (amino acids 26-348) on the same blot (FIG. 3D). Therefore when periplasmic scFv is prepared from the scFv selected using the ICA technology, most of the antibodies exhibit specific antigen recognition in vitro as well as in vivo.

Example 9

In Vivo Interaction of the Isolated scFv with Target Antigen in Mammalian Cells

Figure 4:
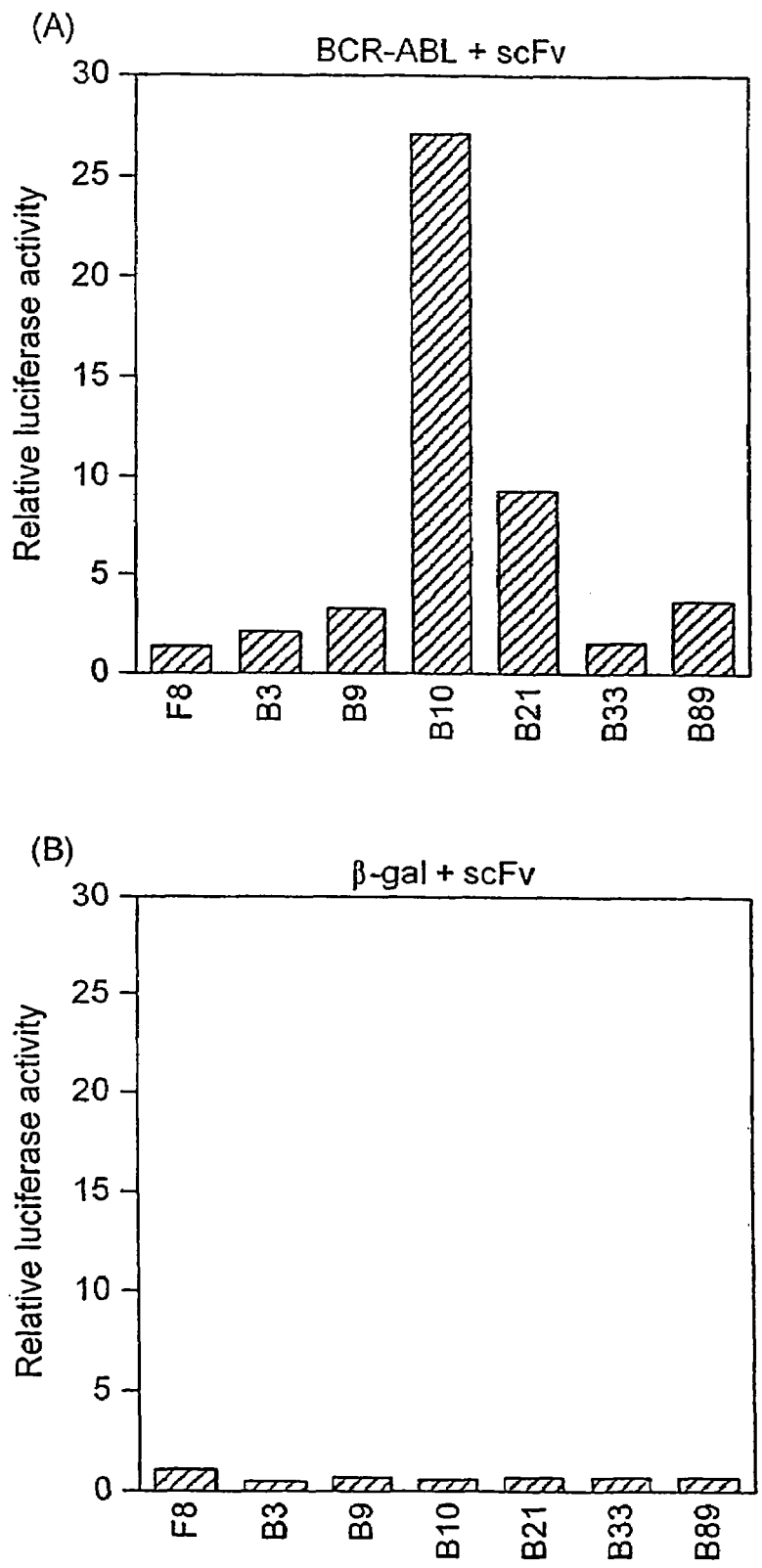
FIG. 4 shows a Mammalian antibody-antigen in vivo interaction assay.
CHO cells were transfected with a luciferase reporter, an antigen bait and an anti-BCR scFv fused to VP16 activation domain. As a negative control the non-relevant scFv F8 was used and a control bait was beta-gal in B.
(A) CHO cells were transiently transfected with a Firefly luciferase reporter plasmid together with an internal *Renilla luciferase* control plasmid pRL-CMV, the bait plasmid pM3-E1A2 and one of the anti-BCR scFv-VP16 expression plasmids, as indicated. The luciferases levels were assayed 48 hours after transfection using the Dual Luciferase Assay System (Promega) and a luminometer. Firefly luciferase level from each transfection was normalised to the Ranilla luciferase level (internal control for the transfection efficiency). As a non-specific control, scFvF8-VP16, a non-relevant anti-AMCV scFv, expression plasmid was co-transfected with pM3-E1A2, plus the luciferase reporter. The relative Firefly luciferase level for each scFv tested was shown in the histogram with the level for scFvF8 taken as 1.

Our data show that the TAC technology can be used to develop a set of ICAbs which show in vivo antigen binding and specificity for antigen. In our previous work in which we developed the antibody-antigen interaction screen (Visintin, M., Tse, E., Axelson, H., Rabbitts, T. H. and Cattaneo, A. (1999) Proc. Natl. Acad. Sci. USA 96 11723-11728; Tse, E, Chung, G & Rabbitts, T. H; K. Turksen, Editor, 2000. Humana Press: Totawa), we also showed that the mammalian reporter assays could be used to assess the efficacy of ICAbs. This was emulated by testing the interaction of anti-BCR scFv with antigen measured by activation of a luciferase reporter gene. The scFv were cloned into the mammalian prey luciferase vector and the BCR-ABL bait cloned into pM3 (Sadowski, I. Bell, B Broad, P & Hollis, M (1992), Gene 118, 137-141). These were co-transfected into CHO cells with a standard Renilla luciferase to control for transfection levels. Variable levels of activation was observed when the target antigen used was BCR-ABL (FIG. 4A) but none when a non-relevant antigen beta-gal was used (FIG. 4B). The best activation level was consistently found with the scFv B10. No activation was observed with the BCR-ABL bait and an irrelevant scFv F8 (Tavladoraki, P., Benvenuto, B., Trinca, S., De Martinis, D., Cattaneo, A. & Galeffi, P. (1993) Nature (London) 366, 469 72.

Example 10

Sequence Comparison of the Selected Intracellular Antibodies

A comparison of the panels of scFv selected by the JAC technology was made by determination of the nucleotide sequences and translating into the corresponding amino acid sequence (FIG. 5). Eighteen ICAbs are aligned (six anti-BCR and twelve anti-ABL) and consensus sequences were derived for both the heavy chain ($V_H$) and light chain ($V_L$) variable regions. These sequence data were compared.

Figure 5B:
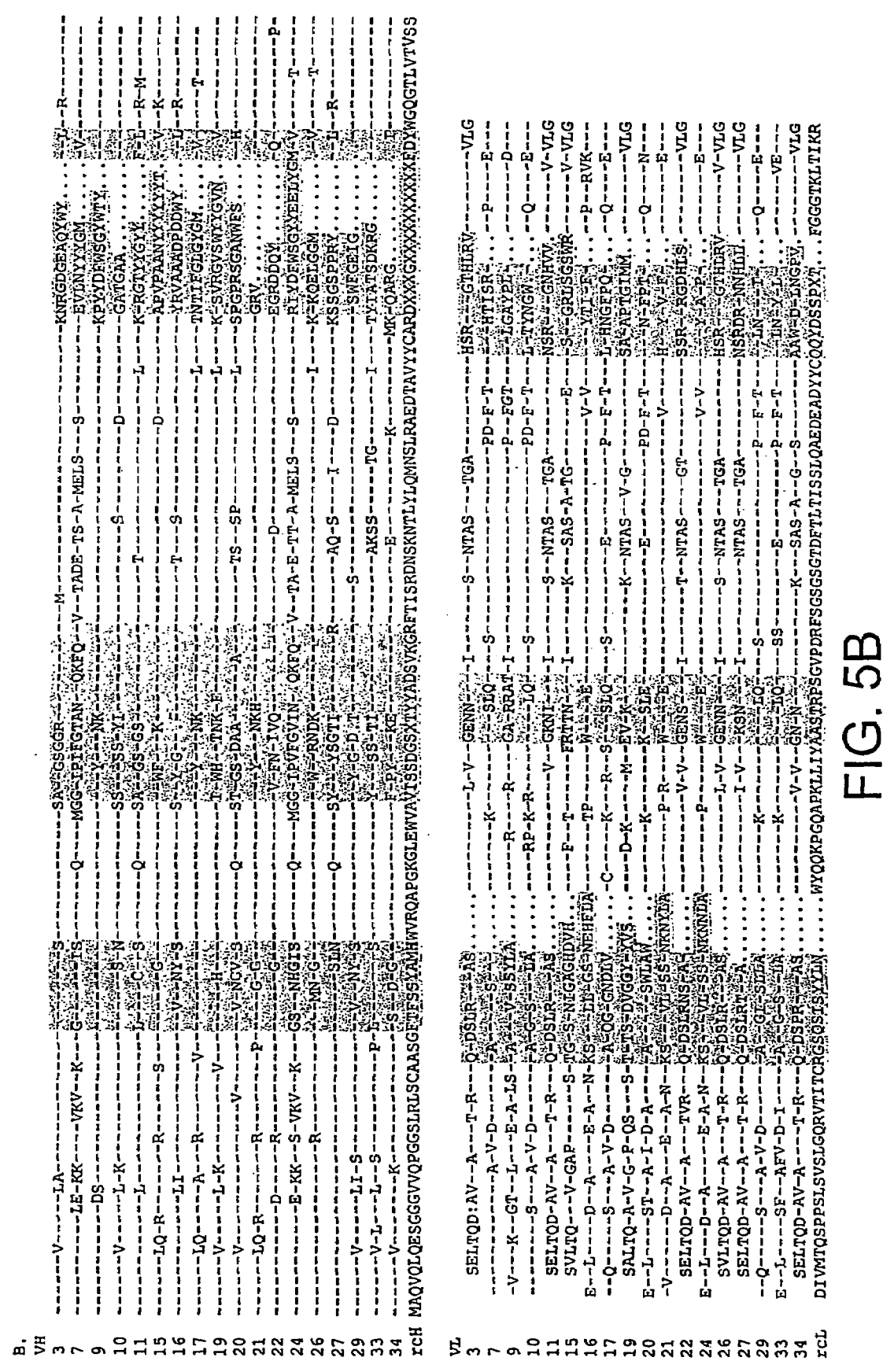

Most of the VH segments in the ICAb panel fall in the VHIII subgroup joined to the JH5 region. This in part reflects the initial bias in the phage library (Sheets, M. D et al (1998). Proc. Nat Acad Sci USA 95, 6157-6162) although the random scFv, but not selected ones, have representatives of other sub-groups (FIG. 5 A and B and MNLC unpublished). It was possible to obtain a consensus for both the selected and random scFv in the complementarity determining regions CDR1 and CDR2 but CDR3 differed strongly in sequence and length, reflecting the known importance of CDR3 in antibody combining sites (Xu, J. L & Davis, M. M. (2000), Immunity 13, 37-45). The IAC VHIII consensus matches the Kabat consensus (Kabat, B, A Wu, T. T., Perry, H. M., Gottesman, K. S, & Foeller, C., Sequences of Proteins of Biological Interest, 5$^{th}$ Ed, 1991. Bethesda: National Institute of Health) at all positions in the frameworks, except residue 3 (residue 1 in the Kabat consensus) which is a glutamine rather than glutamic acid residue (FIG. 5A). The residues at each framework position which vary amongst the IACbs are more restricted than in individual VII genes 29 and further the CDR1/2 conservation argues for limited acceptance of changes at this position compatible with intracellular activity. Indeed, we have isolated seFv with identical frameworks in antigen-specific ICAbs which differ by only three residues in CDR1. The VHIII framework is therefore amenable for intracellular expression, solubility and function and the contribution of non-randomised CDR1 and CDR2 is also apparent. Detailed mutagenesis studies could reveal additional changes which might facilitate greater intracellular efficacy but the VHIII consensus discussed here provides at least one backbone on which to build CDR variability for future IAC use. The L chain variable region in the anti-BCR and anti-ABL ICAb set also allows derivation of a consensus, in this case a match to the VkI subgroup (FIG. 5A) linked to JkI. Unlike the VII, we were able to obtain consensuses for all three CDR regions. Comparison of the ICAb VL consensus with that obtained from random scFv from the library (FIG. 5B) shows that the latter display greater overall variability. Each. residue differing between the two are the same in the ICAb VkI consensus as in the VkI consensus according to the Kabat database, indicating that the ICAb consensus is conserved and can provide the backbone for scFv VL sequences for intracellular use.

Strategy (B)

Example 11

Selection of Functional Intracellular Antibodies by IACT

Methods

Deletion mutants of the protein associated with the TAU microtubules were engineered as described in (Fasulo, L. et al. 1996 and Fasulo, L. et al. 2000) and cloned in the pBTM116 vector in the EcoRI-BamHI restriction sites. The non-immune library of antibody fragments displayed on the surface of the M13 filamentous phage was used for selecting antibodies (Sheets et al. 1998). The 15 1-421 fragment of the TAU protein was cloned in the pMAL-c2 vector (NEB) downstream of the malE gene. The same vector pMAL-c2 was used for producing the protein TAU 151-422. The proteins were purified according to protocols suggested by the manufacturer on an affinity column as described in (Kellerman, O. K. et al. 1982). The TAU human protein was purified from the bacterial strain BL21(DE3) as described in Kontsekova, E. et al 1995.

The non-immune library described in Sheets et al. 1998 was assayed with TAU 151-421 preadsorbed on the solid phase used for selection, according to a protocol described in Sblattero, D. et al. 2000. After 1 and 2 rounds of selection, some clones were isolated, and characterised by DNA amplification and fingerprinting of the gene coding for the scFv by digestion with BsTNI. The DNA isolated was then sequenced to confirm the diversity obtained.

The phagemid DNA was then isolated and cloned successively at the SfiI-NotI sites of the VP16 vector (Vojtek, A. B. et al. 1993) previously digested with the same restriction enzymes. The scFv-anti-TAU/VP16 ADI and ADII libraries were assayed successively against lexA-TAU as described in Visintin, M. et al. 1999 and Visintin, M. et al. 2001. 90% of the clones obtained grew in a histidine-free medium and became blue after the β-gal test. About a hundred clones coding for scFv anti-TAU were isolated from yeast following the method described in Visintin, M. et al. 2001, and the DNA isolated was analysed by BstNI fingerprinting and sequencing as described above. The individual clones were further tested against TAU by IACT.

The scFvs that proved positive after the latter analysis were then cloned in a phagemid expression vector, for the purpose of expressing the protein in soluble form. The proteins obtained were purified on an affinity column and analysed in gel filtration by means of a Superdex 75 column. The scFvs were then cloned successively in eukaryotic expression vectors, scFvexpress and nuclear scFvexpress (for expression of the scFvs in the nucleus) (Persic et al. 1997). The COS and CHO cell lines were transfected transiently according to the protocol described in Fasulo, L. et al. 1996 or following the protocol of the FuGENE6 reagent (Roche), used for transfecting the CHO cells. The cells were analysed 30-48 hours after transfection in immunofluorescence.

Sixteen scFvs df the original library Sheets et al. 1998 and twenty-five anti-TAU selected by IACT were sequenced, using an Epicentre Sequitherm Excel II kit. The L1-Cor 4000L automatic sequencer was used for automatic sequencing of the DNAs analysed.

Results

The technology developed by Visintin et al. 1999, IACT (intracellular antibody capture technology) (FIG. 2) and described in patent application PCT WO00/54057 was used for selecting antibodies for intracellular use against a panel of numerous different antigens. The example of selections against human TAU protein is described in detail here. TAU is a neuronal protein that belongs to the family of proteins that bind together the microtubules, and is a pathologic marker for Alzheimer's disease.

For the purpose of isolating antibodies using the IACT method, a fusion protein was engineered between a deletion mutant of human TAU protein (Ile151-Ser422) and maltose binding protein MBP (TAU-MBP). The protein expressed in E. coli is purified on a NiNTA affinity column, and is then used for in vitro preselection of a library of human antibody fragments (scFvs) expressed on phage (Sheets, M. D. et al.

Figure 2:
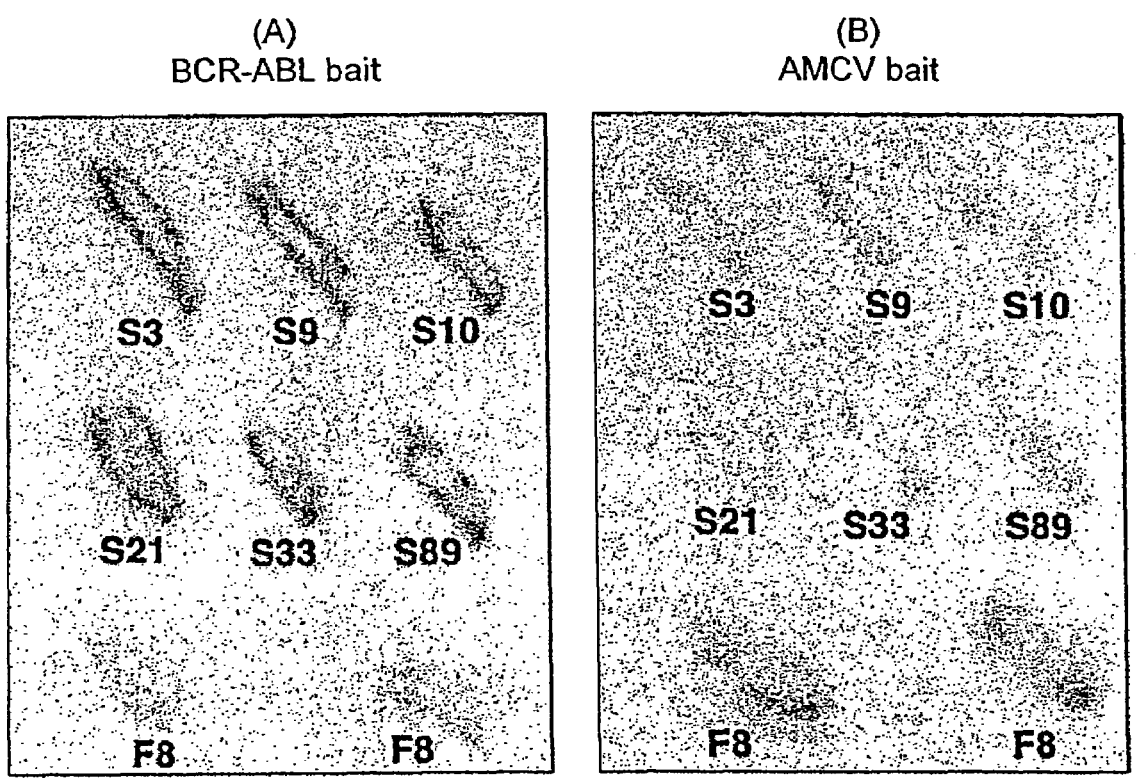
FIG. 2 shows β-galactosidase filter assay showing interaction between anti-BCR-specific scFv and BCR-ABL protein in yeast.
The L40 yeast strain was transformed with either a DNA binding domain bait fused to BCR-ABL (pBTM/E1A2) (A.) or the AMCV plant virus p41 coat-protein (B.) These host strains were transformed with plasmids coding for individual scFv-VPT6 activation domain fusions and streaked onto the YC medium lacking tryptophan and leucine to select for the plasmids. Interaction of scFv with bait protein was monitored by activation of β-galactosidase in the beta-gal filter assay shown. B3, 9, 10, 21, 33 and 89 are anti-BCR scFv and F8 is an scFv specific for the AMCV p41 protein (Tavladoraki, P., Benvenuto, B., Trinca, S., De Martinis, D., Cattaneo, A. & Galeffi, P. (1993) Nature (London) 366, 469-472). Interaction of the B series scFv only occurs with the BCR-ABL bait and not with AMCV, whereas F8 only interacts with AMCV.

1998) (FIG. 2, step 1). This step proved necessary for generating a heterogeneous population enriched in anti-TAU scFvs that might be compatible with the low efficiency of transformation of yeast. TAU-MBP was used for 2 successive rounds of in vitro preselection of the non-immune library of antibody fragments. The diversity of the library enriched in the first cycle of preselection and in the second cycle was quantified by analysis (100 clones per cycle) of the fingerprint after amplification of the DNAs coding for scFv with degenerated oligonucleotides (Sblattero, D. et al. 2000) and by sequencing some scFvs. After the first cycle, about 90% of the clones were found to be different, whereas after the second cycle only 13 clones out of 100 were found to be different (Table 1). Some clones of the first and of the second cycle were isolated and assayed in vitro in ELISA to verify the interaction with TAU. Three clones of the first cycle and 9 of the second were found to react with TAU in ELISA. These clones tested against other antigens (FIG. 3a) (MBP and BSA) were found to be TAU specific.

After this step, the library enriched in anti-TAU scFvs of the first and of the second cycle was cloned in the yeast expression vector VP 16 in order to create two libraries fused at the 5' of the activation domain of transcription, VP 16 (anti-TAU/VP16ADI and anti-TAU/VP16ADII). The anti-TAU/VP16ADI library consisted of $2.2 \times 10^6$ scFvs whereas the anti-TAU/VP16ADII library was formed from $6 \times 10^4$ scFvs.

For isolating anti-TAU scFvs in vivo, the libraries thus created were tested against a fusion protein between TAU (Ile151-Ser422) and the DNA-binding domain of the lexA protein (lexA-151-422TAU) (FIG. 2, step 2). The yeast transformed with these two sublibraries was first assayed for its prototrophy with histidine. $10^6$ clones grown in the absence of histidine were assayed successively for their ability to activate the lacZ gene (Visintin, M. et al. 2001). The DNA of some clones that were found to have a HIS3+ and lacZ+ phenotype were isolated and analysed by fingerprinting and then sequenced. In the screening of the anti-TAU/VP16ADI library, 31 different clones were isolated, whereas in the screening of the anti-TAU/VP16ADII library only 5 were isolated. Of these clones, only 17 (of the anti-TAU/VP16ADI library) and 3 (of the anti-TAU/VP16ADII library) (FIG. 3b, and Table 1) were confirmed positive after a second IACT screening. The specificity of these ICAbs for TAU was evaluated by co-transforming the anti-TAU scFvs with other antigens. It was found that the anti-TAUs selected with IACT did not cross-react with any of the antigens tested. Three anti-TAU scFvs were also expressed in *E. coli* and the soluble proteins isolated from the periplasm were tested in ELISA against TAU and two deletion mutants of TAU (FIG. 3c). All three scFvs were capable of interacting in vitro against TAU and its deletion mutants.

Four anti-TAU scFvs isolated at random from the starting library were tested in vivo with IACT against the TAU protein. These antibodies belong to the VHIII family: It was observed that none of these scFvs was capable of interacting in vivo with TAU protein. This result emphasises the fact that selection in vivo is necessary for obtaining intrabodies. Three anti-TAU's selected and validated with IACT were then analysed by biochemical techniques and studies of cell biology, for the purpose of verifying their solubility, tendency to aggregate and stability (Worn, A. et al. 1999). Analysis of the antibodies purified by gel filtration demonstrated that the three scFvs analysed occur for the most part in the elution peak corresponding to the monometric form of a scFv (FIG. 3d). The affinity of these three scFvs was calculated using competitive ELISA and in Biacore, and the kDa has a value that varies in the range 100-350 nM. The three scFvs expressed in vivo, in different cell lines (CHO, COS, PC 12) are highly soluble (FIG. 4), bind TAU and when the antibody fragments are expressed as fusion protein with a nuclear localisation signal, are capable of mislocalizing TAU in the nucleus, whenever this protein could be expressed as cytoplasmic protein (FIG. 5). It was found, moreover, that one of these scFvs recognises endogenous TAU in the PC12 neuronal cell line, and inhibits axon growth mediated by neurotrophin NGF (neuronal growth factor) (Melchionna et al. 2001).

Example 12

Analysis of the Sequences of Antibodies Isolated with IACT

Methods

The alignments and the analyses of the scFvs described above were evaluated in accordance with the Kabat database. A database was set up containing all the sequences of antibodies selected with IACT (VIDA, validated intrabody database). VIDA contains in particular the sequences of the anti-TAU antibodies described above. Furthermore, VIDA contains the sequences of validated intracellular antibodies described in the literature. The numbering of the amino acids of the antibodies (both of the VIDA sequences and of the sequences of the Kabat databank) was effected according to the Kabat scheme (Martin AC 1996; Deret S 1995), which was used for aligning all the sequences with one another. Numbering of the amino acids was effected automatically by means of the SeqTest program (Martin A. 1996). The frequency of each amino acid, for each position of the antibody chain, was determined.

The "consensus" (or the "consensus sequence"), for a given set of sequences, and limited to a certain subset of positions along the said sequences, is defined as the sequence

TABLE 1

Results of selection in vitro and in vivo. Number of positive clones of the monoreactive scFvs.

|  | Diversity of the anti-TAU polyclonal library | ELISA screening | Number of positive interactions after 1 screening with IACT | Number of different scFvs | Number of positive interactions after 2 screenings with IACT |
|---|---|---|---|---|---|
| Round 1 | 90/100 | 3/96 | ~$10^4$ | 31/100 | 17/31 |
| Round 2 | 13/100 | 9/96 | ~$10^5$ | 5/100 | 3/5 | in which, in the defined positions of the subset as above, the most frequently occurring amino acid is present. No amino acid is defined in the remaining positions.

For the purpose of carrying out an analysis of the sequences of antibodies present in VIDA, the said sequences are classified according to the species (mouse or human) from which they are derived, treating the $V_L$ and VH domains separately. The following 4 subsets are identified:

human VH: composed of 24 sequences
human VL: composed of 24 sequences mouse VH: composed of 12 sequences mouse VL: composed of 12 sequences.

The same type of subdivision was applied to the sequences of antibodies present in the Kabat databank (which are not generally tested with respect to intracellular expression) for the purpose of making, subsequently, comparisons between homogeneous sets.

Analysis of the antibody sequences contained in each subset of VIDA made it possible to identify a group of amino acid residues that are conserved. This group of residues is designated ICS (intrabody consensus sequence), and enables us to define 4 different ICSs (human ICS-VH, human ICS-VL, mouse ICS-VH, mouse ICS-VL). It is possible to define different ICSs, on the basis of a threshold of homology between the antibodies of each VIDA subset (absolute consensus, 90% consensus, etc.). For each reference group, the optimum ICS is obtained with the algorithm described below.

On the basis of the VIDA sequences, by induction, a procedure was elaborated that makes it possible to distinguish sequences of intrabodies from generic sequences of antibodies (separately for each subset of antibodies):

a) Calculate the consensus sequence for each VIDA subset, limiting the calculation to the positions in which the probability of the most frequent amino acid being found exceeds a predetermined threshold value LP (consensus threshold). These represent the Intrabody Consensus Sequences (ICS) and there is one for each VIDA subset.

b) Draw up two distributions for each of the four subsets of sequences identified previously. These distributions represent the identity number of each antibody of the VIDA dataset (green) or of the Kabat dataset (red) with respect to the ICS consensus sequence relating to that group (FIG. 10, column on right).

c) For each pair of distributions (red and green) if necessary introduce a measure of their "relative diversity". It is possible to use various definitions for measuring the degree of diversity D between the two distributions. We chose to measure D as the absolute value of the ratio between the difference of the mean values and the sum of the standard deviations of the two distributions in question. When this ratio is greater than 1 the distributions are considered to be different.

d) Repeat the procedure iteratively for different values of LP, determining the new distributions. Repeating the procedure with variation of LP (for example from a consensus threshold LP of 70% to a consensus threshold LP of 100%, in steps of 1-2%), for each of the four classes, it is possible to find the optimum value of LP that gives rise to the maximum value of D, i.e. that permits the best differentiation of the various distribution pairs (red and green). Hence, in general, we shall have a different LP value for each of the four VIDA subsets.

The procedure for identifying whether a given antibody, whose sequence does not already form a part of VIDA, is or is not an intrabody, is thus as follows: the sequences that differ from the ICS for a number of sites "compatible" with the VIDA distribution and not with the Kabat (FIG. 10 column on right) are intrabodies (intracellularly binding antibodies) (provided that the two distributions can actually be distinguished). The criterion of "compatibility" is established as follows: the number of different sites is compatible with VIDA and not with Kabat (b) when it is found to be lower than the mean value of the VIDA distribution to which the product between D and the standard deviation of VIDA is added. In practice, those sequences that differ from the ICS by less than the sequences already contained in VIDA differ from it, are considered to be intrabodies.

In general, it is to be expected that the optimum ICS depends on the size of the VIDA database. The procedure is in fact being refined progressively with increase in the number of sequences contained in the various VIDA subsets. It is possible, on the basis of the sequences already in our possession, to estimate the number of sequences required for reaching convergence on the optimum ICSs. It is thus a matter of estimating the number of sequences present in VIDA such that the optimum ICS obtained should not vary when new sequences are added. The estimate can be made on the assumption that new VIDA sequences conserve the same degree of variability of the sequences in our possession as at present. In particular, it is always possible to calculate ICS using just one part of the VIDA sequences. Assume that VIDA is composed of N sequences. It is possible to calculate ICS using just m<N sequences, and it can be done in Binomial (N, m) different ways. Then the average degree of homology can be measured between the ICSs calculated for each fixed m. This procedure enables us to understand whether the set of VIDA sequences at our disposal is large enough to saturate the average degree of homology between the ICSs as a function of m to an asymptotic value. This estimate calculated on the dataset currently available made it possible to conclude already that with the present size of VIDA we are not far from the asymptotic value.

Another way of observing the distribution of the antibody sequences consists of evaluating the probability of finding them by chance, assuming that the probability $P_i(A)$ of finding a certain amino acid A in position i does not depend on which amino acids there are in the other positions and is determined on the basis of the frequency of finding A in position i in the databank. For a given sequence s this value is written:

$$P_s = n \sqrt{\prod_{i=1}^{\infty} P_i(A_{s,i})}$$

in which $A_{s,i}$ is the amino acid in position i of sequence s. The infinite product can be extended to all the sites of the sequence, or can be limited to a subset.

Results

The 17 sequences of ICAbs selected with IACT (VIDA set) were compared with 16 scFv sequences extracted at random from the starting library (control set). All the VH domains of the VIDA set belong to the subgroup VH III (Deret, S. 1995) (Martin, A. C 1996), whereas 13 VL domains belong to the subgroup kappa 1 and 4 VL domains to kappa IV. In the control set as well, many of the sequences belong to the subgroup VH III (just one is different, belonging to VH II). In the VL domain, on the other hand, 10 sequences belong to the subgroup kappa I and 6 to lambda (mainly lambda IV). The average degree of homology between the sequences of the control set is 69% for the VH domain and 59% for the VL domain. The average homology within the VIDA set (85% for VH and 77% for VL) is greater than in the control set. Within the VIDA set, 76 amino acids in the VH domain (2 belonging to CDR 1, 2 belonging to CDR 2, 1 belonging to CDR 3), and 44 of the VL domain are conserved. The conserved amino acids define a consensus sequence that is characteristic of the intracellular antibodies (consensus ICS) both for the VH domain and for the VL domain (FIG. 11).

The first analysis undertaken gave a surprising and unexpected result. We assigned, to each VIDA and Kabat sequence, the $P_s$ calculated on the basis of the frequencies $P_i(A)$ in the Kabat subset (see Methods); at this point it became possible to compare the VIDA distributions with those of the corresponding Kabat subsets. If the comparison (and hence the infinite product present in the formula for $P_s$) is extended to the entire sequence, the two distributions VIDA and Kabat cannot be distinguished; the VIDA sequences in fact have values comparable with those obtained in the corresponding Kabat subset. If, however, we limit the comparison to just the sites of the respective ICS, then surprisingly the VIDA sequences are all disposed in the tail of the Kabat distribution with the highest probability (FIG. 12). This shows that the subset of residues defined by the ICS identifies a well-defined subpopulation of all the antibodies present in the Kabat database. This shows that the ICS is a good marker of the property of being an intracellular antibody.

This result was confirmed with another type of analysis. We measured the degree of homology between the ICS consensus sequences for the VH and VL domains and consensus sequences extracted from the Kabat databank (Kabat consensus sequences). Comparison was effected for the various subgroups defined in Table 2. All except 2 of the 76 amino acids conserved in the VH domain of the VIDA set coincide with the amino acids found with greatest frequency in the analogous position of the sequences of set No. 1 extracted from the Kabat databank. Furthermore, the two positions where coincidence is not confirmed between the two sets, are occupied in the VIDA set by amino acids (PHE in position 67 and ASN in position 73) that display a frequency only slightly lower than the most frequent ones in Kabat set No. 1 (VAL in position 67 and THR in position 73). Comparison of the ICS sequence with Kabat set No. 3 (subgroup VH III) shows that only GLN in position 1 is not found as frequently as GLU, whereas the agreement is perfect on all the other sites. On the other hand, 27 amino acids of the 76 conserved in the VIDA set do not coincide with the most frequent ones in Kabat set No. 2 (mouse VH), reflecting the species difference.

For the sequences of the VL domain, 47 of the 48 positions conserved in the VIDA set coincide with the most frequent amino acids of Kabat set No. 4 (formed from human VL sequences). Only 4 of the 48 residues belonging to the ICS sequence for the VL domain differ from those that are most frequent in Kabat set No. 5 (VL domains of mouse antibodies), whereas all 48 amino acids coincide with those found most frequently in Kabat set No. 6 (VL domains of subgroup Vk of human antibodies). Finally, 10 amino acids of the 48 of the ICS sequence do not coincide with those that are most frequent in Kabat set No. 7 (sequences of VL domains belonging to subgroup Vlambda of human antibodies).

TABLE 3

| VH | |
|---|---|
| No. 1 (human) | 2 |
| No. 2 (mouse) | 27 |
| No. 3 (human, subgroup VH III) | 1 |

TABLE 3-continued

| VL | |
|---|---|
| No. 4 (human) | 1 |
| No. 5 (mouse) | 3 |
| No. 6 (human, subgroup Vk) | 0 |
| No. 7 (human, subgroup Vλ) | 10 |

Number of amino acids in the VIDA set not coinciding with the consensus sequence of the Kabat subset shown in the column on the left (analysis limited to the positions defined by ICS).

Accordingly, the analysis described makes it possible to define a partial consensus sequence ICS for each variable antibody domain, which, a posteriori, in the positions where it is defined (i.e. in the positions where there is total conservation in the VIDA set), is found to coincide with the Kabat consensus sequences of the VL and VH domains of human antibodies.

It is interesting to clarify to what extent this characteristic (i.e. considerable homology with the sequence of greatest consensus in a significant, but not total, portion of the amino acids of the human VL and VH domains) occurs among the sequences of antibodies chosen at random from the Kabat databank. For this purpose we analysed the degree of homology of the sequences contained in the various subsets extracted from the Kabat relative to the respective consensus sequence, limiting the analysis to the positions in which the ICS consensus sequence defined above is defined (being 76 for the VH domain and 48 for the VL domain, see FIG. 13). This analysis shows that in the regions where there is greatest homology with the Kabat sequence of maximum consensus, the sequence density is limited, i.e. there are few antibodies in the Kabat database that are very similar to the Kabat consensus sequence. (It should be recalled that the Kabat consensus sequence is a virtual sequence.)

The degree of homology of the sequences of the VIDA set relative to the Kabat consensus sequences, evaluated for the appropriate subsets, is shown in FIG. 13, but only for the positions defined by ICS (see dots in FIG. 13). Surprisingly, the sequences of the VIDA set fall in the furthermost tail of these distributions, where there are few antibodies in the database itself. Accordingly, the sequences of the VIDA set (intracellular antibodies) show a high degree of homology with the consensus sequences of the Kabat subsets, a characteristic that is very rare for any antibody of the said database. Subsets No. 2 and No. 7 do not comply with this rule. This can be ascribed to the species difference (the VIDA set used for this analysis was derived from human antibodies) and the abundance of sequences of subgroup Vk in the VIDA set.

This analysis confirms that IACT leads to the selection of antibodies that are rare in the natural population of the said antibodies. The analysis also led to the identification of a subset of residues that appear to distinguish these antibodies from all the others (set of residues ICS). Furthermore, these intracellular antibodies have the remarkable property, which is defined operatively for the first time here, of having maximum similarity with the Kabat consensus sequence, if the analysis is restricted to the amino acid positions defined by ICS (FIG. 14, right).

This same analysis was performed on an extension of the VIDA set, to which were added sequences that derive from intracellular antibodies for different antigens. These analyses confirm the concept of capture of the consensus sequence by means of the IACT technique.

The set of intracellular antibodies selected with IACT, or in other words, which constitute VIDA, is subdivided into the following families (Table 2).

TABLE 2

List of subgroups of intrabodies

| scFv | VH | VL |
|---|---|---|
| Anti-β-gal | III | λ II |
| 1 ABL-BCR | III | λ III |
| 2 ABL-BCR | III | λ IV |
| 3 ABL-BCR | III | K I |
| 4 ABL-BCR | III | K I |
| 5 ABL-BCR | III | K IV |
| 6 ABL-BCR | III | K I |
| anti-tTG 2.18 | V | K I |
| anti-tTG 2.8 | V | K I |
| anti-tTG 3.7 | I | K I |
| anti-TAU #a | III | K I |
| anti-TAU #b | III | K I |
| anti-TAU #c | III | K I |
| anti-TAU #d | III | K IV |
| anti-TAU #e | III | K I |
| anti-TAU #f | III | K I |
| anti-TAU #g | III | K I |
| anti-TAU #k | III | K IV |
| anti-TAU #m | III | K IV |
| anti-TAU #n | III | K IV |
| anti-TAU #o | III | K I |
| anti-TAU #p | III | K I |
| anti-TAU #q | III | K I |
| anti-TAU #s | III | K I |
| anti-TAU #t | III | K I |
| anti-TAU #v | III | K IV |
| anti-TAU #x | III | K I |
| anti-TAU #y | III | K I |

Two important properties can be deduced from Table 2:
1) The VHIII family is far and away the most represented family. Obviously this reflects a bias in the libraries used, but more generally it reflects a higher average stability for antibodies of this family (Soderlind, E. et al. 2000). It demonstrates that in order to maximise the chances of a particular immunoglobulin to be capable of functioning within an intracellular environment, then an immunoglobulin of the VHIII family should be selected.
2) However, it is not sufficient to be VHIII in order to be a good intracellular antibody.

In fact, it has been seen before that anti-TAU antibodies of this family, isolated at random from the library, and with good properties of binding with TAU in vitro, are incapable of binding TAU in vivo.

The additional analysis, described in the Methods, was performed on the extension of the VIDA set. This analysis employs a new procedure for identifying a new intrabody. The results of the new procedure for identifying the intrabodies are presented in the following table.

TABLE 4

| Set | (number of sequences recognised as intrabody)/(total number of sequences in the set) |
|---|---|
| VH III human (ICS 81 sites, LP 90%, D 1.15) | |
| IACT | 23/24 |
| Kabat Subgroup VHIII | 122/1872 |
| VL human (ICS 29 sites, LP 96%, D 1.27) | |
| IACT | 24/24 |
| Kabat VL human | 299/2731 |

TABLE 4-continued

| Set | (number of sequences recognised as intrabody)/(total number of sequences in the set) |
|---|---|
| VH mouse (ICS 28 sites, LP 94%, D 1.34) | |
| IACT | 12/12 |
| Kabat VH mouse | 328/3353 |
| VL mouse (ICS 25 sites, LP 94%, D 1.15) | |
| IACT | 12/12 |
| Kabat VL mouse | 492/2518 |

This procedure, which leads to the identification of an optimum ICS and so limits the analysis to the positions identified by the ICSs themselves, was used first for identifying each antibody belonging to the said VIDA. By means of this procedure, constructed on the basis of the VIDA sequences in our possession, it is possible for all the VH sequences, and all but one of the VL sequences, to be identified as "intrabody". This provides a first validation of the procedure, which was then applied to the identification of potential intracellular antibodies in the Kabat database (FIG. 15, right). The procedure leads to the identification, as intracellular antibodies (identification defined in Methods), of a fraction that amounts to about 10% of the sequences of the various Kabat subsets (Table 4). These antibodies are potentially good intracellular antibodies, identified by the procedure in question.

A sample of these antibodies was assayed by IACT, as described above, to ascertain its effective stability in the intracellular environment. The results of this experimental verification demonstrated that effectively all the antibodies predicted to be good intracellular antibodies passed this experimental test. This result provides further validation of the ICS concept and of the procedure based on ICS for the identification of intracellular antibodies.

Next we verified the degree of homology of the ICS sequences that we had extracted (see Table 4) with the Kabat sequence of maximum consensus in the corresponding subset. The results are shown in Table 5.

TABLE 5

Homology of the ICS relative to the Kabat consensus

| Maximum Consensus ICS | VH III human | VH mouse | VL human | VL mouse |
|---|---|---|---|---|
| ICS VH III human (81 sites) | 80 | 52 | | |
| ICS VH mouse (29 sites) | 27 | 29 | | |
| ICS VL human (28 sites) | | | 28 | 28 |
| ICS VL mouse (25 sites) | | | 23 | 25 |

Finally we evaluated whether it is also possible to identify the VIDA sequences solely from their degree of homology relative to the Kabat sequence of maximum consensus, without limiting the analysis to the ICS positions, but on the entire sequence (FIG. 15, left). FIG. 15 shows that the procedure of the present invention is more selective compared with what can be done using an analysis of homology relative to the Kabat consensus, on the entire sequence. In fact, limiting the analysis to just the ICS sites (FIG. 15, right), it is found that a much lower number of Kabat sequences is compatible with the VIDA distribution of sequences.

The intrabody recognition procedure is robust with respect to insertion of new sequences in the VIDA set if LP is less than 100%. In fact, insertion of a new sequence would only alter the probability of finding the various amino acids in the various positions to an extent equal to 1/n, where n is the number of sequences in the VIDA set.

FIG. 15, right, shows another significant aspect: there is a significant number of sequences in the Kabat database having a homology relative to the Kabat consensus that is higher than the VIDA population. This means that if all the amino acid positions are analysed, the intracellular antibodies do not have maximum similarity with the Kabat consensus (FIG. 14, left), which is however the case if the analysis is restricted to just the sites defined by ICS (FIG. 14, right). It can be concluded from this that an antibody can be very similar to the Kabat consensus (maximum homology) and yet not be a good intracellular antibody (Knappik et al. 2000).

In order to be a good intracellular antibody it is necessary to have good homology with the Kabat consensus on the correct sites. The present invention, in addition to demonstrating this, has identified those sites on which the consensus should be calculated.

In conclusion, the description of this invention describes:
i) the development of a procedure for identifying an intracellular antibody, without the need to verify it experimentally, on the basis of the sequence alone.

ii) the use of this procedure on a database of sequences of experimentally validated intracellular antibodies led to the discovery of a set of key positions on the molecule of antibodies on which an ICS is defined, this discovery also being a part of this invention.

iii) the optimum ICS can be employed for designing and constructing a library that is very rich in functional intracellular antibodies.

All publications mentioned in the above specification, and references cited in said publications, are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. An intracellularly binding immunoglobulin molecule comprising: a variable heavy chain comprising the amino acid sequence of SEQ ID No 3; and a variable light chain.

2. A method of selectively binding an intracellularly binding immunoglobulin molecule to a ligand in an intracellular environment, the method comprising contacting the intracellularly binding immunoglobulin molecule comprising a variable heavy chain comprising the amino acid sequence of SEQ ID No 3 and a variable light chain, with BCR or BCR-ABL in an intracellular environment, wherein BCR or BCR-ABL is selectively bound by said molecule.

* * * * *

UNITED STATES PATENT AND TRADEMARK OFFICE
CERTIFICATE OF CORRECTION

PATENT NO.        : 7,608,453 B2                                   Page 1 of 1
APPLICATION NO. : 10/771257
DATED             : October 27, 2009
INVENTOR(S)       : Cattaneo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 482 days.

Signed and Sealed this

Twelfth Day of October, 2010

David J. Kappos
*Director of the United States Patent and Trademark Office*

SEQUENCE LISTING

```
<160> NUMBER OF SEQ ID NOS: 124

<210> SEQ ID NO 1
<211> LENGTH: 110
<212> TYPE: PRT
<213> ORGANISM: Artificial sequence
<220> FEATURE:
<223> OTHER INFORMATION: Consensus

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Lys Thr Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Gly Ser Leu Ser Tyr Tyr Tyr Tyr Pro
            100                 105                 110

<210> SEQ ID NO 2
<211> LENGTH: 101
<212> TYPE: PRT
<213> ORGANISM: Artificial sequence
<220> FEATURE:
<223> OTHER INFORMATION: Consensus

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Val Ser Ile
```

```
                    20                  25                  30
Ser Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser Arg
        50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Asn Ser
                85                  90                  95

Leu Pro Gln Trp Thr
            100

<210> SEQ ID NO 3
<211> LENGTH: 112
<212> TYPE: PRT
<213> ORGANISM: Artificial sequence
<220> FEATURE:
<223> OTHER INFORMATION: Consensus

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ser Val Ile Ser Gly Asp Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Trp Gly Gln Gly Thr Leu Val Thr Val Ser Ser
            100                 105                 110

<210> SEQ ID NO 4
<211> LENGTH: 108
<212> TYPE: PRT
<213> ORGANISM: Artificial sequence
<220> FEATURE:
<223> OTHER INFORMATION: Consensus

<400> SEQUENCE: 4

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Tyr Tyr
            20                  25                  30

Leu Asn Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Arg
                85                  90                  95

Thr Phe Gly Gln Gly Thr Lys Val Glu Ile Lys Arg
            100                 105
```

```
<210> SEQ ID NO 5
<211> LENGTH: 123
<212> TYPE: PRT
<213> ORGANISM: Homo sapiens

<400> SEQUENCE: 5

Gln Val Gln Leu Gln Glu Ser Gly Gly Gly Val Val Gln Pro Gly Gly
1               5                   10                  15

Ser Leu Arg Leu Ser Cys Glu Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp His Tyr Gly Ser Gly Ser Pro Ser Met Asp Tyr
            100                 105                 110

Trp Gly Gln Gly Thr Thr Val Thr Val Ser Ser
        115                 120

<210> SEQ ID NO 6
<211> LENGTH: 125
<212> TYPE: PRT
<213> ORGANISM: Homo sapiens

<400> SEQUENCE: 6

Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Cys
            20                  25                  30

Ala Met Thr Trp Val Arg Gln Ala Pro Gly Lys Gly Leu Glu Trp Val
        35                  40                  45

Thr Ser Ile Ser Asn Asp Gly Ser Asn Thr Tyr Tyr Ala Asp Ser Val
    50                  55                  60

Lys Gly Arg Phe Thr Val Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ser Ser Gly Trp Pro Ser Thr Arg Asn Ser Glu Val
            100                 105                 110

Asp Tyr Trp Gly Gln Gly Thr Leu Val Thr Val Ser Ser
        115                 120                 125

<210> SEQ ID NO 7
<211> LENGTH: 121
<212> TYPE: PRT
<213> ORGANISM: Homo sapiens

<400> SEQUENCE: 7

Gln Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Ser His Trp Ala Arg Gln Ala Pro Gly Lys Gly Leu Glu Trp Val
```

```
                    35                  40                  45
Ser Ala Ile Ser Gly Ser Gly Ser Asn Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Gly Tyr Ser Tyr Gly Ser Pro Asp Asp Tyr Trp Gly
            100                 105                 110

Gln Gly Thr Leu Val Thr Val Ser Ser
        115                 120

<210> SEQ ID NO 8
<211> LENGTH: 118
<212> TYPE: PRT
<213> ORGANISM: Homo sapiens

<400> SEQUENCE: 8

Gln Val Gln Leu Leu Gln Ser Gly Gly Gly Leu Val Gln Pro Gly Gly
 1               5                  10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
         35                  40                  45

Ser Ala Ile Ser Gly Asn Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Val Arg Gly Asp Gly Tyr Asn Ser Phe Asp Tyr Trp Gly Gln Gly Thr
            100                 105                 110

Leu Val Thr Val Ser Ser
        115

<210> SEQ ID NO 9
<211> LENGTH: 117
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Gly Tyr Asn Tyr Asp Tyr Trp Gly Gln Gly Thr Leu
            100                 105                 110

Val Thr Val Ser Ser
```

115

<210> SEQ ID NO 10
<211> LENGTH: 119
<212> TYPE: PRT
<213> ORGANISM: Homo sapiens

<400> SEQUENCE: 10

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Asp Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Arg Gly Gly Glu Val Val Asp Tyr Trp Gly Gln Gly
            100                 105                 110

Thr Leu Val Thr Val Ser Ser
            115

<210> SEQ ID NO 11
<211> LENGTH: 122
<212> TYPE: PRT
<213> ORGANISM: Homo sapiens

<400> SEQUENCE: 11

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Asn Ile Lys Gln Asp Gly Ser Glu Thr Tyr Val Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Ser Ser Gly Trp Tyr Phe His Ser Asp Tyr Trp
            100                 105                 110

Gly Gln Gly Thr Leu Val Thr Val Ser Ser
        115                 120

<210> SEQ ID NO 12
<211> LENGTH: 120
<212> TYPE: PRT
<213> ORGANISM: Homo sapiens

<400> SEQUENCE: 12

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met His Trp Val Arg Gln Ala Pro Gly Lys Gly Leu Glu Trp Val
            35                  40                  45

Ser Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Val Arg Arg Glu Lys Phe Glu Asp Tyr Trp Gly Gln
            100                 105                 110

Gly Thr Leu Val Thr Val Ser Ser
            115                 120

<210> SEQ ID NO 13
<211> LENGTH: 126
<212> TYPE: PRT
<213> ORGANISM: Homo sapiens

<400> SEQUENCE: 13

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ala Val Pro Arg Val Arg Gly Val Ile Ile Pro Glu
            100                 105                 110

Ser Asp Tyr Trp Gly Gln Gly Thr Leu Val Thr Val Ser Ser
            115                 120                 125

<210> SEQ ID NO 14
<211> LENGTH: 119
<212> TYPE: PRT
<213> ORGANISM: Homo sapiens

<400> SEQUENCE: 14

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Pro Asn Trp Ala His Phe Asp Phe Trp Gly Gln Gly
            100                 105                 110
```

```
Thr Leu Val Thr Val Ser Ser
        115

<210> SEQ ID NO 15
<211> LENGTH: 118
<212> TYPE: PRT
<213> ORGANISM: Homo sapiens

<400> SEQUENCE: 15

Gln Val Gln Leu Gln Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Ile Ile Tyr Ser Gly Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Val Arg Ser Ala Ala Glu Leu Asp Tyr Trp Gly Gln Gly Thr
            100                 105                 110

Leu Val Thr Val Ser Ser
        115

<210> SEQ ID NO 16
<211> LENGTH: 121
<212> TYPE: PRT
<213> ORGANISM: Homo sapiens

<400> SEQUENCE: 16

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Ala Leu Phe
65                  70                  75                  80

Leu Gln Met Asp Ser Leu Arg Ala Glu Asp Thr Ala Val Phe Tyr Cys
                85                  90                  95

Ala Lys Gly Gly Pro Arg Thr Thr Leu Thr Thr Ala Asp Tyr Trp Gly
            100                 105                 110

Gln Gly Thr Leu Val Thr Val Ser Ser
        115                 120

<210> SEQ ID NO 17
<211> LENGTH: 118
<212> TYPE: PRT
<213> ORGANISM: Homo sapiens

<400> SEQUENCE: 17

Gln Val Gln Leu Val Glu Ser Gly Gly Gly Leu Glu Gln Pro Gly Gly
1               5                   10                  15
```

-continued

Ser Leu Arg Leu Ser Cys Ala Ala Ser Gly Phe Thr Phe Ser Ser Tyr
                20                  25                  30

Ala Met Thr Trp Val Arg Gln Ala Pro Gly Lys Gly Leu Glu Trp Val
            35                  40                  45

Ser Ser Ile Gly Gly Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr His Cys
                85                  90                  95

Ala Glu Gly Asn Thr Gln Phe Gln His Asp Tyr Trp Gly Gln Gly Thr
                100                 105                 110

Leu Val Thr Val Ser Ser
        115

<210> SEQ ID NO 18
<211> LENGTH: 117
<212> TYPE: PRT
<213> ORGANISM: Homo sapiens

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ser Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ala Ser Pro Leu His Phe Asp Tyr Trp Gly Gln Gly Thr Leu
                100                 105                 110

Val Thr Val Ser Ser
        115

<210> SEQ ID NO 19
<211> LENGTH: 124
<212> TYPE: PRT
<213> ORGANISM: Homo sapiens

<400> SEQUENCE: 19

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Asn Tyr
                20                  25                  30

Ala Met Ser Trp Val Arg Gln Ala Pro Gly Lys Gly Leu Glu Trp Val
            35                  40                  45

Ser Val Ile His Asn Asp Gly Ser Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

```
Ala Arg Gly Ile Leu Glu Ser Gly Gly Ala Val Ala Gly Phe Gly Asp
            100                 105                 110

Tyr Trp Gly Gln Gly Thr Leu Val Thr Val Ser Ser
            115                 120

<210> SEQ ID NO 20
<211> LENGTH: 121
<212> TYPE: PRT
<213> ORGANISM: Homo sapiens

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Val Ser Gly Tyr
            20                  25                  30

Thr Met His Trp Val Arg Gln Ala Pro Gly Lys Gly Leu Glu Trp Val
            35                  40                  45

Ala Phe Ile Arg Lys Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asn Arg Gly Arg Ser Tyr Ser Met Glu Ser Asp Tyr Trp Gly
            100                 105                 110

Gln Gly Thr Leu Val Thr Val Ser Ser
            115                 120

<210> SEQ ID NO 21
<211> LENGTH: 119
<212> TYPE: PRT
<213> ORGANISM: Homo sapiens

<400> SEQUENCE: 21

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Phe Ile Arg Asn Asp Gly Ser Asn Glu Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Arg Ser Trp Tyr Tyr Phe Asp Tyr Trp Gly Gln Gly
            100                 105                 110

Thr Leu Val Thr Val Ser Ser
            115

<210> SEQ ID NO 22
<211> LENGTH: 124
<212> TYPE: PRT
<213> ORGANISM: Homo sapiens

<400> SEQUENCE: 22

Gln Val Gln Leu Val Glu Ser Gly Gly Gly Leu Ile Gln Pro Gly Gly
```

```
                1               5                   10                  15
Ser Leu Arg Leu Ser Cys Ala Ala Ser Gly Phe Thr Val Ser Ser Asn
                    20                  25                  30

Tyr Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Thr Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Leu Thr Tyr Tyr Tyr Gly Ser Gly Ser Ser His Leu Asp
                100                 105                 110

Tyr Trp Gly Gln Gly Thr Leu Val Thr Val Ser Ser
                115                 120
```

<210> SEQ ID NO 23
<211> LENGTH: 108
<212> TYPE: PRT
<213> ORGANISM: Homo sapiens

<400> SEQUENCE: 23

```
Gln Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Leu Leu Val Ile Tyr
                35                  40                  45

Gly Glu Asn Asn Gln Pro Ser Gly Ile Pro Phe Ser Gly Ser Ser Ser
            50                  55                  60

Gly Asn Thr Ala Ser Leu Thr Ile Thr Gly Ala Gln Ala Glu Asp Glu
65                  70                  75                  80

Ala Asp Tyr Tyr Cys His Ser Arg Asp Ser Ser Gly Thr His Leu Arg
                85                  90                  95

Val Phe Gly Gln Gly Thr Lys Leu Thr Val Leu Gly
                100                 105
```

<210> SEQ ID NO 24
<211> LENGTH: 108
<212> TYPE: PRT
<213> ORGANISM: Homo sapiens

<400> SEQUENCE: 24

```
Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
                20                  25                  30

Trp Tyr Gln Gln Lys Pro Gly Gln Ala Pro Leu Leu Val Ile Tyr Gly
                35                  40                  45

Lys Asn Ile Arg Pro Ser Gly Ile Pro Asp Arg Phe Ser Gly Ser Thr
            50                  55                  60

Ser Gly Asn Ser Ala Ser Leu Thr Ile Thr Gly Ala Gln Ala Glu Asp
65                  70                  75                  80

Glu Ala Asp Tyr Tyr Cys Asn Ser Arg Asp Arg Thr Gly Asn His Glu
                85                  90                  95

Glu Phe Gly Gly Gly Thr Lys Val Glu Ile Lys Arg
```

<210> SEQ ID NO 25
<211> LENGTH: 108
<212> TYPE: PRT
<213> ORGANISM: Homo sapiens

<400> SEQUENCE: 25

Asp Ile Val Met Thr Gln Ser Pro Ser Phe Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ser Tyr Tyr Cys Gln Lys Leu Asn Ser Tyr Pro Leu
                85                  90                  95

Thr Phe Gly Gly Gly Thr Lys Val Glu Ile Lys Arg
            100                 105

<210> SEQ ID NO 26
<211> LENGTH: 109
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15

Asp Thr Val Thr Ile Ala Cys Arg Ala Ser Arg Asp Ile Arg Asn Asp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Asp Ser Tyr Ser Pro
                85                  90                  95

Trp Thr Phe Gly Gln Gly Thr Lys Val Asp Ile Lys Arg
            100                 105

<210> SEQ ID NO 27
<211> LENGTH: 115
<212> TYPE: PRT
<213> ORGANISM: Homo sapiens

<400> SEQUENCE: 27

Asp Ile Val Met Thr Gln Ser Pro Ser Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Asn Trp Tyr Gln Gln Lys Pro Gly
        35                  40                  45

Gln Pro Pro Lys Leu Leu Ile Tyr Trp Ala Ser Thr Arg Glu Ser Gly
    50                  55                  60

```
Val Pro Asp Arg Phe Ser Gly Ser Gly Ser Gly Thr Asp Phe Thr Leu
 65                  70                  75                  80

Thr Ile Ser Ser Leu Gln Ala Glu Asp Val Ala Val Tyr Tyr Cys Gln
                 85                  90                  95

Gln Tyr Tyr Ser Thr Pro Arg Thr Phe Gly Gln Gly Thr Lys Val Glu
            100                 105                 110

Ile Lys Arg
        115

<210> SEQ ID NO 28
<211> LENGTH: 108
<212> TYPE: PRT
<213> ORGANISM: Homo sapiens

<400> SEQUENCE: 28

Asp Ile Val Met Thr Gln Ser Pro Ser Ser Leu Ser Ala Ser Val Gly
 1               5                  10                  15

Asp Arg Val Thr Ile Ser Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Ser Tyr Thr Thr Pro Arg
                 85                  90                  95

Thr Phe Gly Gln Gly Thr Lys Val Glu Ile Lys Arg
            100                 105

<210> SEQ ID NO 29
<211> LENGTH: 109
<212> TYPE: PRT
<213> ORGANISM: Homo sapiens

<400> SEQUENCE: 29

Glu Ile Val Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
                20                  25                  30

Leu Ala Trp Tyr Gln Gln Lys Ser Gly Lys Ala Pro Lys Leu Leu Ile
             35                  40                  45

Tyr Ala Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Phe Cys Gln Gln Tyr Lys Ser Ser Ser Pro
                 85                  90                  95

Trp Thr Ser Gly Gln Gly Thr Lys Val Glu Ile Lys Arg
            100                 105

<210> SEQ ID NO 30
<211> LENGTH: 110
<212> TYPE: PRT
<213> ORGANISM: Homo sapiens

<400> SEQUENCE: 30
```

```
Asn Phe Met Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Thr Val Ile Tyr
        35                  40                  45

Gly Glu Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65              70                  75                  80

Asp Glu Ala Asp Tyr Tyr Cys His Ser Arg Asp Ser Ser Gly Thr His
                85                  90                  95

Leu Arg Val Phe Gly Gly Gly Thr Lys Leu Thr Val Leu Gly
            100                 105                 110
```

<210> SEQ ID NO 31
<211> LENGTH: 108
<212> TYPE: PRT
<213> ORGANISM: Homo sapiens

<400> SEQUENCE: 31

```
Asn Phe Met Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Phe Ala
            20                  25                  30

Ser Trp Tyr Gln Gln Lys Pro Gly Gln Ala Pro Val Leu Leu Ile Tyr
        35                  40                  45

Gly Lys Asp Lys Arg Pro Ser Trp Thr Pro Asp Arg Phe Ser Val Ser
    50                  55                  60

Ser Ser Gly Asn Thr Ala Ser Leu Thr Ile Thr Gly Ala Gln Ala Glu
65              70                  75                  80

Asp Phe Ala Asp Tyr Tyr Cys Asn Ser Arg Asp Ser Ser Val Thr Cys
                85                  90                  95

Val Phe Gly Gly Gly Thr Lys Val Glu Ile Lys Arg
            100                 105
```

<210> SEQ ID NO 32
<211> LENGTH: 108
<212> TYPE: PRT
<213> ORGANISM: Homo sapiens

<400> SEQUENCE: 32

```
Asp Ile Val Met Thr Gln Ser Pro Ser Ser Leu Ser Ala Ser Val Gly
1               5                   10                  15

Asp Thr Val Thr Ile Thr Cys Arg Ala Ser Arg Ala Ile Ala Lys Tyr
            20                  25                  30

Leu Ala Trp Tyr Gln Gln Lys Pro Gly Lys Ala Pro Lys Pro Leu Ile
        35                  40                  45

Tyr Gly Ala Ser Thr Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Phe Cys Gln Gln Ala His Ser Phe Pro Pro
                85                  90                  95

Thr Phe Gly Gln Gly Thr Lys Val Glu Ile Lys Arg
            100                 105
```

```
<210> SEQ ID NO 33
<211> LENGTH: 108
<212> TYPE: PRT
<213> ORGANISM: Homo sapiens

<400> SEQUENCE: 33

Glu Ile Val Met Thr Gln Ser Pro Ser Ser Leu Ser Ala Ser Val Gly
1               5                   10                  15

Asp Arg Val Thr Ile Thr Cys Arg Ser Gln Ser Ile Ser Thr Tyr
            20                  25                  30

Leu Asn Trp Tyr Gln Glu Lys Pro Gly Lys Ala Pro Lys Leu Leu Val
            35                  40                  45

Tyr Asp Ala Ser Thr Leu His Arg Gly Ala Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Arg
                85                  90                  95

Thr Phe Gly Gly Leu Thr Lys Val Glu Ile Lys Arg
            100                 105

<210> SEQ ID NO 34
<211> LENGTH: 111
<212> TYPE: PRT
<213> ORGANISM: Homo sapiens

<400> SEQUENCE: 34

Asn Phe Met Leu Thr Gln Pro Arg Ser Val Ser Gly Ser Pro Gly Gln
1               5                   10                  15

Ser Val Thr Ile Ser Cys Thr Gly Thr Ser Arg Asp Val Gly Ala Tyr
            20                  25                  30

Asn His Val Ser Trp Tyr Gln Gln His Pro Gly Lys Ala Pro Lys Leu
            35                  40                  45

Leu Ile Tyr Glu Val Ser Lys Arg Pro Ser Gly Val Pro Asp Arg Phe
50                  55                  60

Ser Gly Ser Lys Ser Gly Asn Thr Ala Ser Leu Thr Val Ser Ser Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Gly Gly Thr Lys Leu Thr Val Leu Gly
            100                 105                 110

<210> SEQ ID NO 35
<211> LENGTH: 108
<212> TYPE: PRT
<213> ORGANISM: Homo sapiens

<400> SEQUENCE: 35

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Asn Tyr Ser Thr Pro Arg
                    85                  90                  95

Thr Phe Gly Gln Gly Pro Lys Val Asp Ile Asn Arg
                100                 105
```

<210> SEQ ID NO 36
<211> LENGTH: 108
<212> TYPE: PRT
<213> ORGANISM: Homo sapiens

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Ser Tyr Ser Ser Pro Arg
                85                  90                  95

Thr Phe Gly Gln Gly Thr Lys Val Glu Ile Lys Arg
                100                 105
```

<210> SEQ ID NO 37
<211> LENGTH: 110
<212> TYPE: PRT
<213> ORGANISM: Homo sapiens

<400> SEQUENCE: 37

```
Gln Ser Val Leu Thr Gln Asp Pro Ala Val Ser Val Ala Leu Gly Gln
1               5                   10                  15

Thr Val Lys Ile Thr Cys Gln Gly Asp Ser Leu Arg Ser Tyr Tyr Ala
                20                  25                  30

Ser Trp Tyr Gln Gln Lys Pro Gly Gln Ala Pro Val Thr Val Ile Tyr
            35                  40                  45

Gly Glu Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys His Ser Arg Asp Ser Ser Gly Thr His
                85                  90                  95

Leu Arg Val Phe Gly Gly Gly Thr Lys Leu Thr Val Leu Gly
                100                 105                 110
```

<210> SEQ ID NO 38
<211> LENGTH: 108
<212> TYPE: PRT
<213> ORGANISM: Homo sapiens

<400> SEQUENCE: 38

```
Asp Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30
```

```
Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Thr Asn Ser Ser Pro Arg
                 85                  90                  95

Thr Ser Gly Gln Gly Thr Lys Val Glu Ile Lys Arg
            100                 105
```

<210> SEQ ID NO 39
<211> LENGTH: 108
<212> TYPE: PRT
<213> ORGANISM: Homo sapiens

<400> SEQUENCE: 39

```
Glu Ile Val Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Ser Tyr
             20                  25                  30

Leu Asn Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Ala Tyr Tyr Cys Gln Gln Ser Tyr Arg Thr Pro Arg
                 85                  90                  95

Thr Phe Gly Gln Gly Thr Lys Val Glu Ile Lys Arg
            100                 105
```

<210> SEQ ID NO 40
<211> LENGTH: 108
<212> TYPE: PRT
<213> ORGANISM: Homo sapiens

<400> SEQUENCE: 40

```
Asp Ile Gln Met Thr Gln Ser Pro Ser Ala Leu Ser Ala Ser Val Gly
 1               5                  10                  15

Asp Arg Val Thr Ile Thr Cys Arg Ala Ser Gln Asn Ile Ala Asn Tyr
             20                  25                  30

Leu Asn Trp Tyr Gln Gln Lys Pro Gly Lys Pro Pro Lys Leu Leu Ile
         35                  40                  45

Tyr Val Ala Ser Asn Leu Pro Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Arg
                 85                  90                  95

Thr Phe Gly Gln Gly Thr Lys Val Glu Ile Lys Arg
            100                 105
```

<210> SEQ ID NO 41
<211> LENGTH: 132
<212> TYPE: PRT
<213> ORGANISM: Artificial sequence

```
<220> FEATURE:
<223> OTHER INFORMATION: Consensus
<220> FEATURE:
<221> NAME/KEY: MISC_FEATURE
<222> LOCATION: 5, 6, 9, 11, 13, 16, 30, 31, 33, 35, 39, 51..53, 55
      , 58..62
<223> OTHER INFORMATION: Xaa represents position at which no consensus
      could be assigned
<220> FEATURE:
<221> NAME/KEY: MISC_FEATURE
<222> LOCATION: 74, 75, 79, 80, 82..84, 88, 89, 97, 99, 101, 104..110,
      123, 124
<223> OTHER INFORMATION: Xaa represents position at which no consensus
      could be assigned
<220> FEATURE:
<221> NAME/KEY: MISC_FEATURE
<222> LOCATION: 36, 37, 56, 57, 111..121
<223> OTHER INFORMATION: Xaa may be present or absent

<400> SEQUENCE: 41

Gln Val Gln Leu Xaa Xaa Ser Gly Xaa Gly Xaa Val Xaa Pro Gly Xaa
1               5                   10                  15

Ser Leu Arg Leu Ser Cys Ala Ala Ser Gly Phe Thr Phe Xaa Xaa Tyr
            20                  25                  30

Xaa Met Xaa Xaa Xaa Trp Xaa Arg Gln Ala Pro Gly Lys Gly Leu Glu
        35                  40                  45

Trp Val Xaa Xaa Xaa Ser Xaa Xaa Xaa Xaa Xaa Xaa Xaa Xaa Tyr Tyr
    50                  55                  60

Ala Asp Ser Val Lys Gly Arg Phe Thr Xaa Xaa Arg Asp Asn Xaa Xaa
65                  70                  75                  80

Asn Xaa Xaa Xaa Leu Gln Met Xaa Xaa Leu Arg Ala Glu Asp Thr Ala
            85                  90                  95

Xaa Tyr Xaa Cys Ala Xaa Asp Xaa Xaa Xaa Xaa Xaa Xaa Xaa Xaa Xaa
            100                 105                 110

Xaa Xaa Xaa Xaa Xaa Xaa Xaa Xaa Xaa Trp Xaa Xaa Gly Thr Leu Val
            115                 120                 125

Thr Val Ser Ser
            130

<210> SEQ ID NO 42
<211> LENGTH: 115
<212> TYPE: PRT
<213> ORGANISM: Artificial sequence
<220> FEATURE:
<223> OTHER INFORMATION: Consensus
<220> FEATURE:
<221> NAME/KEY: MISC_FEATURE
<222> LOCATION: 1..4, 6, 9, 10, 12, 13, 15, 17, 19, 22, 24, 25, 27,
      34..38, 44
<223> OTHER INFORMATION: Xaa represents position at which no consensus
      could be assigned
<220> FEATURE:
<221> NAME/KEY: MISC_FEATURE
<222> LOCATION: 48, 49, 51, 52, 55, 56, 59..61, 66, 68, 76, 82, 83,
      85..87
<223> OTHER INFORMATION: Xaa represents position at which no consensus
      could be assigned
<220> FEATURE:
<221> NAME/KEY: MISC_FEATURE
<222> LOCATION: 89, 91, 93, 95..101, 108..113
<223> OTHER INFORMATION: Xaa represents position at which no consensus
      could be assigned
<220> FEATURE:
<221> NAME/KEY: MISC_FEATURE
<222> LOCATION: 28..33, 102..107
<223> OTHER INFORMATION: Xaa may be present or absent

<400> SEQUENCE: 42
```

```
Xaa Xaa Xaa Xaa Thr Xaa Ser Pro Xaa Xaa Leu Xaa Xaa Ser Xaa Gly
1               5               10                  15

Xaa Arg Xaa Thr Ile Xaa Cys Xaa Xaa Ser Xaa Xaa Xaa Xaa Xaa Xaa
            20              25                  30

Xaa Xaa Xaa Xaa Xaa Xaa Leu Ala Trp Tyr Gln Xaa Lys Pro Gly Xaa
        35                  40                  45

Xaa Pro Xaa Xaa Leu Ile Xaa Xaa Ala Ser Xaa Xaa Xaa Ser Gly Val
    50                  55                  60

Pro Xaa Arg Xaa Ser Gly Ser Gly Ser Gly Thr Xaa Phe Thr Leu Thr
65              70                  75                      80

Ile Xaa Xaa Leu Xaa Xaa Asp Xaa Ala Xaa Tyr Xaa Cys Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Thr Lys
    115
```

<210> SEQ ID NO 43
<211> LENGTH: 125
<212> TYPE: PRT
<213> ORGANISM: Homo sapiens

<400> SEQUENCE: 43

```
Met Ala Gln Val Gln Leu Val Glu Ser Gly Gly Gly Leu Ala Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Gly Arg Thr Tyr Tyr Ala Asp
    50                  55                  60

Ser Val Lys Gly Arg Phe Thr Met Ser Arg Asp Asn Ser Lys Asn Thr
65              70                  75                      80

Leu Tyr Leu Gln Met Asn Ser Leu Arg Ala Glu Asp Thr Ala Val Tyr
                85                  90                  95

Tyr Cys Ala Lys Asn Arg Gly Asp Gly Glu Ala Gln Tyr Trp Tyr Phe
            100                 105                 110

Asp Leu Trp Gly Arg Gly Thr Leu Val Thr Val Ser Ser
            115                 120                 125
```

<210> SEQ ID NO 44
<211> LENGTH: 123
<212> TYPE: PRT
<213> ORGANISM: Homo sapiens

<400> SEQUENCE: 44

```
Met Ala Gln Val Gln Leu Gln Glu Ser Gly Leu Glu Val Lys Lys Pro
1               5                   10                  15

Gly Gly Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Lys Asn Thr
65              70                  75                      80
```

```
Ala Tyr Met Glu Leu Ser Ser Leu Arg Ser Glu Asp Thr Ala Val Tyr
                85                  90                  95

Tyr Cys Ala Arg Glu Val Leu Asn Tyr Tyr Gly Met Phe Val Tyr
            100                 105                 110

Trp Gly Gln Gly Thr Leu Val Thr Val Ser Ser
        115                 120

<210> SEQ ID NO 45
<211> LENGTH: 126
<212> TYPE: PRT
<213> ORGANISM: Homo sapiens

<400> SEQUENCE: 45

Met Ala Gln Val Gln Leu Gln Glu Ser Gly Gly Asp Ser Val Gln Pro
1               5                   10                  15

Gly Gly Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Pro Tyr Tyr Asp Phe Trp Ser Gly Tyr Trp Thr Tyr
            100                 105                 110

Phe Asp Tyr Trp Gly Gln Gly Thr Leu Val Thr Val Ser Ser
        115                 120                 125

<210> SEQ ID NO 46
<211> LENGTH: 120
<212> TYPE: PRT
<213> ORGANISM: Homo sapiens

<400> SEQUENCE: 46

Met Ala Gln Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Ser Tyr Ser Met Asn Trp Val Arg Gln Ala Pro Gly Lys Gly Leu Glu
        35                  40                  45

Trp Val Ser Ser Ile Ser Ser Ser Ser Tyr Ile Tyr Tyr Ala Asp
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Asp Glu Asp Thr Ala Val Tyr
                85                  90                  95

Tyr Cys Ala Arg Gly Ala Thr Gly Ala Ala Phe Asp Tyr Trp Gly Gln
            100                 105                 110

Gly Thr Leu Val Thr Val Ser Ser
        115                 120

<210> SEQ ID NO 47
<211> LENGTH: 123
<212> TYPE: PRT
<213> ORGANISM: Homo sapiens
```

<400> SEQUENCE: 47

Met Ala Gln Val Gln Leu Gln Glu Ser Gly Gly Gly Leu Val Gln Pro
1               5                   10                  15

Gly Gly Ser Leu Arg Leu Ser Cys Ala Ala Ser Gly Leu Thr Phe Ser
            20                  25                  30

Ser Cys Ala Met Ser Trp Val Arg Gln Ala Pro Gly Gln Gly Leu Glu
        35                  40                  45

Trp Val Ser Ala Ile Ser Ser Gly Gly Ser Thr Tyr Tyr Ala Asp
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Leu Tyr
                85                  90                  95

Tyr Cys Ala Lys Asp Arg Gly Thr Tyr Tyr Gly Tyr Tyr Phe Asp Leu
            100                 105                 110

Trp Gly Arg Gly Met Leu Val Thr Val Ser Ser
        115                 120

<210> SEQ ID NO 48
<211> LENGTH: 127
<212> TYPE: PRT
<213> ORGANISM: Homo sapiens

<400> SEQUENCE: 48

Met Ala Gln Val Gln Leu Leu Gln Ser Arg Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Gly Met His Trp Val Arg Gln Ala Pro Gly Lys Gly Leu Glu
        35                  40                  45

Trp Val Ala Val Ile Trp Phe Asp Gly Ser Lys Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Asp Glu Asp Thr Ala Val Tyr
                85                  90                  95

Tyr Cys Ala Arg Ala Pro Val Pro Ala Ala Asn Tyr Tyr Tyr Tyr
            100                 105                 110

Tyr Thr Asp Val Trp Gly Lys Gly Thr Leu Val Thr Val Ser Ser
        115                 120                 125

<210> SEQ ID NO 49
<211> LENGTH: 125
<212> TYPE: PRT
<213> ORGANISM: Homo sapiens

<400> SEQUENCE: 49

Met Ala Gln Val Gln Leu Gln Glu Ser Gly Gly Gly Leu Ile Gln Pro
1               5                   10                  15

Gly Gly Ser Leu Arg Leu Ser Cys Ala Ala Ser Gly Phe Thr Val Ser
            20                  25                  30

Ser Asn Tyr Met Ser Trp Val Arg Gln Ala Pro Gly Lys Gly Leu Glu
        35                  40                  45

Trp Val Ser Val Ile Tyr Ser Gly Gly Ser Thr Tyr Tyr Ala Asp Ser
    50                  55                  60

Val Lys Gly Arg Phe Thr Ile Ser Arg Asp Thr Ser Lys Asn Ser Leu

```
                65                  70                  75                  80
Tyr Leu Gln Met Asn Ser Leu Arg Ala Glu Asp Thr Ala Val Tyr Tyr
                85                  90                  95

Cys Ala Arg Tyr Arg Val Ala Ala Asp Pro Asp Trp Tyr Phe
                100                 105                 110

Asp Leu Trp Gly Arg Gly Thr Leu Val Thr Val Ser Ser
            115                 120                 125

<210> SEQ ID NO 50
<211> LENGTH: 124
<212> TYPE: PRT
<213> ORGANISM: Homo sapiens

<400> SEQUENCE: 50

Met Ala Gln Val Gln Leu Leu Gln Ser Gly Gly Gly Val Ala Gln Pro
1               5                   10                  15

Gly Arg Ser Leu Arg Leu Ser Cys Ala Val Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Leu Tyr
                85                  90                  95

Tyr Cys Ala Thr Asn Thr Ile Phe Gly Leu Gly Tyr Gly Met Phe Val
            100                 105                 110

Tyr Trp Gly Gln Gly Thr Leu Val Thr Val Ser Ser
        115                 120

<210> SEQ ID NO 51
<211> LENGTH: 125
<212> TYPE: PRT
<213> ORGANISM: Homo sapiens

<400> SEQUENCE: 51

Met Ala Gln Val Gln Leu Val Glu Ser Gly Gly Gly Leu Val Lys Pro
1               5                   10                  15

Gly Gly Ser Leu Arg Leu Ser Cys Val Ala Ser Gly Phe Thr Phe Ser
            20                  25                  30

Ser His Ala Met His Trp Val Arg Gln Ala Pro Gly Lys Gly Leu Glu
        35                  40                  45

Trp Val Ala Ile Ile Trp His Asp Gly Thr Asn Lys Tyr Phe Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Leu Tyr
                85                  90                  95

Tyr Cys Ala Lys Asp Ser Val Arg Gly Val Ser Trp Tyr Tyr Gly Val
            100                 105                 110

Asn Val Trp Gly Gln Gly Thr Leu Val Thr Val Ser Ser
        115                 120                 125

<210> SEQ ID NO 52
<211> LENGTH: 125
<212> TYPE: PRT
```

<213> ORGANISM: Homo sapiens

<400> SEQUENCE: 52

Met Ala Gln Val Gln Leu Val Glu Ser Gly Gly Gly Val Val Gln Pro
1               5                   10                  15

Gly Gly Ser Leu Arg Val Ser Cys Ala Ala Ser Gly Phe Thr Val Ser
            20                  25                  30

Asn Cys Val Met Ser Trp Val Arg Gln Ala Pro Gly Gln Gly Leu Glu
        35                  40                  45

Trp Val Ser Thr Ile Gly Ser Asp Ala Ala Thr Tyr Tyr Ala Asp
    50                  55                  60

Ser Ala Lys Gly Arg Phe Thr Ile Ser Arg Asp Thr Ser Lys Asn Ser
65                  70                  75                  80

Pro Tyr Leu Gln Met Asn Ser Leu Arg Ala Glu Asp Thr Ala Leu Tyr
                85                  90                  95

Tyr Cys Ala Ser Pro Gly Pro Arg Ser Gly Ala Asn Trp Phe Ser Phe
            100                 105                 110

Asp His Trp Gly Gln Gly Thr Leu Val Thr Val Ser Ser
        115                 120                 125

<210> SEQ ID NO 53
<211> LENGTH: 117
<212> TYPE: PRT
<213> ORGANISM: Homo sapiens

<400> SEQUENCE: 53

Met Ala Gln Val Gln Leu Leu Gln Ser Arg Gly Gly Val Val Gln Pro
1               5                   10                  15

Gly Arg Ser Leu Arg Leu Ser Cys Ala Ala Pro Gly Phe Thr Phe Ser
            20                  25                  30

Gly Tyr Gly Met His Trp Val Arg Gln Ala Pro Gly Lys Gly Leu Glu
        35                  40                  45

Trp Val Ala Val Ile Ser Tyr Asp Gly Ser Asn Lys His Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Arg Val Phe Asp Tyr Trp Gly Gln Gly Thr Leu
            100                 105                 110

Val Thr Val Ser Ser
        115

<210> SEQ ID NO 54
<211> LENGTH: 121
<212> TYPE: PRT
<213> ORGANISM: Homo sapiens

<400> SEQUENCE: 54

Met Ala Gln Val Gln Leu Gln Glu Ser Gly Asp Val Val Gln Pro
1               5                   10                  15

Gly Arg Ser Leu Arg Leu Ser Cys Ala Ala Ser Gly Phe Thr Phe Ser
            20                  25                  30

Ser Tyr Gly Met His Trp Val Arg Gln Ala Pro Gly Lys Gly Leu Glu
        35                  40                  45

Trp Val Ala Val Ile Ser Phe Asn Gly Ile Val Gln Tyr Tyr Ala Asp
    50                  55                  60

```
Ser Val Lys Gly Arg Phe Thr Ile Ser Arg Asp Asn Ser Lys Asp Thr
 65                  70                  75                  80

Leu Tyr Leu Gln Met Asn Ser Leu Arg Ala Glu Asp Thr Ala Val Tyr
                 85                  90                  95

Tyr Cys Ala Arg Glu Gly Arg Asp Asp Gln Tyr Phe Gln Tyr Trp Gly
            100                 105                 110

Gln Gly Thr Leu Val Thr Val Pro Ser
            115                 120
```

<210> SEQ ID NO 55
<211> LENGTH: 128
<212> TYPE: PRT
<213> ORGANISM: Homo sapiens

<400> SEQUENCE: 55

```
Met Ala Gln Val Gln Leu Gln Glu Ser Gly Gly Glu Val Lys Lys Pro
 1               5                  10                  15

Gly Ser Ser Val Lys Val Ser Cys Lys Ala Ser Gly Gly Ser Phe Ser
                 20                  25                  30

Asn His Gly Ile Ser Trp Val Arg Gln Ala Pro Gly Gln Gly Leu Glu
             35                  40                  45

Trp Met Gly Gly Ile Ile Pro Val Phe Gly Val Ile Asn Tyr Gln Lys
     50                  55                  60

Phe Gln Gly Arg Val Thr Ile Thr Ala Asp Glu Ser Thr Thr Thr Ala
 65                  70                  75                  80

Tyr Met Glu Leu Ser Ser Leu Arg Ser Glu Asp Thr Ala Val Tyr Tyr
                 85                  90                  95

Cys Ala Arg Arg Ile Tyr Asp Phe Trp Ser Gly Tyr Tyr Glu Glu Leu
            100                 105                 110

Tyr Gly Met Asp Val Trp Gly Gln Gly Thr Thr Val Thr Val Ser Ser
            115                 120                 125
```

<210> SEQ ID NO 56
<211> LENGTH: 121
<212> TYPE: PRT
<213> ORGANISM: Homo sapiens

<400> SEQUENCE: 56

```
Met Ala Gln Val Gln Leu Gln Glu Ser Gly Gly Gly Val Val Gln Pro
 1               5                  10                  15

Gly Arg Ser Leu Arg Leu Ser Cys Ala Ala Ser Gly Phe Thr Phe Met
                 20                  25                  30

Asn Tyr Gly Met His Trp Val Arg Gln Ala Pro Gly Lys Gly Leu Glu
             35                  40                  45

Trp Val Ala Val Ile Trp Ser Asp Arg Asn Asp Lys Tyr Tyr Ala Asp
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Ile Tyr
                 85                  90                  95

Tyr Cys Ala Lys Asp Lys Gln Glu Leu Gly Gly Met Asp Val Trp Gly
            100                 105                 110

Gln Gly Thr Thr Val Thr Val Ser Ser
            115                 120
```

<210> SEQ ID NO 57

<211> LENGTH: 122
<212> TYPE: PRT
<213> ORGANISM: Homo sapiens

<400> SEQUENCE: 57

Met Ala Gln Val Gln Leu Gln Glu Ser Gly Gly Gly Val Val Gln Pro
1               5                   10                  15

Gly Gly Ser Leu Arg Leu Ser Cys Ala Ala Ser Gly Phe Thr Phe Ser
            20                  25                  30

Ser Tyr Ser Leu Asn Trp Val Arg Gln Ala Pro Gly Gln Gly Leu Glu
        35                  40                  45

Trp Val Ser Tyr Ile Ser Ser Tyr Ser Gly Thr Ile Tyr Tyr Ala Asp
50                  55                  60

Ser Val Lys Gly Arg Phe Thr Ile Ser Arg Asp Asn Ala Gln Asn Gln
65                  70                  75                  80

Leu Tyr Leu Gln Ile Asn Ser Leu Arg Asp Glu Asp Thr Ala Val Tyr
                85                  90                  95

Tyr Cys Ala Lys Ser Ser Gly Ser Pro Pro Arg Tyr Phe Asp Leu Trp
            100                 105                 110

Gly Arg Gly Thr Leu Val Thr Val Ser Ser
        115                 120

<210> SEQ ID NO 58
<211> LENGTH: 119
<212> TYPE: PRT
<213> ORGANISM: Homo sapiens

<400> SEQUENCE: 58

Met Ala Gln Val Gln Leu Val Glu Ser Gly Gly Gly Leu Ile Gln Pro
1               5                   10                  15

Gly Gly Ser Leu Arg Leu Ser Cys Ala Ala Ser Gly Phe Thr Val Ser
            20                  25                  30

Ser Asn Tyr Met Ser Trp Val Arg Gln Ala Pro Gly Lys Gly Leu Glu
        35                  40                  45

Trp Val Ala Val Ile Tyr Ser Gly Gly Asp Thr Tyr Tyr Ala Asp Ser
50                  55                  60

Val Lys Gly Arg Phe Thr Ile Ser Ser Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ser Trp Phe Gly Glu Ile Gly Tyr Trp Gly Gln Gly
            100                 105                 110

Thr Leu Val Thr Val Ser Ser
        115

<210> SEQ ID NO 59
<211> LENGTH: 123
<212> TYPE: PRT
<213> ORGANISM: Homo sapiens

<400> SEQUENCE: 59

Met Ala Gln Val Gln Leu Val Glu Leu Gly Gly Gly Leu Val Gln Ser
1               5                   10                  15

Gly Gly Ser Leu Arg Leu Ser Cys Ala Ala Pro Gly Leu Thr Phe Ser
            20                  25                  30

Ser Tyr Ala Met Ser Trp Val Arg Gln Ala Pro Gly Lys Gly Leu Glu
        35                  40                  45

Trp Val Ala Tyr Ile Ser Ser Ser Ser Thr Ile Tyr Tyr Ala Asp
            50                  55                  60

Ser Val Lys Gly Arg Phe Thr Ile Ser Arg Asp Asn Ala Lys Ser Ser
65                  70                  75                  80

Leu Tyr Leu Gln Met Thr Gly Leu Arg Ala Glu Asp Thr Ala Ile Tyr
                85                  90                  95

Tyr Cys Ala Thr Tyr Ile Ala Thr Ser Asp Lys Arg Gly Phe Asp Tyr
            100                 105                 110

Trp Gly Gln Gly Thr Leu Val Thr Val Ser Ser
        115                 120

<210> SEQ ID NO 60
<211> LENGTH: 117
<212> TYPE: PRT
<213> ORGANISM: Homo sapiens

<400> SEQUENCE: 60

Met Ala Gln Val Gln Leu Val Glu Ser Gly Gly Gly Val Val Lys Pro
1               5                   10                  15

Gly Gly Ser Leu Arg Leu Ser Cys Ala Ala Ser Gly Phe Ser Phe Ser
            20                  25                  30

Asp Tyr Gly Met His Trp Val Arg Gln Ala Pro Gly Lys Gly Leu Glu
        35                  40                  45

Trp Val Ala Phe Ile Pro Tyr Asp Gly Ser Lys Glu Tyr Tyr Ala Asp
            50                  55                  60

Ser Val Lys Gly Arg Phe Thr Ile Ser Arg Asp Asn Ser Glu Asn Thr
65                  70                  75                  80

Leu Tyr Leu Gln Met Asn Ser Leu Lys Ala Glu Asp Thr Ala Val Tyr
                85                  90                  95

Tyr Cys Met Lys Asp Gln Ala Arg Gly Ile Trp Gly Gln Gly Thr Leu
            100                 105                 110

Val Thr Val Ser Ser
        115

<210> SEQ ID NO 61
<211> LENGTH: 129
<212> TYPE: PRT
<213> ORGANISM: Artificial sequence
<220> FEATURE:
<223> OTHER INFORMATION: Consensus
<220> FEATURE:
<221> NAME/KEY: MISC_FEATURE
<222> LOCATION: (59)..(59)
<223> OTHER INFORMATION: Xaa represents position at which no consensus
      could be assigned
<220> FEATURE:
<221> NAME/KEY: MISC_FEATURE
<222> LOCATION: (102)..(104)
<223> OTHER INFORMATION: Xaa represents position at which no consensus
      could be assigned
<220> FEATURE:
<221> NAME/KEY: MISC_FEATURE
<222> LOCATION: (106)..(115)
<223> OTHER INFORMATION: Xaa represents position at which no consensus
      could be assigned

<400> SEQUENCE: 61

Met Ala Gln Val Gln Leu Gln Glu Ser Gly Gly Gly Val Val Gln Pro
1               5                   10                  15

Gly Gly Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu

```
                35                  40                  45
Trp Val Ala Val Ile Ser Ser Asp Gly Ser Xaa Thr Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Xaa Xaa Xaa Gly Xaa Xaa Xaa Xaa Xaa Xaa Xaa
            100                 105                 110

Xaa Xaa Xaa Phe Asp Tyr Trp Gly Gln Gly Thr Leu Val Thr Val Ser
        115                 120                 125

Ser

<210> SEQ ID NO 62
<211> LENGTH: 108
<212> TYPE: PRT
<213> ORGANISM: Homo sapiens

<400> SEQUENCE: 62

Ser Glu Leu Thr Gln Asp Ala Val Ser Val Ala Leu Gly Gln Thr Val
1               5                   10                  15

Arg Ile Thr Cys Gln Gly Asp Ser Leu Arg Ser Tyr Tyr Ala Ser Trp
            20                  25                  30

Tyr Gln Gln Lys Pro Gly Gln Ala Pro Leu Leu Val Ile Tyr Gly Glu
        35                  40                  45

Asn Asn Arg Pro Ser Gly Ile Pro Asp Arg Phe Ser Gly Ser Ser Ser
    50                  55                  60

Gly Asn Thr Ala Ser Leu Thr Ile Thr Gly Ala Gln Ala Glu Asp Glu
65                  70                  75                  80

Ala Asp Tyr Tyr Cys His Ser Arg Asp Ser Ser Gly Thr His Leu Arg
                85                  90                  95

Val Phe Gly Gly Gly Thr Lys Leu Thr Val Leu Gly
            100                 105

<210> SEQ ID NO 63
<211> LENGTH: 108
<212> TYPE: PRT
<213> ORGANISM: Homo sapiens

<400> SEQUENCE: 63

Asp Ile Val Met Thr Gln Ser Pro Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr His Thr Ile Ser Arg
                85                  90                  95

Thr Phe Gly Pro Gly Thr Lys Leu Glu Ile Lys Arg
            100                 105

<210> SEQ ID NO 64
```

<211> LENGTH: 109
<212> TYPE: PRT
<213> ORGANISM: Homo sapiens

<400> SEQUENCE: 64

Asp Val Val Met Thr Lys Ser Pro Gly Thr Leu Ser Leu Ser Leu Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Arg Gly Gln Ala Pro Arg Leu Leu
        35                  40                  45

Ile Tyr Gly Ala Ser Arg Arg Ala Thr Gly Ile Pro Asp Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Gly Thr Tyr Tyr Cys Gln Gln Leu Gly Ala Tyr Pro
                85                  90                  95

Leu Thr Phe Gly Gly Gly Thr Lys Leu Asp Ile Lys Arg
            100                 105

<210> SEQ ID NO 65
<211> LENGTH: 107
<212> TYPE: PRT
<213> ORGANISM: Homo sapiens

<400> SEQUENCE: 65

Asp Ile Val Met Thr Gln Ser Pro Ser Ser Leu Ser Ala Ser Val Gly
1               5                   10                  15

Asp Arg Val Thr Ile Thr Cys Arg Ala Ser Gly Ser Ser Ser Tyr Tyr
            20                  25                  30

Leu Ala Trp Tyr Gln Gln Arg Pro Gly Lys Ala Arg Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Leu Gln Thr Tyr Asn Gly Trp Thr
                85                  90                  95

Phe Gly Gln Gly Thr Lys Leu Glu Ile Lys Arg
            100                 105

<210> SEQ ID NO 66
<211> LENGTH: 108
<212> TYPE: PRT
<213> ORGANISM: Homo sapiens

<400> SEQUENCE: 66

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Arg Gly Gln Ala Pro Lys Leu Val Ile Tyr Gly
        35                  40                  45

Lys Asn Ile Arg Pro Ser Gly Ile Pro Asp Arg Phe Ser Gly Ser Ser
50                  55                  60

Ser Gly Asn Thr Ala Ser Leu Thr Ile Thr Gly Ala Gln Ala Glu Asp
65                  70                  75                  80

-continued

Glu Ala Asp Tyr Tyr Cys Asn Ser Arg Asp Ser Ser Gly Asn His Val
            85                  90                  95

Val Phe Gly Gly Gly Thr Lys Val Thr Val Leu Gly
        100                 105

<210> SEQ ID NO 67
<211> LENGTH: 112
<212> TYPE: PRT
<213> ORGANISM: Homo sapiens

<400> SEQUENCE: 67

Ser Val Leu Thr Gln Pro Pro Ser Val Ser Gly Ala Pro Gly Gln Arg
1               5                   10                  15

Val Thr Ile Ser Cys Thr Gly Ser Ser Ser Asn Ile Gly Ala Gly His
            20                  25                  30

Asp Val His Trp Tyr Gln Gln Phe Pro Gly Thr Ala Pro Lys Leu Leu
        35                  40                  45

Ile Phe Arg Thr Thr Asn Arg Pro Ser Gly Ile Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Glu Tyr Tyr Cys Gln Ser Tyr Asp Gly Arg Leu
                85                  90                  95

Ser Gly Ser Trp Arg Phe Gly Gly Gly Thr Lys Val Thr Val Leu Gly
            100                 105                 110

<210> SEQ ID NO 68
<211> LENGTH: 114
<212> TYPE: PRT
<213> ORGANISM: Homo sapiens

<400> SEQUENCE: 68

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Gly
            20                  25                  30

Ser Asn Asn Glu His Phe Leu Ala Trp Tyr Gln Gln Lys Pro Gly Thr
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Ile Pro Phe Thr Phe Gly Pro Gly Thr Arg Val Lys Ile
            100                 105                 110

Lys Arg

<210> SEQ ID NO 69
<211> LENGTH: 108
<212> TYPE: PRT
<213> ORGANISM: Homo sapiens

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Asp
            20                  25                  30

```
Leu Val Trp Cys Gln Gln Lys Pro Gly Lys Ala Pro Lys Arg Leu Ile
            35                  40                  45

Ser Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Gly Phe Pro Gln
                 85                  90                  95

Thr Phe Gly Gln Gly Thr Lys Leu Glu Ile Lys Arg
                100                 105
```

<210> SEQ ID NO 70
<211> LENGTH: 110
<212> TYPE: PRT
<213> ORGANISM: Homo sapiens

<400> SEQUENCE: 70

```
Ser Ala Leu Thr Gln Pro Ala Ser Val Ser Gly Ser Pro Gly Gln Ser
 1               5                  10                  15

Val Thr Ile Ser Cys Thr Gly Thr Ser Ser Asp Val Gly Gly Tyr Asn
                20                  25                  30

Tyr Val Ser Trp Tyr Gln Gln Asp Pro Lys Gln Ala Pro Lys Leu Met
            35                  40                  45

Ile Tyr Glu Val Ser Lys Arg Pro Ser Gly Val Pro Asp Arg Phe Ser
 50                  55                  60

Gly Ser Lys Ser Gly Asn Thr Ala Ser Leu Thr Val Ser Gly Leu Gln
 65                  70                  75                  80

Ala Glu Asp Glu Ala Asp Tyr Tyr Cys Ser Ala Ala Pro Thr Gly Ile
                 85                  90                  95

Met Met Thr Phe Gly Gly Gly Thr Lys Leu Thr Val Leu Gly
                100                 105                 110
```

<210> SEQ ID NO 71
<211> LENGTH: 109
<212> TYPE: PRT
<213> ORGANISM: Homo sapiens

<400> SEQUENCE: 71

```
Glu Ile Val Leu Thr Gln Ser Pro Ser Thr Leu Ser Ala Ser Ile Gly
 1               5                  10                  15

Asp Arg Ala Thr Ile Thr Cys Arg Ala Ser Gln Ser Ile Ser Ser Trp
                20                  25                  30

Leu Ala Trp Trp Tyr Gln Gln Lys Pro Gly Lys Ala Pro Lys Leu Leu
            35                  40                  45

Ile Tyr Lys Ala Ser Ser Leu Glu Ser Gly Val Pro Asp Arg Phe Ser
 50                  55                  60

Gly Ser Gly Ser Gly Thr Glu Phe Thr Leu Thr Ile Ser Ser Leu Gln
 65                  70                  75                  80

Pro Asp Asp Phe Ala Thr Tyr Tyr Cys Gln Gln Tyr Asn Ser Phe Pro
                 85                  90                  95

Thr Thr Phe Gly Gln Gly Thr Lys Leu Asn Ile Lys Arg
                100                 105
```

<210> SEQ ID NO 72
<211> LENGTH: 114
<212> TYPE: PRT
<213> ORGANISM: Homo sapiens

<400> SEQUENCE: 72

```
Asp Val Val Met Thr Gln Ser Pro Asp Ser Leu Ala Val Ser Leu Glu
1               5                   10                  15
Gln Arg Ala Thr Asn Thr Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Arg Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Asp Tyr Tyr Cys His Gln
                85                  90                  95
Tyr Tyr Ser Val Pro Phe Thr Phe Gly Gly Gly Thr Lys Leu Glu Ile
            100                 105                 110
Lys Arg
```

<210> SEQ ID NO 73
<211> LENGTH: 108
<212> TYPE: PRT
<213> ORGANISM: Homo sapiens

<400> SEQUENCE: 73

```
Ser Glu Leu Thr Gln Asp Pro Ala Val Ser Val Ala Leu Gly Gln Thr
1               5                   10                  15
Val Arg Ile Thr Cys Gln Gly Asp Ser Leu Arg Asn Ser Tyr Ala Asn
            20                  25                  30
Trp Tyr Gln Gln Lys Pro Gly Gln Ala Pro Val Leu Val Ile Tyr Gly
        35                  40                  45
Glu Asn Ser Arg Pro Ser Gly Ile Pro Asp Arg Phe Ser Gly Ser Gly
    50                  55                  60
Ser Gly Asn Thr Ala Ser Leu Thr Ile Ser Gly Thr Gln Ala Glu Asp
65                  70                  75                  80
Glu Ala Asp Tyr Tyr Cys Ser Ser Arg Asp Ser Ser Gly Thr His Leu
                85                  90                  95
Ser Phe Gly Gly Gly Thr Lys Val Thr Val Leu Gly
            100                 105
```

<210> SEQ ID NO 74
<211> LENGTH: 114
<212> TYPE: PRT
<213> ORGANISM: Homo sapiens

<400> SEQUENCE: 74

```
Glu Ile Val Leu Thr Gln Ser Asp Pro Ser Ala Ser Val Ser Leu Gly
1               5                   10                  15
Glu Arg Ala Thr Asn Thr Cys Lys Ser Ser Gln Ser Val Leu Tyr Ser
            20                  25                  30
Ser Asn Asn Lys Asn Asn Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
```

```
                    85                  90                  95
Tyr Tyr Ser Ala Pro Pro Thr Phe Gly Gly Thr Lys Leu Glu Ile
            100                 105                 110
Lys Arg

<210> SEQ ID NO 75
<211> LENGTH: 109
<212> TYPE: PRT
<213> ORGANISM: Homo sapiens

<400> SEQUENCE: 75

Ser Val Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Leu Leu Val Ile Tyr Gly
        35                  40                  45

Glu Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys His Ser Arg Asp Ser Ser Gly Thr His Leu
                85                  90                  95

Arg Val Phe Gly Gly Gly Thr Lys Val Thr Val Leu Gly
            100                 105

<210> SEQ ID NO 76
<211> LENGTH: 107
<212> TYPE: PRT
<213> ORGANISM: Homo sapiens

<400> SEQUENCE: 76

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Thr Tyr Tyr Ala Trp
            20                  25                  30

Tyr Gln Gln Lys Pro Gly Gln Ala Pro Ile Leu Val Ile Tyr Ala Lys
        35                  40                  45

Ser Asn Arg Pro Ser Gly Ile Pro Asp Arg Phe Ser Gly Ser Gly Ser
    50                  55                  60

Gly Asn Thr Ala Ser Leu Thr Ile Thr Gly Ala Gln Ala Glu Asp Glu
65                  70                  75                  80

Ala Asp Tyr Tyr Cys Asn Ser Arg Asp Arg Ser Asn Asn His Leu Leu
                85                  90                  95

Phe Gly Gly Gly Thr Lys Leu Thr Val Leu Gly
            100                 105

<210> SEQ ID NO 77
<211> LENGTH: 108
<212> TYPE: PRT
<213> ORGANISM: Homo sapiens

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Leu
            20                  25                  30
```

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Ser Pro Ile
                85                  90                  95

Thr Phe Gly Gln Gly Thr Lys Leu Glu Ile Lys Arg
                100                 105

<210> SEQ ID NO 78
<211> LENGTH: 108
<212> TYPE: PRT
<213> ORGANISM: Homo sapiens

<400> SEQUENCE: 78

Glu Ile Val Leu Thr Gln Ser Pro Ser Phe Leu Ser Ala Phe Val Gly
1               5                   10                  15

Asp Arg Ile Thr Ile Thr Cys Arg Ala Ser Gln Gly Ile Ser Tyr Tyr
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Ser Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys Arg
                100                 105

<210> SEQ ID NO 79
<211> LENGTH: 108
<212> TYPE: PRT
<213> ORGANISM: Homo sapiens

<400> SEQUENCE: 79

Ser Glu Leu Thr Gln Asp Pro Ala Val Ser Ala Ser Leu Gly Gln Thr
1               5                   10                  15

Val Arg Ile Thr Cys Gln Gly Asp Ser Pro Arg Ser Tyr Tyr Ala Ser
            20                  25                  30

Trp Tyr Gln Gln Lys Pro Gly Gln Ala Pro Val Leu Val Ile Tyr Gly
            35                  40                  45

Asn Ser Asn Arg Pro Ser Gly Val Pro Asp Arg Phe Ser Gly Ser Lys
        50                  55                  60

Ser Gly Thr Ser Ala Ser Leu Ala Ile Ser Gly Leu Gln Ser Glu Asp
65                  70                  75                  80

Glu Ala Asp Tyr Gly Cys Ala Ala Trp Asp Asp Ser Leu Asn Gly Pro
                85                  90                  95

Val Phe Gly Gly Gly Thr Lys Leu Thr Val Leu Gly
                100                 105

<210> SEQ ID NO 80
<211> LENGTH: 108
<212> TYPE: PRT
<213> ORGANISM: Artificial sequence
<220> FEATURE:

```
<223> OTHER INFORMATION: Consensus
<220> FEATURE:
<221> NAME/KEY: MISC_FEATURE
<222> LOCATION: (96)..(96)
<223> OTHER INFORMATION: Xaa represents position at which no consensus
      could be assigned

<400> SEQUENCE: 80

Asp Ile Val Met Thr Gln Ser Pro Pro Ser Leu Ser Val Ser Leu Gly
1               5                   10                  15

Gln Arg Val Thr Ile Thr Cys Arg Gly Ser Gln Ser Ile Ser Tyr Tyr
            20                  25                  30

Leu Asn Trp Tyr Gln Gln Lys Pro Gly Gln Ala Pro Lys Leu Leu Ile
        35                  40                  45

Tyr Ala Ala Ser Thr Arg Pro Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Glu Ala Asp Tyr Tyr Cys Gln Gln Tyr Asp Ser Ser Pro Xaa
                85                  90                  95

Thr Phe Gly Gly Gly Thr Lys Leu Thr Ile Lys Arg
            100                 105

<210> SEQ ID NO 81
<211> LENGTH: 117
<212> TYPE: PRT
<213> ORGANISM: Homo sapiens

<400> SEQUENCE: 81

Gln Val Gln Leu Gln Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser
        115

<210> SEQ ID NO 82
<211> LENGTH: 117
<212> TYPE: PRT
<213> ORGANISM: Homo sapiens

<400> SEQUENCE: 82

Gln Val Gln Leu Gln Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

```
Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Val Gly Ala Lys Gly Asn Trp Gly Gln Gly Thr Leu
            100                 105                 110

Val Thr Val Ser Ser
            115

<210> SEQ ID NO 83
<211> LENGTH: 117
<212> TYPE: PRT
<213> ORGANISM: Homo sapiens

<400> SEQUENCE: 83

Gln Val Gln Leu Gln Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Phe Ala Gly Ala Ile Ala Tyr Trp Gly Gln Gly Thr Leu
            100                 105                 110

Val Thr Val Ser Ser
            115

<210> SEQ ID NO 84
<211> LENGTH: 123
<212> TYPE: PRT
<213> ORGANISM: Homo sapiens

<400> SEQUENCE: 84

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Ala Ile Ser Gly Ser Gly Asp Asn Thr Tyr Tyr Ala Asp Ser Val
        50                  55                  60

Lys Gly Arg Phe Thr Ile Ser Arg Asp Asn Ser Glu Asn Thr Val His
 65                  70                  75                  80

Leu Gln Met Ala Gly Leu Arg Ala Glu Asp Thr Ala Leu Tyr Phe Cys
                 85                  90                  95

Ala Lys Asp Gly Pro Ala Val Gly Asn Pro Gln Gly Tyr Phe Asp Phe
            100                 105                 110

Trp Gly Arg Gly Thr Leu Val Thr Val Ser Ser
            115                 120
```

<210> SEQ ID NO 85
<211> LENGTH: 117
<212> TYPE: PRT
<213> ORGANISM: Homo sapiens

<400> SEQUENCE: 85

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ser Met Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Arg Gly Ala Leu Asp Tyr Trp Gly Gln Gly Thr Leu
            100                 105                 110

Val Thr Val Ser Ser
        115

<210> SEQ ID NO 86
<211> LENGTH: 123
<212> TYPE: PRT
<213> ORGANISM: Homo sapiens

<400> SEQUENCE: 86

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Ala Ala Arg Ser Gly Tyr Tyr Gly Met Asp Val
            100                 105                 110

Trp Gly Gln Gly Thr Leu Val Thr Val Ser Ser
        115                 120

<210> SEQ ID NO 87
<211> LENGTH: 117
<212> TYPE: PRT
<213> ORGANISM: Homo sapiens

<400> SEQUENCE: 87

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val

```
                35                  40                  45
Ala Val Ile Ser Tyr Asp Gly Ser Asn Lys Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Phe Ala Gly Ala Ile Ala Tyr Trp Gly Gln Gly Thr Leu
            100                 105                 110
Val Thr Val Ser Ser
        115

<210> SEQ ID NO 88
<211> LENGTH: 123
<212> TYPE: PRT
<213> ORGANISM: Homo sapiens

<400> SEQUENCE: 88

Gln Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Ser Ser Tyr
             20                  25                  30
Ala Met Ser Trp Val Arg Gln Ala Pro Gly Lys Gly Leu Glu Trp Val
         35                  40                  45
Ala Ala Ile Ser Gly Ser Gly Asp Asn Thr Tyr Tyr Ala Asp Ser Val
     50                  55                  60
Lys Gly Arg Phe Thr Ile Ser Arg Asp Asn Ser Glu Asn Thr Val His
 65                  70                  75                  80
Leu Gln Met Ala Gly Leu Arg Ala Glu Asp Thr Ala Leu Tyr Phe Cys
                 85                  90                  95
Ala Lys Asp Gly Pro Ala Val Gly Asn Pro Gln Gly Tyr Phe Asp Phe
            100                 105                 110
Trp Gly Arg Gly Thr Leu Val Thr Val Ser Ser
        115                 120

<210> SEQ ID NO 89
<211> LENGTH: 117
<212> TYPE: PRT
<213> ORGANISM: Homo sapiens

<400> SEQUENCE: 89

Gln Val Gln Leu Val Gln Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
         35                  40                  45
Ala Val Ile Ser Tyr Asp Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Leu Pro Asp Ser Asn Gly Tyr Trp Gly Gln Gly Thr Leu
            100                 105                 110
Val Thr Val Ser Ser
```

<210> SEQ ID NO 90
<211> LENGTH: 123
<212> TYPE: PRT
<213> ORGANISM: Homo sapiens

<400> SEQUENCE: 90

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ala Ile Ser Gly Ser Gly Asp Asn Thr Tyr Tyr Ala Asp Ser Val
    50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Ala Val Gly Asn Pro Gln Gly Tyr Phe Asp Phe
            100                 105                 110

Trp Gly Arg Gly Thr Leu Val Thr Val Ser Ser
        115                 120
```

<210> SEQ ID NO 91
<211> LENGTH: 117
<212> TYPE: PRT
<213> ORGANISM: Homo sapiens

<400> SEQUENCE: 91

```
Gln Val Gln Leu Val Gln Ser Gly Gly Gly Val Val His Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ser Met Ser Tyr Asp Gly Asn Asn Lys Tyr Tyr Ala Asp Ser Val
    50                  55                  60

Lys Gly Arg Phe Thr Thr Pro Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Arg Gly Ala Leu Asp Tyr Trp Gly Gln Gly Thr Leu
            100                 105                 110

Val Thr Val Ser Ser
        115
```

<210> SEQ ID NO 92
<211> LENGTH: 117
<212> TYPE: PRT
<213> ORGANISM: Homo sapiens

<400> SEQUENCE: 92

```
Gln Val Gln Leu Gln Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30
```

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Homo sapiens

<400> SEQUENCE: 93

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Ala Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Ala Gln Gly Thr Leu
            100                 105                 110

Val Thr Val Ser Ser
        115

<210> SEQ ID NO 94
<211> LENGTH: 117
<212> TYPE: PRT
<213> ORGANISM: Homo sapiens

<400> SEQUENCE: 94

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Gly Gln Gly Thr Leu
            100                 105                 110

<210> SEQ ID NO 95
<211> LENGTH: 123
<212> TYPE: PRT
<213> ORGANISM: Homo sapiens

<400> SEQUENCE: 95

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ala Ile Ser Gly Ser Gly Asp Asn Thr Tyr Tyr Ala Asp Ser Val
    50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Glu Val Gly Asn Pro Gln Gly Tyr Phe Asp Phe
            100                 105                 110

Trp Gly Arg Gly Thr Leu Val Thr Val Ser Ser
        115                 120

<210> SEQ ID NO 96
<211> LENGTH: 117
<212> TYPE: PRT
<213> ORGANISM: Homo sapiens

<400> SEQUENCE: 96

Gln Val Gln Leu Gln Gln Ser Gly Glu Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Gly Gln Gly Thr Leu
            100                 105                 110

Val Thr Val Ser Ser
        115

<210> SEQ ID NO 97
<211> LENGTH: 117
<212> TYPE: PRT
<213> ORGANISM: Homo sapiens

<400> SEQUENCE: 97

Gln Val Gln Leu Val Gln Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ser Met Ser Tyr Asp Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Arg Gly Ala Leu Asp Tyr Trp Gly Gln Gly Thr Leu
            100                 105                 110

Val Thr Val Ser Ser
            115

<210> SEQ ID NO 98
<211> LENGTH: 103
<212> TYPE: PRT
<213> ORGANISM: Homo sapiens

<400> SEQUENCE: 98

Glu Ile Val Leu Thr Gln Ser Pro Ser Phe Leu Ser Ala Ser Val Gly
1               5                   10                  15

Asp Arg Val Thr Ile Thr Cys Arg Ala Ser His Gly Ile Asn Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys
            100

<210> SEQ ID NO 99
<211> LENGTH: 103
<212> TYPE: PRT
<213> ORGANISM: Homo sapiens

<400> SEQUENCE: 99

Glu Ile Val Leu Thr Gln Ser Pro Ser Thr Leu Ser Ala Ser Val Gly
1               5                   10                  15

Glu Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Leu Trp
                85                  90                  95

Thr Phe Gly Gln Gly Thr Lys
            100
```

<210> SEQ ID NO 100
<211> LENGTH: 103
<212> TYPE: PRT
<213> ORGANISM: Homo sapiens

<400> SEQUENCE: 100

Glu Ile Val Leu Thr Gln Ser Pro Ser Ile Leu Ser Ala Ser Val Gly
1               5                   10                  15

Asp Arg Val Thr Ile Thr Cys Arg Ala Ser His Gly Ile Asn Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys
            100

<210> SEQ ID NO 101
<211> LENGTH: 109
<212> TYPE: PRT
<213> ORGANISM: Homo sapiens

<400> SEQUENCE: 101

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Asn Lys Asp Tyr Leu Ala Trp Tyr Gln Gln Lys Pro Gly Gln
        35                  40                  45

Ser Pro Arg Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Arg Leu Gln Ala Glu Asp Val Ala Val Tyr Tyr Cys Gln His
                85                  90                  95

Tyr Tyr Ser Tyr Pro Leu Thr Phe Gly Gln Gly Thr Lys
            100                 105

<210> SEQ ID NO 102
<211> LENGTH: 103
<212> TYPE: PRT
<213> ORGANISM: Homo sapiens

<400> SEQUENCE: 102

Glu Ile Val Leu Thr Gln Ser Pro Ser Thr Leu Ser Ala Ser Ile Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Gly Leu Leu Pro

```
                65                  70                  75                  80
Glu Asp Phe Ala Ser Tyr Phe Cys Gln Gln Ala Ser Val Phe Pro Val
                    85                  90                  95

Thr Phe Gly Gly Gly Thr Lys
            100
```

<210> SEQ ID NO 103
<211> LENGTH: 105
<212> TYPE: PRT
<213> ORGANISM: Homo sapiens

<400> SEQUENCE: 103

```
Glu Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Ser Asn Pro Tyr Pro
                85                  90                  95

Leu Leu Thr Phe Gly Gly Gly Thr Lys
            100                 105
```

<210> SEQ ID NO 104
<211> LENGTH: 102
<212> TYPE: PRT
<213> ORGANISM: Homo sapiens

<400> SEQUENCE: 104

```
Glu Ile Val Leu Thr Gln Ser Pro Ser Phe Leu Ser Ala Ser Val Gly
1               5                   10                  15

Asp Arg Val Thr Ile Thr Cys Arg Ala Ser His Gly Ile Asn Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Ala Arg Thr Lys
            100
```

<210> SEQ ID NO 105
<211> LENGTH: 109
<212> TYPE: PRT
<213> ORGANISM: Homo sapiens

<400> SEQUENCE: 105

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30
```

```
Ser Asn Asn Lys Asp Tyr Leu Ala Trp Tyr Gln Gln Lys Pro Gly Gln
            35                  40                  45

Ser Pro Arg Leu Leu Ile Ser Trp Ala Ser Thr Arg Glu Ser Gly Val
 50                  55                  60

Pro Ser Arg Phe Ser Gly Ser Gly Thr Asp Phe Thr Leu Thr
 65                  70                  75                  80

Ile Asn Arg Leu Gln Ala Glu Asp Val Ala Val Tyr Tyr Cys Gln His
                85                  90                  95

Tyr Tyr Ser Tyr Pro Leu Thr Phe Gly Gln Gly Thr Lys
            100                 105

<210> SEQ ID NO 106
<211> LENGTH: 103
<212> TYPE: PRT
<213> ORGANISM: Homo sapiens

<400> SEQUENCE: 106

Asp Val Val Met Thr Gln Ser Pro Ser Thr Leu Ser Ala Ser Val Gly
 1               5                  10                  15

Asp Arg Val Thr Ile Thr Cys Arg Ala Ser Glu Asn Ile Asn Arg Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Cys Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys His Gln Tyr Thr Thr Tyr Leu Trp
                85                  90                  95

Thr Phe Gly Gln Gly Thr Lys
            100

<210> SEQ ID NO 107
<211> LENGTH: 109
<212> TYPE: PRT
<213> ORGANISM: Homo sapiens

<400> SEQUENCE: 107

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Ser
                20                  25                  30

Ser Asn Asn Lys Asp Tyr Leu Ala Trp Tyr Gln Gln Lys Pro Gly Gln
            35                  40                  45

Ser Pro Arg Leu Leu Ile Pro Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Asn Arg Leu Gln Ala Glu Asp Val Ala Val Tyr Tyr Cys Gln His
                85                  90                  95

Tyr Tyr Ser Tyr Pro Leu Thr Phe Gly Gln Gly Thr Lys
            100                 105

<210> SEQ ID NO 108
<211> LENGTH: 102
<212> TYPE: PRT
<213> ORGANISM: Homo sapiens
```

<400> SEQUENCE: 108

Glu Ile Val Leu Thr Gln Ser Pro Ser Thr Leu Ser Ala Ser Ile Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Gly Leu Leu Pro
65                  70                  75                  80

Glu Asp Phe Ala Ser Tyr Phe Cys Gln Gln Ala Ser Val Phe Pro Val
                85                  90                  95

Thr Phe Ala Arg Thr Lys
            100

<210> SEQ ID NO 109
<211> LENGTH: 103
<212> TYPE: PRT
<213> ORGANISM: Homo sapiens

<400> SEQUENCE: 109

Glu Ile Cys Val Thr Gln Ser Pro Ser Phe Leu Ser Ala Ser Val Gly
1               5                   10                  15

Asp Arg Val Thr Ile Thr Cys Arg Ala Ser His Gly Ile Asn Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys
            100

<210> SEQ ID NO 110
<211> LENGTH: 103
<212> TYPE: PRT
<213> ORGANISM: Homo sapiens

<400> SEQUENCE: 110

Glu Ile Val Leu Thr Gln Ser Pro Ser Thr Leu Ser Ala Ser Val Gly
1               5                   10                  15

Glu Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Leu Trp
                85                  90                  95

Thr Phe Gly Gln Gly Thr Lys
            100

<210> SEQ ID NO 111
<211> LENGTH: 103
<212> TYPE: PRT
<213> ORGANISM: Homo sapiens

<400> SEQUENCE: 111

Glu Ile Val Leu Thr Gln Ser Pro Ser Thr Leu Ser Ala Ser Val Gly
1               5                   10                  15

Glu Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Asp Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Leu Trp
                85                  90                  95

Thr Phe Gly Gln Gly Thr Lys
            100

<210> SEQ ID NO 112
<211> LENGTH: 109
<212> TYPE: PRT
<213> ORGANISM: Homo sapiens

<400> SEQUENCE: 112

Asp Ile Val Met Thr Lys Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Lys Asn Lys Asp Tyr Leu Ala Trp Tyr Gln Lys Lys Pro Gly Gln
        35                  40                  45

Ser Pro Arg Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Arg Leu Gln Ala Glu Asp Val Ala Val Tyr Tyr Cys Gln His
                85                  90                  95

Tyr Tyr Ser Tyr Pro Leu Thr Phe Gly Gln Gly Thr Lys
            100                 105

<210> SEQ ID NO 113
<211> LENGTH: 103
<212> TYPE: PRT
<213> ORGANISM: Homo sapiens

<400> SEQUENCE: 113

Glu Ile Val Leu Thr Gln Ser Pro Ser Thr Leu Ser Ala Ser Val Gly
1               5                   10                  15

Glu Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly

```
              50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Ser Thr Tyr Leu Trp
                 85                  90                  95

Thr Phe Gly Gln Gly Thr Lys
            100

<210> SEQ ID NO 114
<211> LENGTH: 103
<212> TYPE: PRT
<213> ORGANISM: Homo sapiens

<400> SEQUENCE: 114

Glu Ile Val Leu Thr Gln Ser Pro Ser Thr Leu Ser Ala Ser Ile Gly
 1               5                  10                  15

Asp Arg Val Thr Ile Thr Cys Arg Ala Ser Gln Gly Ile Ser Asn Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Glu Phe Thr Leu Thr Ile Ser Gly Leu Leu Pro
 65                  70                  75                  80

Glu Asp Phe Ala Ser Tyr Phe Cys Leu Gln Ala Ser Val Phe Pro Val
                 85                  90                  95

Thr Phe Gly Gly Gly Thr Lys
            100

<210> SEQ ID NO 115
<211> LENGTH: 131
<212> TYPE: PRT
<213> ORGANISM: Artificial sequence
<220> FEATURE:
<223> OTHER INFORMATION: Optimum ICS for human variable chains
<220> FEATURE:
<221> NAME/KEY: MISC_FEATURE
<222> LOCATION: 5, 6, 11, 13, 16, 23, 30, 31, 33, 35..37, 39, 51..53
<223> OTHER INFORMATION: Xaa represents position at which no consensus
      could be assigned
<220> FEATURE:
<221> NAME/KEY: MISC_FEATURE
<222> LOCATION: 55..57, 59..61, 79, 82, 83, 87, 88, 96, 98, 101,
      103..120, 123
<223> OTHER INFORMATION: Xaa represents position at which no consensus
      could be assigned

<400> SEQUENCE: 115

Gln Val Gln Leu Xaa Xaa Ser Gly Gly Gly Xaa Val Xaa Pro Gly Xaa
 1               5                  10                  15

Ser Leu Arg Leu Ser Cys Xaa Ala Ser Gly Phe Thr Phe Xaa Xaa Tyr
                 20                  25                  30

Xaa Met Xaa Xaa Xaa Trp Xaa Arg Gln Ala Pro Gly Lys Gly Leu Glu
             35                  40                  45

Trp Val Xaa Xaa Xaa Ser Xaa Xaa Gly Xaa Xaa Xaa Tyr Tyr Ala
         50                  55                  60

Asp Ser Val Lys Gly Arg Phe Thr Ile Ser Arg Asp Asn Ser Xaa Asn
 65                  70                  75                  80

Thr Xaa Xaa Leu Gln Met Xaa Xaa Leu Arg Ala Glu Asp Thr Ala Xaa
                 85                  90                  95
```

```
Tyr Xaa Cys Ala Xaa Asp Xaa Xaa Xaa Xaa Xaa Xaa Xaa Xaa
            100                 105                 110

Xaa Xaa Xaa Xaa Xaa Xaa Xaa Xaa Trp Gly Xaa Gly Thr Leu Val Thr
        115                 120                 125

Val Ser Ser
    130

<210> SEQ ID NO 116
<211> LENGTH: 130
<212> TYPE: PRT
<213> ORGANISM: Artificial sequence
<220> FEATURE:
<223> OTHER INFORMATION: Optimum ICS for mouse variable chains
<220> FEATURE:
<221> NAME/KEY: MISC_FEATURE
<222> LOCATION: 1..18, 20, 23, 24, 26..33, 35..37, 39..42, 44..46,
      49..52
<223> OTHER INFORMATION: Xaa represents position at which no consensus
      could be assigned
<220> FEATURE:
<221> NAME/KEY: MISC_FEATURE
<222> LOCATION: 54..74, 76..81, 83, 86, 87, 89, 93, 95, 100, 102..119
<223> OTHER INFORMATION: Xaa represents position at which no consensus
      could be assigned
<220> FEATURE:
<221> NAME/KEY: MISC_FEATURE
<222> LOCATION: 122, 125, 126, 130
<223> OTHER INFORMATION: Xaa represents position at which no consensus
      could be assigned

<400> SEQUENCE: 116

Xaa Xaa Xaa Xaa Xaa Xaa Xaa Xaa Xaa Xaa Xaa Xaa Xaa Xaa
1               5                   10                  15

Xaa Xaa Lys Xaa Ser Cys Xaa Xaa Ser Gly Xaa Xaa Xaa Xaa Xaa
            20                  25                  30

Xaa Met Xaa Xaa Xaa Trp Xaa Xaa Xaa Xaa Pro Xaa Xaa Xaa Leu Glu
        35                  40                  45

Xaa Xaa Xaa Xaa Ile Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Asp Xaa Xaa Xaa Xaa Xaa
65                  70                  75                  80

Xaa Tyr Xaa Gln Met Xaa Xaa Leu Xaa Ser Glu Asp Xaa Ala Xaa Tyr
        85                  90                  95

Tyr Cys Ala Xaa Asp Xaa Xaa Xaa Xaa Xaa Xaa Xaa Xaa Xaa Xaa
            100                 105                 110

Xaa Xaa Xaa Xaa Xaa Xaa Xaa Trp Gly Xaa Gly Thr Xaa Xaa Thr Val
        115                 120                 125

Ser Xaa
    130

<210> SEQ ID NO 117
<211> LENGTH: 130
<212> TYPE: PRT
<213> ORGANISM: Artificial sequence
<220> FEATURE:
<223> OTHER INFORMATION: Optimum ICS extrapolated between man and mouse
<220> FEATURE:
<221> NAME/KEY: MISC_FEATURE
<222> LOCATION: 1.. 20, 23, 24, 27..33, 35..37, 39..42, 44..46, 49..74
<223> OTHER INFORMATION: Xaa represents position at which no consensus
      could be assigned
<220> FEATURE:
<221> NAME/KEY: MISC_FEATURE
<222> LOCATION: 76..83, 86, 87, 89, 93, 95, 97, 100, 102..119
<223> OTHER INFORMATION: Xaa represents position at which no consensus
      could be assigned
```

```
<220> FEATURE:
<221> NAME/KEY: MISC_FEATURE
<222> LOCATION: 122, 125, 126, 130
<223> OTHER INFORMATION: Xaa represents position at which no consensus
      could be assigned

<400> SEQUENCE: 117

Xaa Xaa Xaa Xaa Xaa Xaa Xaa Xaa Xaa Xaa Xaa Xaa Xaa Xaa
1               5                   10                  15

Xaa Xaa Xaa Xaa Ser Cys Xaa Xaa Ser Gly Xaa Xaa Xaa Xaa Xaa
            20              25                  30

Xaa Met Xaa Xaa Xaa Trp Xaa Xaa Xaa Xaa Pro Xaa Xaa Xaa Leu Glu
        35                  40                  45

Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Asp Xaa Xaa Xaa Xaa
65                  70                  75                  80

Xaa Xaa Xaa Gln Met Xaa Xaa Leu Xaa Ser Glu Asp Xaa Ala Xaa Tyr
                85                  90                  95

Xaa Cys Ala Xaa Asp Xaa Xaa Xaa Xaa Xaa Xaa Xaa Xaa Xaa Xaa
            100                 105                 110

Xaa Xaa Xaa Xaa Xaa Xaa Xaa Trp Gly Xaa Gly Thr Xaa Xaa Thr Val
        115                 120                 125

Ser Xaa
    130

<210> SEQ ID NO 118
<211> LENGTH: 115
<212> TYPE: PRT
<213> ORGANISM: Artificial sequence
<220> FEATURE:
<223> OTHER INFORMATION: Optimum ICS for human variable chains
<220> FEATURE:
<221> NAME/KEY: MISC_FEATURE
<222> LOCATION: 1..4, 6, 7, 9..15, 17..20, 22, 24..40, 44, 45, 48, 49,
      51..53
<223> OTHER INFORMATION: Xaa represents position at which no consensus
      could be assigned
<220> FEATURE:
<221> NAME/KEY: MISC_FEATURE
<222> LOCATION: 55..62, 64..68, 72, 75..78, 82..87, 89, 91, 93, 95..113
<223> OTHER INFORMATION: Xaa represents position at which no consensus
      could be assigned

<400> SEQUENCE: 118

Xaa Xaa Xaa Xaa Thr Xaa Pro Xaa Xaa Xaa Xaa Xaa Xaa Xaa Gly
1               5                   10                  15

Xaa Xaa Xaa Xaa Ile Xaa Cys Xaa Xaa Xaa Xaa Xaa Xaa Xaa Xaa
            20              25                  30

Xaa Xaa Xaa Xaa Xaa Xaa Xaa Trp Tyr Gln Xaa Xaa Pro Gly Xaa
        35                  40                  45

Xaa Pro Xaa Xaa Xaa Ile Xaa Xaa Xaa Xaa Xaa Xaa Xaa Ser Gly Xaa
    50                  55                  60

Xaa Xaa Xaa Xaa Ser Gly Ser Xaa Ser Gly Xaa Xaa Xaa Leu Thr
65                  70                  75                  80

Ile Xaa Xaa Xaa Xaa Xaa Xaa Asp Xaa Ala Xaa Tyr Xaa Cys Xaa Xaa
        85                  90                  95

Xaa Xaa Xaa Xaa Xaa Xaa Xaa Xaa Xaa Xaa Xaa Xaa
            100                 105                 110

Xaa Thr Lys
    115
```

```
<210> SEQ ID NO 119
<211> LENGTH: 115
<212> TYPE: PRT
<213> ORGANISM: Artificial sequence
<220> FEATURE:
<223> OTHER INFORMATION: Optimum ICS for mouse variable chains
<220> FEATURE:
<221> NAME/KEY: MISC_FEATURE
<222> LOCATION: 3..6, 8, 9..15, 17..22, 24, 25, 27..40, 42..62, 64, 66
<223> OTHER INFORMATION: Xaa represents position at which no consensus
      could be assigned
<220> FEATURE:
<221> NAME/KEY: MISC_FEATURE
<222> LOCATION: 69, 72, 74..80, 82..87, 89..91, 93, 95..108, 110, 112
<223> OTHER INFORMATION: Xaa represents position at which no consensus
      could be assigned

<400> SEQUENCE: 119

Asp Ile Xaa Xaa Xaa Gln Xaa Pro Xaa Xaa Xaa Xaa Xaa Xaa Xaa Gly
1               5                   10                  15

Xaa Xaa Xaa Xaa Xaa Xaa Cys Xaa Xaa Ser Xaa Xaa Xaa Xaa Xaa
            20                  25                  30

Xaa Xaa Xaa Xaa Xaa Xaa Xaa Xaa Trp Xaa Xaa Xaa Xaa Xaa Xaa
        35                  40                  45

Xaa Xaa Xaa Xaa Xaa Xaa Xaa Xaa Xaa Xaa Xaa Xaa Gly Xaa
    50                  55                  60

Pro Xaa Arg Phe Xaa Gly Ser Xaa Ser Xaa Xaa Xaa Xaa Xaa Xaa
65                  70                  75                  80

Ile Xaa Xaa Xaa Xaa Xaa Xaa Asp Xaa Xaa Xaa Tyr Xaa Cys Xaa
            85                  90                  95

Xaa Xaa Xaa Xaa Xaa Xaa Xaa Xaa Xaa Xaa Xaa Thr Xaa Gly Xaa
            100                 105                 110

Gly Thr Lys
        115

<210> SEQ ID NO 120
<211> LENGTH: 115
<212> TYPE: PRT
<213> ORGANISM: Artificial sequence
<220> FEATURE:
<223> OTHER INFORMATION: Optimum ICS extrapolated between man and mouse
<220> FEATURE:
<221> NAME/KEY: MISC_FEATURE
<222> LOCATION: 1..7, 9..15, 17..22, 24..40, 42..63
<223> OTHER INFORMATION: Xaa represents position at which no consensus
      could be assigned
<220> FEATURE:
<221> NAME/KEY: MISC_FEATURE
<222> LOCATION: 64..69, 72, 74..80, 82..87, 89..91, 93, 95..113
<223> OTHER INFORMATION: Xaa represents position at which no consensus
      could be assigned

<400> SEQUENCE: 120

Xaa Xaa Xaa Xaa Xaa Xaa Xaa Pro Xaa Xaa Xaa Xaa Xaa Xaa Xaa Gly
1               5                   10                  15

Xaa Xaa Xaa Xaa Xaa Xaa Cys Xaa Xaa Xaa Xaa Xaa Xaa Xaa Xaa
            20                  25                  30

Xaa Xaa Xaa Xaa Xaa Xaa Xaa Xaa Trp Xaa Xaa Xaa Xaa Xaa Xaa
        35                  40                  45

Xaa Xaa Xaa Xaa Xaa Xaa Xaa Xaa Xaa Xaa Xaa Xaa Gly Xaa
    50                  55                  60

Xaa Xaa Xaa Xaa Xaa Gly Ser Xaa Ser Xaa Xaa Xaa Xaa Xaa Xaa
65                  70                  75                  80
```

```
Ile Xaa Xaa Xaa Xaa Xaa Xaa Asp Xaa Xaa Xaa Tyr Xaa Cys Xaa Xaa
                85              90                  95

Xaa Xaa Xaa Xaa Xaa Xaa Xaa Xaa Xaa Xaa Xaa Xaa Xaa Xaa Xaa Xaa
                100             105                 110

Xaa Thr Lys
        115

<210> SEQ ID NO 121
<211> LENGTH: 27
<212> TYPE: DNA
<213> ORGANISM: Artificial sequence
<220> FEATURE:
<223> OTHER INFORMATION: Primer

<400> SEQUENCE: 121
cagggatccg agcgcggcct ggtgaag                                    27

<210> SEQ ID NO 122
<211> LENGTH: 27
<212> TYPE: DNA
<213> ORGANISM: Artificial sequence
<220> FEATURE:
<223> OTHER INFORMATION: Primer

<400> SEQUENCE: 122
caggaattca tcgttgggcc agatctg                                    27

<210> SEQ ID NO 123
<211> LENGTH: 27
<212> TYPE: DNA
<213> ORGANISM: Artificial sequence
<220> FEATURE:
<223> OTHER INFORMATION: Primer

<400> SEQUENCE: 123
cagggatccg aagcccttca gcggcca                                    27

<210> SEQ ID NO 124
<211> LENGTH: 27
<212> TYPE: DNA
<213> ORGANISM: Artificial sequence
<220> FEATURE:
<223> OTHER INFORMATION: Primer

<400> SEQUENCE: 124
caggaattcc gagatctgag tggccat                                    27
```